(12) United States Patent
Bruggeman et al.

(10) Patent No.: US 8,912,304 B2
(45) Date of Patent: Dec. 16, 2014

(54) POLYOL-BASED POLYMERS

(75) Inventors: Joost P. Bruggeman, GE Rotterdam (NL); Christiaan Nijst, PD Amsterdam (NL); Daniel S. Kohane, Newton, MA (US); Robert S. Langer, Newton, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 889 days.

(21) Appl. No.: 12/600,596

(22) PCT Filed: May 16, 2008

(86) PCT No.: PCT/US2008/063900
§ 371 (c)(1),
(2), (4) Date: Sep. 17, 2010

(87) PCT Pub. No.: WO2008/144514
PCT Pub. Date: Nov. 27, 2008

(65) Prior Publication Data
US 2011/0008277 A1     Jan. 13, 2011

Related U.S. Application Data

(60) Provisional application No. 60/930,606, filed on May 17, 2007.

(51) Int. Cl.
| | | |
|---|---|---|
| *C08G 63/02* | (2006.01) | |
| *C08G 63/668* | (2006.01) | |
| *A61L 27/54* | (2006.01) | |
| *A61L 27/52* | (2006.01) | |
| *A61L 27/58* | (2006.01) | |
| *A61L 27/38* | (2006.01) | |
| *A61L 27/16* | (2006.01) | |
| *C08G 63/21* | (2006.01) | |
| *C08F 283/00* | (2006.01) | |

(52) U.S. Cl.
CPC ......... *C08G 63/668* (2013.01); *A61L 2300/604* (2013.01); *A61L 27/54* (2013.01); *A61L 27/52* (2013.01); *A61L 27/58* (2013.01); *A61L 27/38* (2013.01); *A61L 27/16* (2013.01); *C08G 63/21* (2013.01)
USPC ............ 528/272; 528/300; 528/303; 525/418

(58) Field of Classification Search
USPC .......................... 528/300, 303, 272; 525/418
See application file for complete search history.

(56) References Cited

U.S. PATENT DOCUMENTS

| | | | |
|---|---|---|---|
| 1,489,744 A | | 4/1924 | Downs et al. |
| 1,779,367 A | | 10/1930 | Bruson |
| 3,661,955 A | * | 5/1972 | Centolella et al. ............ 560/182 |
| 3,772,064 A | | 11/1973 | Mendelsohn et al. |
| 3,978,203 A | * | 8/1976 | Wise ............................. 514/169 |
| 4,048,256 A | | 9/1977 | Casey et al. |
| 4,064,086 A | | 12/1977 | Cowsar et al. |
| 4,177,596 A | | 12/1979 | Dillow |
| 4,205,399 A | | 6/1980 | Shalaby et al. |
| 4,275,169 A | | 6/1981 | Rudner et al. |
| 4,343,048 A | | 8/1982 | Ross et al. |
| 4,638,045 A | | 1/1987 | Kohn et al. |
| 4,806,621 A | | 2/1989 | Kohn et al. |
| 4,946,929 A | | 8/1990 | D'Amore et al. |
| 5,010,167 A | | 4/1991 | Ron et al. |
| 5,019,379 A | | 5/1991 | Domb et al. |
| 5,116,937 A | | 5/1992 | Greene |
| 5,166,310 A | | 11/1992 | Rooney |
| 5,286,763 A | | 2/1994 | Gerhart et al. |
| 5,295,985 A | | 3/1994 | Romesser et al. |
| 5,399,665 A | | 3/1995 | Barrera et al. |
| 5,489,298 A | | 2/1996 | Love et al. |
| 5,505,808 A | | 4/1996 | Hallman et al. |
| 5,510,453 A | | 4/1996 | Kressdorf et al. |
| 5,512,600 A | | 4/1996 | Mikos et al. |
| 5,514,378 A | | 5/1996 | Mikos et al. |

(Continued)

FOREIGN PATENT DOCUMENTS

| | | |
|---|---|---|
| DE | 31 23 465 A1 | 12/1982 |
| DE | 4219768 A1 | 12/1993 |

(Continued)

OTHER PUBLICATIONS

M. Lawson "Sugar Alcohols", Abstract, Published on Dec. 4, 2000.*

(Continued)

*Primary Examiner* — Ling Choi
*Assistant Examiner* — Gennadiy Mesh
(74) *Attorney, Agent, or Firm* — Choate Hall & Stewart, LLP; Brenda Herschbach Jarrell; Xiaodong Li

(57) ABSTRACT

The present invention provides inventive polyol-based polymers, materials, pharmaceutical compositions, and methods of making and using the inventive polymers and materials. In certain aspects of the invention, an inventive polymer corresponds to a polymer depicted below. Exemplary inventive polymers includes those prepared using polyol units (e.g., xylitol, mannitol, sorbitol, or maltitol) condensed with polycarboxylic acid units (e.g., citric acid, glutaric acid, or sebacic acid). The inventive polymers may be further derivatized or modified. For example, the polymer may be made photo-crosslinkable by adding methacrylate moieties to the polymer.

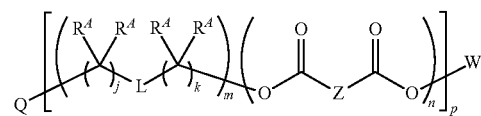

24 Claims, 29 Drawing Sheets

(56) References Cited

U.S. PATENT DOCUMENTS

| | | | |
|---|---|---|---|
| 5,525,646 | A | 6/1996 | Lundgren et al. |
| 5,545,212 | A | 8/1996 | Wakabayashi et al. |
| 5,696,175 | A | 12/1997 | Mikos et al. |
| 5,716,404 | A | 2/1998 | Vacanti et al. |
| 5,736,372 | A | 4/1998 | Vacanti et al. |
| 5,770,417 | A | 6/1998 | Vacanti et al. |
| 5,804,178 | A | 9/1998 | Vacanti et al. |
| 5,837,752 | A | 11/1998 | Shastri et al. |
| 5,902,599 | A | 5/1999 | Anseth et al. |
| 6,017,566 | A | 1/2000 | Bunczek et al. |
| 6,095,148 | A | 8/2000 | Shastri et al. |
| 6,123,727 | A | 9/2000 | Vacanti et al. |
| 6,160,084 | A | 12/2000 | Langer et al. |
| 6,376,742 | B1 | 4/2002 | Zdrahala et al. |
| 6,444,782 | B1 | 9/2002 | Hamlin |
| 6,818,018 | B1 | 11/2004 | Sawhney |
| 7,192,664 | B1 | 3/2007 | Wu et al. |
| 7,722,894 | B2 | 5/2010 | Wang et al. |
| 7,923,486 | B2 | 4/2011 | Yang et al. |
| 8,143,042 | B2 * | 3/2012 | Bettinger et al. ............ 435/180 |
| 2002/0049183 | A1 | 4/2002 | Yedgar et al. |
| 2003/0003125 | A1 | 1/2003 | Nathan et al. |
| 2003/0011105 | A1 | 1/2003 | Kikuchi et al. |
| 2003/0086958 | A1 | 5/2003 | Arnold et al. |
| 2003/0086985 | A1 | 5/2003 | Gupta et al. |
| 2003/0185870 | A1 | 10/2003 | Grinstaff et al. |
| 2004/0006153 | A1 | 1/2004 | Seppala et al. |
| 2004/0019178 | A1 | 1/2004 | Gross et al. |
| 2004/0086479 | A1 | 5/2004 | Grinstaff et al. |
| 2004/0120981 | A1 * | 6/2004 | Nathan ......................... 424/426 |
| 2004/0131582 | A1 | 7/2004 | Grinstaff et al. |
| 2004/0236033 | A1 | 11/2004 | Gloeckner et al. |
| 2004/0253203 | A1 * | 12/2004 | Hossainy et al. .......... 424/78.08 |
| 2005/0019747 | A1 | 1/2005 | Anderson et al. |
| 2005/0048121 | A1 | 3/2005 | East et al. |
| 2005/0063939 | A1 | 3/2005 | Ameer et al. |
| 2007/0243229 | A1 * | 10/2007 | Smith et al. ................... 424/426 |
| 2009/0011486 | A1 | 1/2009 | Bettinger et al. |
| 2009/0047256 | A1 | 2/2009 | Bettinger et al. |
| 2010/0055184 | A1 | 3/2010 | Zeitels et al. |
| 2010/0247600 | A1 | 9/2010 | Xia et al. |
| 2011/0008277 | A1 | 1/2011 | Bruggeman et al. |
| 2012/0269761 | A1 | 10/2012 | Bettinger et al. |

FOREIGN PATENT DOCUMENTS

| | | |
|---|---|---|
| EP | 0 246 341 A1 | 11/1987 |
| EP | 0 427 496 A2 | 5/1991 |
| EP | 0 509 814 A2 | 10/1992 |
| EP | 0 711 506 A2 | 5/1996 |
| EP | 0 786 329 A2 | 7/1997 |
| EP | 0 807 653 A2 | 11/1997 |
| EP | 0 934 918 A1 | 8/1999 |
| EP | 0987284 A1 | 3/2000 |
| EP | 1 038 538 A1 | 9/2000 |
| EP | 1479709 A1 | 11/2004 |
| FR | 2828200 A1 | 2/2003 |
| GB | 2423252 A | 8/2006 |
| JP | 57-170259 A | 10/1982 |
| JP | 5-140870 A | 6/1993 |
| WO | WO-9803528 A1 | 1/1998 |
| WO | WO-98/30617 A1 | 7/1998 |
| WO | WO-98/58010 A1 | 12/1998 |
| WO | WO-00/35297 A1 | 6/2000 |
| WO | WO-01/76554 A2 | 10/2001 |
| WO | WO-03/064496 A2 | 8/2003 |
| WO | WO-2005000939 A1 | 1/2005 |

OTHER PUBLICATIONS

M.Lawson "Sugar Alcohols", Article, Published on Dec. 4, 2000.*

Amsden, et al., In vivo degradable behavior of photo-cross-linked star-poly(e-caprolactoneco-D,L-lactide) elastomers, Biomacromolecules, 7:365-372 (2006).

Amsden, et al., Synthesis and characterization of a photo-cross-linked biodegradable elastomer, Biomacromolecules, 5:2479-2486 (2004).

Anderson, J. M., In vivo Biocompatibility of Implantable Delivery Systems and Biomaterials, Eur. J. Pharm. Biopharm. 40, 1-8 (1994).

Anderson, J., et al., Biodegradation and biocompatibility of PLA and PLGA microspheres, Advanced Drug Delivery Reviews 28: 5-24 (1997).

Anseth, K. S., et al., Photopolymeriable degradable polyanhydrides with osteocompatibility, Nature Biotechnology 17, 156-159 (1999).

Barrera, D., et al., Synthesis and RGD Peptide Modification of a New Biodegradable Copolymer: Poly(lactic acid c-lysine), J. Am. Chem. Soc. 115, 11010-11011 (1993).

Bettinger, C. J. et al., Amino alcohol-based degradable poly(ester amide) elastomers, Biomaterials, 29, (15), 2315-2325 (2008).

Bettinger, C. J. et al., Biocompatibility of biodegradable semiconducting melanin films for nerve tissue engineering, Biomaterials, 30, (17), 3050-3057 (2009).

Bettinger, C. J. et al., In vitro and in vivo degradation of poly(1,3-diamino-2-hydroxypropane-co-polyol sebacate) elastomers, J. Biomed. Mater. Res. A 91(4), 1077-88 (2009).

Borschel, G. H. et al., Mechanical Properties of Acellular Peripheral Nerve, J Surg Res., 114, 133-139 (2003).

Brown, et al., Laryngoscope 114:2021-2024 (2004).

Bruggeman, J. P, et al., Biodegradable Poly(polyol sebacate) Polymers, Biomaterials, 29(36), 4726-4735 (2008).

Bruggeman, J. P., et al., Biodegradable Xylitol-Based Polymers, Adv Mater. 20, 1922-1927 (2008).

Bulpitt and Aeschlimann, New strategy for chemical modification of hyaluronic acid: Preparation of functionalized derivaives and their use in the formation of novel biocompatible hydrogels, J. Biomed. Mater. Re. 47:152-169 (1999).

Burdick, J. A. et al., Controlled Degradation and Mechanical Behavior of Photopolymerized Hyaluronic Acid Networks, Biomacromolecules, 6, 386-391 (2005).

Cadee, J.A., et al., A comparative biocompatibility study of microspheres based on crosslinked dextran or poly(lactic-co-glycolic) acid after subcutaneous injection in rats, J Biomed Mater Res 56, 600-609 (2001).

Calandrelli, L., et al., Preparation and characterisation of composites based on biodegradable polymers for 'in vivo' application, Polymer 41, 8027-8033 (2000).

Cheng et al., A Novel Family of Biodegradable Poly(ester amide) Elastomers, Advanced Materials, 23; H95-H100 (2011).

Clerin, V., et al., Tissue Engineering of Arteries by Directed Remodeling of Intact Arterial Segments, Tissue Eng., 9, (3), 461-472 (2003).

De Groot, J.H., et al., Use of porous polyurethanes for meniscal reconstruction and meniscal prostheses, Biomaterials 17 163-173 (1996).

Den Dunnen, W. F. A.,et al., In vivo and in vitro degradation of poly[50/50(85/15 L/D)LA/ϵ-CL], and the implications for the use in nerve reconstruction, J. Biomed. Mater. Res. A, 51, 575-585 (2000).

Dey et al., Development of Biodegradable Crosslinked Urethane-Doped Polyester Elastomers, Biomaterials, 29(35); 4637-4649 (2008).

Dupont-Gillain, C., et al., Collagen adsorption on poly(methyl methacrylate): net-like structure formation upon drying, Polymer Int 48, 271-276 (1999).

Durairaj, J., et al., Safety assessment of inhaled xylitol in subjects with cystic fibrosis, J Cyst Fibros, 6, (1), 31-34 (2007).

Ellingsworth, L. R., et al., The human immune response to reconstituted bovine collagen, J Immunol, 136, (3), 877-882 (1986).

Elwood, K.C., Methods available to estimate the energy values of sugar alcohols. Am J Clin Nutr, 62 (Suppl), 1169-1174 (1995).

Firoozbakhsh, K., et al., A study of ulnar collateral ligament of the thumb metacarpophalangeal joint, Clin Orthop Relat Res.,403, 240-247 (2002).

Frazl, P., et al., Fibrillar Structure and Mechanical Properties of Collagen, Journal of Structural Biology 122, 119-122 (1997).

Gao, J., et al., Surface hydrolysis of poly(glycolic acid) meshes increases the seeding density of vascular smooth muscle cells, Journal of Biomedical Materials Research 42: 417-424, (1998).

(56) References Cited

OTHER PUBLICATIONS

Gracia, M., et al., Synthesis and Characterization of Linear Polyamides Derived from L-Arabinitol and Xylitol, Macromolecules, 37, 5550-5556 (2004).

Greaves, et al., Macrophage-specific gene expression: current paradigms and future challenges, Int. J. Hemtol. 76(1):6-15, (2002).

Groot, et al., Use of porous polyurethanes for meniscal reconstruction and meniscal prostheses, Biomaterials, 17:163-173 (1996).

Gu, et al., Sustained interferon-y delivery from a photocrosslinked biodegradable elastomer, J. Contr. Release, 102:607-617 (2005).

Guan, et al., Biodegradable poly(ether ester urethane)urea elastomers based on poly(ether ester) triblock copolymers and putrescine: synthesis, characterization and cytocompatibility, Biomaterials, 25(1):85-96 (2004).

Guan, et al., Synthesis, characterization, and cytocompatibility of elastomeric, biodegradable poly(ester-urethane)ureas based on poly(caprolactone) and putrescine, J. Biomed. Mater. Res., 61(3):493-503 (2002).

Ha, S. K., Finite element modeling of multi-level cervical spinal segments (C3-C6) and biomechanical analysis of an elastomer-type prosthetic disc, Med Eng Phys. 28 (6), 534-41 (2006).

Hao, Q., et al., Preparation and crystallization kinetics of new structurally well-defined star-shaped biodegradable poly(L-lactide)s initiated with diverse natural sugar alcohols, Biomacromolecules, 6, (4), 2236-2247 (2005).

Helminen, A. et al., Biodegradable crosslinked polymers based on triethoxysilane terminated polylactice oligomers, Polymer 42, 3345-3353 (2001).

Hennink and Van Nostrum, Novel crosslinking methods to design hydrogels, Advanced Drug Delivery Reviews 54 13-36 (2002).

Henry, E. W. et al., Nerve regeneration through biodegradable polyester tubes, Exp Neurol., 90, 652-676 (1985).

Hern, D. L. et al., Incorporation of adhesion peptides into nonadhesive hydrogels useful for tissue resurfacing. J Biomed Mater Res, 39, 266-276 (1998).

Hjortdal, J. O., Regional Elastic Performance of the Human Cornea. J Biomech, 29, (7), 931-942 (1996).

Honkala, E., et al., Field trial on caries prevention with xylitol candies among disabled school students, Caries Res, 40, (6), 508-513 (2006).

International Search Report for PCT Application PCT/US02/33787.

Jayachandran, K.N., et al., Synthesis of dense brush polymers with cleavable grafts, European Polymer Journal 36, 743-749 (2000).

Joost Bruggeman PhD Thesis.

Kiyotsukuri, et al., Network polyester films from glycerol and dicarboxylic acids, Polymer International, 33(1):1-8 (1994).

Langer, R., Biomaterials: Status, Challenges, and Perspectives, AIChE Journal 46, 1286-1289 (2000).

Laschewsky, A., et al., Tailoring of Stimuli-Responsive Water Soluble Acrylamide and Methacrylamide Polymers, Macromol. Chem. Phys. 202, 276-286 (2001).

Lee, K. Y., et al., Controlling Mechanical and Swelling Properties of Alginate Hydrogels Independently by Cross-Linker Type and Cross-Linking Density, Macromolecules 33, 4291-4294 (2000).

Liu et al., Sythesis, Preparation, in Vitro Degradation, and Application of novel degradable biolestomers—A review, Progress in Polymer Science, 37; 715-765 (2012).

Liu, G., et al., Mechanisms for the Transport of a, co-Dicarboxylates through the Mitochondrial Inner Membrane, The Journal of Biological Chemistry 271, 25338-25344 (1996).

Lupton, J. R., et al., Cutaneous hypersensitivity reaction to injectable hyaluronic acid gel, Dermatol Surg, 26, (2), 135-137 (2000).

Ly, et al., Xylitol, Sweeteners, and Dental Caries, Pediatric Dentistry 28:154-163 (2006).

Mainil-Varlet, P., et al., Long-term soft tissue reaction to various polylactides and their in vivo degradation, J of Materials Science Materials in Medicine, 7, 713-721 (1996).

Malekzadeh, et al., Isolation of human osteoblast-like cells and in vitro amplification for tissue engineering, Journal of Periodontology 69: 1256-1262 (1998) (abstract only).

Mattila, et al., Duetary Xylitol Protects Against Weakening of Bone Biomechanical Properties in Ovariectomized Rats1,2 Journal of Nutrition, 1811-1814 (1998).

Mattila, et al., Improved Bone Biomechanical Properties in Xylitol-Fed Aged Rats, Metabolism 51:92-96 (2002).

Middleton, J. C., et al., Synthetic biodegradable polymers as orthopedic devices, Biomaterials 21, 2335-2346 (2000).

Misof, K., et al., A New Molecular Model for Collagen Elasticity Based on Synchrotron X-Ray Scattering Evidence, Biophysical Journal, 72, 1376-1381 (1997).

Mitsunobu & Yamada, Preparation of esters of carboxylic and phosphoric acid via quaternary phosphonium salts, Bullet. Chem. Soc. Japan, 40(10):2380-2382 (1967).

Motlagh, D., et al., Hemocompatibility evaluation of poly(glycerol-sebacate) in vitro for vascular tissue engineering, Biomaterials, 27, (24), 4315-4324 (2006).

Nagata, M., et al., Synthesis, Characterization, and Enzymatic Degradation of Network Aliphatic Copolyesters, Journal of Polymer Science: Part A: Polymer Chemistry 37: 2005-2011 (1999).

Natah S. S., et. al., Metabolic response to lactitol and xylitol in healthy men1-3, Am. J. Clin. Nutr.65, (4), 947-950 (1997).

Nijst, C. L. E., et al., Synthesis and Characterization of Photocurable Elastomers from Poly(glycerol-co-sebacate), Biomacromolecules, 8, (10), 3067-3073 (2007).

Pego, et al., Biodegradable elastomeric scaffolds for soft tissue engineering, J. Contr. Release, 87:69-79 (2003).

Pego, et al., In vitro degredation of triethylene carbonate based (co)polymers, Macromol. Biosci., 2(9):411-419 (2002).

Pego, et al., in vivo behavior of poly(1,3-trimethylene carbonate and copolymers of 1,3-trimethylenecarbonate with D,L-lactide or ϵ-caprolactone: Degradation and tissue response, J. Biomed. Mater. Res. A., 67(3):1044-54 (2003).

Peppas, N. A., et al., New Challenges in Biomaterials, Science 263, 1715-1720 (1994).

Peppas, N.A., et al., Hydrogels in Biology and Medicine: From Molecular Principles to Bionanotechnology, Adv Mater, 18, 1345-1360 (2006).

Pereira et al., Presentation of Novel Generation of Biodegradable Elastomers with Highly Tunable Mechanical and Degradation Properties, American Chemical Society National Meeting, Boston (Aug. 26, 2010).

Pizzo, et al., Microbiologica 23:63-71 (2000).

Poirier, et al., BioTechnology 13:142-150 (1995).

Rosenblatt, et al., Synthesis of a fragment of human parathyroid hormone, hPTH-(44-68), J. Med. Chem., 20(11):1452-6 (1977).

Rydevik, B. L. et al., An in vitro mechanical and histological study of acute stretching on rabbit tibial nerve, J Orthop Res, 8, (5), 694-701 (1990).

Schmalenberg, K. E., et al., Micropatterned polymer substrates control alignment of proliferating Schwann cells to direct neuronal regeneration, Biomaterials, 26, (12), 1423-1430 (2005).

Semba, C.P., et al., Acute rupture of the descending thoracic oarta: repair with use of endovascular stent-grafts, Journal of Vascular and Interventional Radiology 8: 337-342, (1997) (abstract only).

Sestoft, L., An evaluation of biochemical aspects of intravenous fructose, sorbitol and xylitol administration in man, Acta Anaesthesiol Scand Suppl, 82, 19-29 (1985).

Skrzypiec, D. M. et al., The Internal Mechanical Properties of Cervical Intervertebral Discs as Revealed by Stress Profilometry, Eur Spine J, 16, (10), 1701-1709 (2007).

Smeds, K. A., et al., Photocrosslinkable polysaccharides for in situ hydrogel formation, J Biomed Mater Res, 54, (1), 115-121 (2001).

Sodian, et al., Fabrication of a Trileaflet Heart Valve Scaffold from a Polyhydroxyalkanoate Biopolyester for Use in Tissue Engineering, Tissue Eng. 6:183-187 (2000).

Storey, R. F., et al., Methacrylate-endcapped poly(d,l-lactide-co-trimethylene carbonate) oligomers. Network formation by thermal free-radical curing, Polymer 38, 6295-6301 (1997).

Sundback, et al., Biocompatibility analysis of poly(glycerol sebacate) as a nerve guide material, Biomaterials, 26:5454-64 (2005).

Talke, H., et al., Glucose, fructose, sorbitol and xylitol metabolism in man, Infusionstherapie, 1, (1), 49-56 (1973).

(56) References Cited

OTHER PUBLICATIONS

Tamada, J., et al., Review the development of polyanhydrides for drug delivery applications, J. Biomater Sci. Polymer Edn. 3, 315-353 (1992).
Temenoff, et al., J. Biomed. Mater. Res. 59:429-437 (2002).
Thompson, D. M., et al., Neurite outgrowth is directed by schwann cell alignment in the absence of other guidance cues, Ann Biomed Eng., 34, (1), 161-168 (2006).
Thurston, G., et al. Measurement of cell motility and morphology with an automated microscope system, Cytometry, 9, (5), 411-417 (1988).
Tognana, et al., Adjacent tissues (cartilage, bone) affect the functional integration of engineered calf cartilage in vitro, Osteoarthritis Cartilage, 13, (2), 129-38 (2005).
Uhari, M., et al., Xylitol chewing gum in prevention of acute otitis media: double blind randomised trial, BMJ, 313, 1180-1184 (1996).
Uhari, M., et al., Xylitol in preventing acute otitis media, Vaccine, 19, (Suppl 1), S144-147 (2000).
Van Der Elst, M., et al., Bone tissue response to biodegradable polymers used for intra medullary fracture fixation: A long-term in vivo study in sheep femora, Biomaterials 20, 121-128 (1999).
Van Hest, et al., Protein-based materials, toward a new level of structural control, Chem. Comm. 19:1897-1904 (2001).
Wang, J. L., et al., Failure criterion of collagen fiber: Viscoelastic behavior simulated by using load control data, Theoretical and Applied Fracture Mechanics 27 1-12 (1997).
Wang, Y. et al., A tough biodegradable elastomer. Nat Biotechnol, 20, (6), 602-606 (2002).
Wang, Y., et al., In vivo degradation characteristics of poly(glycerol sebacate), J Biomed Mater Res A, 66, (1), 192-7 (2003).
Welsh, et al., Engineering the Extracellular Matrix: A Novel Approach to Polymeric Biomaterials. I. Control of the Physical Properties of Artificial Protein Matrices Designed to Support Adhesion of Vascular Endothelial Cells, Biomacromolecules 1:23-30 (2000).
West, J. L., et al., Polymeric Biomaterials with Degradation Sites for Proteases Involved in Cell Migration, Macromolecules 32, 241-244 (1999).
Winkelhausen, E., et al., Microbial Conversion of D-Xylose to Xylitol, J Ferment Bioeng, 86, (1), 1-14 (1998).
Yang, J. et al., Novel Citric Acid-Based Biodegradable Elastomers for Tissue Engineering, Adv Mater, 16, (6), 511-516 (2004).
Yang, J. et al., Synthesis and evaluation of poly(diol citrate) biodegradable elastomers, Biomaterials, 27(9):1889-98 (2006).
Zabner, J. et al., The osmolyte xylitol reduces the salt concentration of airway surface liquid and may enhance bacterial killing, Proc Natl Acad Sci U S A., 97, (21), 11614-11619 (2000).
Database WPI Week 197907 Thomson Scientific London, GB; AN 1979-12592B & JP 54000093 A (Toa Gosei Chem Ind Ltd), Jan. 1, 1979.
International Search Report of PCT/US2008/063900, 3 pages (mailed Jan. 13, 2009).

\* cited by examiner

A

B

A

B

A

A

Stoichiometric ratios of (1) and (2)

| | | | | |
|---|---|---|---|---|
| 1 | : | 1 | →  | PXS 1:1 |
| 2 | : | 3 | ⇢ | PXS 2:3 |
| 1 | : | 2 | → | PXS 1:2 |

B

PXS 1:1 pre-polymer
PXS 1:1/1:2 50/50 pre-polymer
PXS 2:3 pre-polymer
PXS 1:2 pre-polymer

Exemplary Acrylated Polymers

PXCma

PXSa

Exemplary linkage groups (A and B) formed via polymerization of acrylate groups present in an inventive polymer:

A

B

Acrylation can be used to covalently bind biological active structures (peptides/proteins) containing a cysteine to the polymer backbone. For example:

Scheme of dihydrazide crosslinking. (In situ cross-linking requires prior mixing of the two batches in tissue, followed by cross-linking).

Mixing of the two batches:

Exemplary reaction between PXC-ADH and a modified NHS-ester:

POLYOL-BASED POLYMERS

STATEMENT OF GOVERNMENT SUPPORT

This invention was made with government support under Grant No. MCB0509923 awarded by the National Science Foundation. The government has certain rights in this invention.

RELATED APPLICATIONS

The present application claims priority under 35 U.S.C. §119(e) to U.S. provisional patent application, U.S. Ser. No. 60/930,606, filed May 17, 2007, which is incorporated herein by reference.

BACKGROUND OF THE INVENTION

Synthetic biodegradable polymers have significant potential in various fields of bioengineering, such as tissue engineering and drug delivery. Synthetic biodegradable polymers are used as components in a variety of biomedical devices, such as, for example, implants, pacemakers, heart valves, artificial joints, tubing, shunts, dialyzers, oxygenators, dental materials, tablet coatings, drug delivery devices, sutures, staples, adhesives, and the like. The design of these biomaterials is challenging because of the application-specific requirements on the physical and chemical properties of the biomaterials, including mechanical compliance, strength, degradation, biocompatibility, etc. For example, synthetic biodegradable polymers that are designed as replacements for soft and hard tissues must sustain and recover from various stressors and deformations. Ideally, the material should resemble the mechanical properties of the tissues found at the implantation site to prevent mechanical irritation and not compromise the structural integrity of target tissues and organs. Biodegradable polymers whose properties resemble that of the extracellular matrix, a soft, tough, and elastomeric proteinaceous network, provide the best mechanical stability and structural integrity to tissues and organs. To date, such elastomeric biomaterials include hydrogels (for example, Lee et al., *Macromolecules* (2000) 33:4291-4294; Temenoff et al., *J. Biomed. Mater. Res.* (2002) 59:429-437), elastin-like peptides (for example, van Hest et al., *Chem. Comm.* (2001) 19:1897-1904; Welsh et al., *Biomacromolecules* (2000) 1:23-30), polyhydroxyalkanoates (PHAs) (for example, Poirier et al., *BioTechnology* (1995) 13:142-150; Sodian et al., *Tissue Eng.* (2000) 6:183-187), and tough biodegradable elastomers such as poly(diol-citrate) (PDC), poly(glycerol-sebacate) (PGS), poly(D,L-lactide-co-ε-caprolactone), and poly(ε-caprolactone).

There remains a need in the art for synthetic biodegradable polymers with a wide range of chemical and physical properties for use in bioengineering.

SUMMARY OF THE INVENTION

The present invention describes a platform for preparing synthetic polyol-based polymers, ranging from hydrogels to hydrogel elastomers to tough elastomers. These polyol-based polymers are typically biodegradable. These polymers may have one or more of the following characteristics: (1) multifunctional to allow the formation of randomly crosslinked networks and a wide range of crosslinking densities; (2) non-toxic; (3) components (e.g., monomers or degradation products) that are endogenous to the human metabolic system; (4) approved by the U.S. FDA or other governmental regulatory office; and (5) inexpensive to prepare. In certain embodiments, the inventive synthetic polyol-based polymer is based on xylitol. The inventive polymers may be further processed (e.g., cross-linking, derivatization) to prepare novel materials.

Specifically, the present invention provides novel polymers from condensing and/or cross-linking polyols with polycarboxylic acids and further materials produced from these polymers. The inventive polymers may be linear or branched polymers. The polymers are, in certain embodiments, biodegradable and/or biocompatible. Typically, the polyol-based polymers are of the formula:

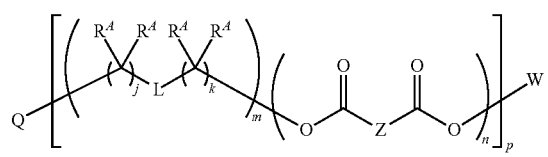

wherein Q, L, Z, W, $R^A$, j, k, m, n, or p are as defined herein. In certain embodiments, the polymer is of the formula:

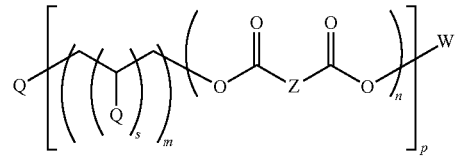

wherein Q, Z, W, s, m, n, or p are as defined herein. In certain embodiments, the polymer is based on the polyol, xylitol, sorbitol, mannitol, or maltitol. In certain embodiments, the polyol is polymerized with a dicarboxylic acid such as sebacic acid.

The invention provides methods of preparing the inventive polymers and materials as well as various methods of using the inventive polymers and materials. The invention also provides pharmaceutical compositions comprising an inventive polymer or material, and a biologically active agent.

The present invention provides inventive polyol-based polymers which may have one or more of the following characteristics: (1) the inventive polymer is made from naturally occurring monomers; (2) the inventive polymer is biodegradable; (3) the inventive polymer is composed of biocompatible monomers (e.g., the pharmacokinetics and pharmacodynamics of the monomers are characterized, and found non-toxic, in humans or animals; and/or be approved by the U.S. Food and Drug Administration as safe for use in humans or medical applications); (4) one or more, or all, of the components of the in vivo degraded polymer is endogenous to the human metabolic system, (5) the inventive polymer is inexpensive to make (e.g., the polymerization to provide the inventive polymer can be achieved without the use of solvents; the production of the monomers and the inventive polymer can easily be scaled up; the inventive polymer is synthesized rapidly (e.g., rapid polymerization)); (6) the inventive polymer is prepared without using harsh solvents, reagents, and/or conditions (e.g., "neat" reaction mixtures; room temperature polymerization, low temperature polymerization); (7) the inventive polymer can be polymerized in situ (e.g., in vivo); (8) the inventive polymer is a hydrogel; (9) the inventive polymer is an elastomer; (10) the inventive polymer is transparent; (11) the inventive polymer maintains a high level of surface- and/or bulk-functionality (e.g., exposed and/ or unprotected hydroxyl and carboxylate functional groups); (12) the inventive polymer comprises an intra-network of hydrogen bonding; (13) the inventive polymer permits encapsulation of biologically active agents; (14) the inventive polymer has protein/cell adhesion properties; (15) the inventive polymer is injectable; and/or (16) the inventive polymer is easily modifiable, and can be used as a platform for the fabrication of other novel materials with unique mechanical properties. The inventive polymers may be further modified to form new materials. In certain embodiments, the polymer is cross-linked. In certain embodiments, the polymer is derivatized. For example, free hydroxyl groups may be further modified by reaction with a suitable electrophile (e.g., anhydride, ester, acrylate, methacrylate). The materials prepared from the polyol-based polymers may be hydrogels or elastomers.

DEFINITIONS

Chemical Terminology

Definitions of specific functional groups and chemical terms are described in more detail below. For purposes of this invention, the chemical elements are identified in accordance with the Periodic Table of the Elements, CAS version, *Handbook of Chemistry and Physics*, 75$^{th}$ Ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito, 1999; Smith and March *March's Advanced Organic Chemistry*, 5$^{th}$ Edition, John Wiley & Sons, Inc., New York, 2001; Larock, *Comprehensive Organic Transformations*, VCH Publishers, Inc., New York, 1989; Carruthers, *Some Modern Methods of Organic Synthesis*, 3$^{rd}$ Edition, Cambridge University Press, Cambridge, 1987; the entire contents of each of which are incorporated herein by reference.

The inventive polymers of the present invention may exist in particular geometric or stereoisomeric forms. The present invention contemplates all such polymers, including cis- and trans-isomers, R- and S-enantiomers, diastereomers, (D)-isomers, (L)-isomers, the racemic mixtures thereof, and other mixtures thereof, as falling within the scope of the invention.

Where an isomer/enantiomer is preferred, it may, in some embodiments be provided substantially free of the corresponding enantiomer, and may also be referred to as "optically enriched." "Optically-enriched," as used herein, means that the inventive polymer, or polyol or polycarboxylic acid used to make the inventive polymer, is made up of a significantly greater proportion of one enantiomer. In certain embodiments the inventive polymer, or polyol or polycarboxylic acid, is made up of at least about 90% by weight of a preferred enantiomer. In other embodiments the inventive polymer, or polyol or polycarboxylic acid, is made up of at least about 95%, 98%, or 99% by weight of a preferred enantiomer. Preferred enantiomers may be isolated from racemic mixtures by any method known to those skilled in the art, including chiral high pressure liquid chromatography (HPLC) and the formation and crystallization of chiral salts or prepared by asymmetric syntheses. See, for example, Jacques, et al., *Enantiomers, Racemates and Resolutions* (Wiley Interscience, New York, 1981); Wilen, S. H., et al., *Tetrahedron* 33:2725 (1977); Eliel, E. L. *Stereochemistry of Carbon Compounds* (McGraw-Hill, NY, 1962); Wilen, S. H. *Tables of Resolving Agents and Optical Resolutions*, p. 268 (E. L. Eliel, Ed., Univ. of Notre Dame Press, Notre Dame, Ind. 1972).

It will be appreciated that the inventive polymer, or polyol or polycarboxylic acid used to make the inventive polymer, as described herein, may be substituted with any number of substituents or functional moieties. In general, the term "substituted" whether preceded by the term "optionally" or not, and substituents contained in formulas of this invention, refer to the replacement of hydrogen radicals in a given structure with the radical of a specified substituent. When more than one position in any given structure may be substituted with more than one substituent selected from a specified group, the substituent may be either the same or different at every position. As used herein, the term "substituted" is contemplated to include all permissible substituents of organic compounds. In a broad aspect, the permissible substituents include acyclic and cyclic, branched and unbranched, carbocyclic and heterocyclic, aromatic and nonaromatic substituents of organic compounds. For purposes of this invention, heteroatoms such as nitrogen may have hydrogen substituents and/or any permissible substituents of organic compounds described herein which satisfy the valencies of the heteroatoms. Furthermore, this invention is not intended to be limited in any manner by the permissible substituents of organic compounds.

In certain aspects, the term "substituted" is also contemplated to include substitution with a "biologically-active agent," or substitution with another inventive polymer, as defined herein.

The term "aliphatic," as used herein, includes both saturated and unsaturated, nonaromatic, straight chain (i.e., unbranched), branched, acyclic, cyclic (i.e., carbocyclic), or polycyclic hydrocarbons, which are optionally substituted with one or more functional groups. As will be appreciated by one of ordinary skill in the art, "aliphatic" is intended herein to include, but is not limited to, alkyl, alkenyl, alkynyl, cycloalkyl, cycloalkenyl, and cycloalkynyl moieties. Thus, as used herein, the term "alkyl" includes straight, branched and cyclic alkyl groups. An analogous convention applies to other generic terms such as "alkenyl", "alkynyl", and the like. Furthermore, as used herein, the terms "alkyl", "alkenyl", "alkynyl", and the like encompass both substituted and unsubstituted groups. In certain embodiments, as used herein, "aliphatic" is used to indicate those aliphatic groups (cyclic, acyclic, substituted, unsubstituted, branched or unbranched) having 1-20 carbon atoms. Aliphatic group substituents include, but are not limited to, any of the substituents described herein, that result in the formation of a stable moiety (for example, an aliphatic group substituted with one or more aliphatic, alkyl, alkenyl, alkynyl, heteroaliphatic, heterocyclic, aryl, heteroaryl, acyl, sulfinyl, sulfonyl, oxo, imino, thiooxo, phosphino, cyano, amino, azido, nitro, hydroxy, thio, and/or halo groups).

The term "stable moiety," as used herein, preferably refers to a moiety which possess stability sufficient to allow manufacture, and which maintains its integrity for a sufficient period of time to be useful for the purposes detailed herein.

The term "heteroaliphatic," as used herein, refers to an aliphatic moiety, as defined herein, that contain one or more oxygen, sulfur, nitrogen, phosphorus, or silicon atoms, e.g., in place of carbon atoms. In certain embodiments, heteroaliphatic moieties are substituted by independent replacement of one or more of the hydrogen atoms thereon with one or more substituents. Heteroaliphatic group substituents include, but are not limited to, any of the substituents described herein, that result in the formation of a stable moiety (for example, a heteroaliphatic group substituted with one or more aliphatic, alkyl, alkenyl, alkynyl, heteroaliphatic, heterocyclic, aryl, heteroaryl, acyl, sulfinyl, sulfonyl, oxo, imino, thiooxo, cyano, amino, azido, nitro, hydroxy, thio, and/or halo groups).

The term "alkyl," as used herein, refers to saturated, straight- or branched-chain hydrocarbon radicals derived from a hydrocarbon moiety containing between one and twenty carbon atoms by removal of a single hydrogen atom. In some embodiments, the alkyl group employed in the invention contains 1-20 carbon atoms. In another embodiment, the alkyl group employed contains 1-12 carbon atoms. In still other embodiments, the alkyl group contains 1-6 carbon atoms. In yet another embodiments, the alkyl group contains 1-4 carbons. Examples of alkyl radicals include, but are not limited to, methyl, ethyl, n-propyl, isopropyl, n-butyl, iso-butyl, sec-butyl, sec-pentyl, iso-pentyl, tert-butyl, n-pentyl, neopentyl, n-hexyl, sec-hexyl, n-heptyl, n-octyl, n-decyl, n-undecyl, dodecyl, and the like, which may bear one or more substitutents. Alkyl group substituents include, but are not limited to, any of the substituents described herein, that result in the formation of a stable moiety (for example, an alkyl group substituted with one or more aliphatic, heteroaliphatic, heterocyclic, aryl, heteroaryl, acyl, sulfinyl, sulfonyl, oxo, imino, thiooxo, cyano, amino, azido, nitro, hydroxy, thio, and/or halo groups).

The term "alkenyl," as used herein, denotes a monovalent group derived from a straight- or branched-chain hydrocarbon moiety having at least one carbon-carbon double bond by the removal of a single hydrogen atom. In certain embodiments, the alkenyl group employed in the invention contains 2-20 carbon atoms. In some embodiments, the alkenyl group employed in the invention contains 2-10 carbon atoms. In another embodiment, the alkenyl group employed contains 2-8 carbon atoms. In still other embodiments, the alkenyl group contains 2-6 carbon atoms. In yet another embodiments, the alkenyl group contains 2-4 carbons. Alkenyl groups include, for example, ethenyl, propenyl, butenyl, 1-methyl-2-buten-1-yl, and the like, which may bear one or more substituents. Alkenyl group substituents include, but are not limited to, any of the substituents described herein, that result in the formation of a stable moiety (for example, an alkenyl group substituted with one or more aliphatic, heteroaliphatic, heterocyclic, aryl, heteroaryl, acyl, sulfinyl, sulfonyl, oxo, imino, thiooxo, cyano, amino, azido, nitro, hydroxy, thio, and/or halo groups).

The term "alkynyl," as used herein, refers to a monovalent group derived from a straight- or branched-chain hydrocarbon having at least one carbon-carbon triple bond by the removal of a single hydrogen atom. In certain embodiments, the alkynyl group employed in the invention contains 2-20 carbon atoms. In some embodiments, the alkynyl group employed in the invention contains 2-10 carbon atoms. In another embodiment, the alkynyl group employed contains 2-8 carbon atoms. In still other embodiments, the alkynyl group contains 2-6 carbon atoms. In still other embodiments, the alkynyl group contains 2-4 carbon atoms. Representative alkynyl groups include, but are not limited to, ethynyl, 2-propynyl(propargyl), 1-propynyl, and the like, which may bear one or more substituents. Alkynyl group substituents include, but are not limited to, any of the substituents described herein, that result in the formation of a stable moiety (for example, an alkynyl group substituted with one or more aliphatic, heteroaliphatic, heterocyclic, aryl, heteroaryl, acyl, sulfinyl, sulfonyl, oxo, imino, thiooxo, cyano, amino, azido, nitro, hydroxy, thio, and/or halo groups).

The term "alkylene," as used herein, refers to a fully saturated straight- or branched-chain alkyl biradical containing between one and twenty carbon atoms by removal of two hydrogen atoms (the term alkyl is defined herein). In certain embodiments, an alkylene group is substituted by independent replacement of one or more of the hydrogen atoms thereon with one or more substituents. Alkylene group substituents include but are not limited to any of the substituents described herein that result in the formation of a stable moiety (such as, for example, an alkylene group substituted with one or more aliphatic, heteroaliphatic, heterocyclic, aryl, heteroaryl, acyl, sulfinyl, sulfonyl, cyano, amino, azido, nitro, hydroxyl, thiol, and/or halo groups).

The term "alkenylene," as used herein, refers to a straight- or branched-chain alkenyl biradical containing between two and twenty carbon atoms by removal of two hydrogen atoms (the term alkenyl is defined herein). In certain embodiments, an alkenylene group is substituted by independent replacement of one or more of the hydrogen atoms thereon with one or more substituents. Alkenylene group substituents include but are not limited to any of the substituents described herein that result in the formation of a stable moiety (such as, for example, an alkenylene group substituted with one or more aliphatic, heteroaliphatic, heterocyclic, aryl, heteroaryl, acyl, sulfinyl, sulfonyl, oxo, imino, thiooxo, cyano, amino, azido, nitro, hydroxyl, thiol, and/or halo groups).

The term "alkynylene" as used herein, refers to a straight- or branched-chain alkynyl biradical containing between two and twenty carbon atoms by removal of two hydrogen atoms (the term alkynyl is defined herein). In certain embodiments, an alkynylene group is substituted by independent replacement of one or more of the hydrogen atoms thereon with one or more substituents. Alkynylene group substituents include but are not limited to any of the substituents described herein that result in the formation of a stable moiety (such as, for example, an alkynylene group substituted with one or more aliphatic, heteroaliphatic, heterocyclic, aryl, heteroaryl, acyl, sulfinyl, sulfonyl, oxo, imino, thiooxo, cyano, amino, azido, nitro, hydroxyl, thiol, and/or halo groups).

The term "heteroalkylene," as used herein, refers to an alkylene group, as defined herein, that contains one or more oxygen, sulfur, nitrogen, phosphorus, or silicon atoms, e.g., in place of carbon atoms.

The term "heteroalkenylene," as used herein, refers to an alkenylene group, as defined herein, that contains one or more oxygen, sulfur, nitrogen, phosphorus, or silicon atoms, e.g., in place of carbon atoms.

The term "heteroalkynylene," as used herein, refers to an alkynylene group, as defined herein, that contains one or more oxygen, sulfur, nitrogen, phosphorus, or silicon atoms, e.g., in place of carbon atoms.

The term "heterocyclic," or "heterocyclyl," as used herein, refers to an non-aromatic, partially unsaturated or fully saturated, 3- to 10-membered ring system, which includes single rings of 3 to 8 atoms in size, and bi- and tri-cyclic ring systems which may include aromatic five- or six-membered aryl or heteroaryl groups fused to a non-aromatic ring. These heterocyclic rings include those having from one to three heteroatoms independently selected from oxygen, sulfur, and nitrogen, in which the nitrogen and sulfur heteroatoms may optionally be oxidized and the nitrogen heteroatom may optionally be quaternized. In certain embodiments, the term heterocylic refers to a non-aromatic 5-, 6-, or 7-membered ring or polycyclic group wherein at least one ring atom is a heteroatom selected from O, S, and N (wherein the nitrogen and sulfur heteroatoms may be optionally oxidized), and the remaining ring atoms are carbon, the radical being joined to the rest of the molecule via any of the ring atoms. Heterocycyl groups include, but are not limited to, a bi- or tri-cyclic group, comprising fused five, six, or seven-membered rings having between one and three heteroatoms independently selected from the oxygen, sulfur, and nitrogen, wherein (i) each 5-membered ring has 0 to 2 double bonds, each 6-membered ring has 0 to 2 double bonds, and each 7-membered ring has 0 to 3 double bonds, (ii) the nitrogen and sulfur heteroatoms may be optionally oxidized, (iii) the nitrogen heteroatom may optionally be quaternized, and (iv) any of the above heterocyclic rings may be fused to an aryl or heteroaryl ring. Exemplary heterocycles include azacyclopropanyl, azacyclobutanyl, 1,3-diazatidinyl, piperidinyl, piperazinyl, azocanyl, thiaranyl, thietanyl, tetrahydrothiophenyl, dithiolanyl, thiacyclohexanyl, oxiranyl, oxetanyl, tetrahydrofuranyl, tetrahydropuranyl, dioxanyl, oxathiolanyl, morpholinyl, thioxanyl, tetrahydronaphthyl, and the like, which may bear one or more substituents. Substituents include, but are not limited to, any of the substituents described herein, that result in the formation of a stable moiety (for example, a heterocyclic group substituted with one or more aliphatic, heteroaliphatic, heterocyclic, aryl, heteroaryl, acyl, sulfinyl, sulfonyl, oxo, imino, thiooxo, cyano, amino, azido, nitro, hydroxy, thio, and/or halo groups).

The term "aryl," as used herein, refer to stable aromatic mono- or polycyclic ring system having 3-20 ring atoms, of which all the ring atoms are carbon, and which may be substituted or unsubstituted. In certain embodiments of the present invention, "aryl" refers to a mono, bi, or tricyclic $C_4$-$C_{20}$ aromatic ring system having one, two, or three aromatic rings which include, but not limited to, phenyl, biphenyl, naphthyl, and the like, which may bear one or more substituents. Aryl substituents include, but are not limited to, any of the substituents described herein, that result in the formation of a stable moiety (for example, an aryl group substituted with one or more aliphatic, heteroaliphatic, heterocyclic, aryl, heteroaryl, acyl, sulfinyl, sulfonyl, oxo, imino, thiooxo, cyano, amino, azido, nitro, hydroxy, thio, and/or halo groups).

The term "heteroaryl," as used herein, refer to stable aromatic mono- or polycyclic ring system having 3-20 ring atoms, of which one ring atom is selected from S, O, and N; zero, one, or two ring atoms are additional heteroatoms independently selected from S, O, and N; and the remaining ring atoms are carbon, the radical being joined to the rest of the molecule via any of the ring atoms. Exemplary heteroaryls include, but are not limited to pyrrolyl, pyrazolyl, imidazolyl, pyridinyl, pyrimidinyl, pyrazinyl, pyridazinyl, triazinyl, tetrazinyl, pyrrolizinyl, indolyl, quinolinyl, isoquinolinyl, benzoimidazolyl, indazolyl, quinolinyl, isoquinolinyl, quinolizinyl, cinnolinyl, quinazolinyl, phthalazinyl, naphthridinyl, quinoxalinyl, thiophenyl, thianaphthenyl, furanyl, benzofuranyl, benzothiazolyl, thiazolynyl, isothiazolyl, thiadiazolynyl, oxazolyl, isoxazolyl, oxadiaziolyl, oxadiaziolyl, and the like, which may bear one or more substituents. Heteroaryl substituents include, but are not limited to, any of the substituents described herein, that result in the formation of a stable moiety (for example, a heteroaryl group substituted with one or more aliphatic, heteroaliphatic, heterocyclic, aryl, heteroaryl, acyl, sulfinyl, sulfonyl, oxo, imino, thiooxo, cyano, amino, azido, nitro, hydroxy, thio, and/or halo groups).

The term "acyl," as used herein, refers to a group having the general formula —C(=O)R, where R is hydrogen, halogen, hydroxyl, thiol, optionally substituted amino, optionally substituted hydrazino, optionally substituted aliphatic, optionally substituted heteroaliphatic, optionally substituted alkyl, optionally substituted alkenyl, optionally substituted alkynyl, optionally substituted aryl, alkyloxy, alkylthioxy, alkylamino, dialkylamino, arylamino, diarylamino, optionally substituted aryl, optionally substituted heteroaryl, or optionally substituted heterocycyl. Exemplary acyl groups include aldehydes (—CHO), carboxylic acids (—CO$_2$H), ketones (such as an acetyl group [—(C=O)CH$_3$], esters, amides, carbonates, carbamates, and ureas. Acyl substituents include, but are not limited to, any of the substituents described herein, that result in the formation of a stable moiety (for example, a heteroaryl group substituted with one or more aliphatic, alkyl, alkenyl, alkynyl, heteroaliphatic, heterocyclic, aryl, heteroaryl, acyl, sulfinyl, sulfonyl, oxo, imino, thiooxo, cyano, amino, azido, nitro, hydroxy, thio, and/or halo groups).

A "suitable carboxylic acid protecting group," or "protected carboxylic acid," as used herein, are well known in the art and include those described in detail in Greene (1999). Examples of suitably protected carboxylic acids further include, but are not limited to, silyl-, alkyl-, alkenyl-, aryl-, and arylalkyl-protected carboxylic acids. Examples of suitable silyl groups include trimethylsilyl, triethylsilyl, t-butyldimethylsilyl, t-butyldiphenylsilyl, triisopropylsilyl, and the like. Examples of suitable alkyl groups include methyl, benzyl, p-methoxybenzyl, 3,4-dimethoxybenzyl, trityl, t-butyl, tetrahydropyran-2-yl. Examples of suitable alkenyl groups include allyl. Examples of suitable aryl groups include optionally substituted phenyl, biphenyl, or naphthyl. Examples of suitable arylalkyl groups include optionally substituted benzyl (e.g., p-methoxybenzyl (MPM), 3,4-dimethoxybenzyl, O-nitrobenzyl, p-nitrobenzyl, p-halobenzyl, 2,6-dichlorobenzyl, p-cyanobenzyl), and 2- and 4-picolyl.

An "activated carboxylic acid," as used herein, includes esters, anhydrides, acyl halides, sulfonylated carboxylic acids (e.g., —C(O)O-trifluoromethylsulfonyl (—OTf), —C(O)O-tolylsulfonyl (—OTs), —C(O)O-methanesulfonyl (—OMs), —C(O)O-(4-nitrophenylsulfonyl) (—ONos), and —C(O)O-(2-nitrophenylsulfonyl) (—ONs)), and the like.

The term "acylene," "acyl linkage," or "bridging acyl linkage," or "bridging acyl group," as used herein, refers to an acyl group having the general formulae: —R$^a$—(C=X)—R$^a$—, —R$^a$—X$^2$(C=X$^1$)—R$^a$—, or —R$^a$—X$^2$(C=X$^1$)X$^3$—R$^a$—, where X$^1$, X$^2$, and X$^3$ is, independently, oxygen, sulfur, or NR″, wherein R″ is any substitutent, including hydrogen, which results in a stable moiety, and R$^a$ is an optionally substituted alkylene, alkenylene, alkynylene, heteroalkylene, heteroalkenylene, or heteroalkynylene group, as defined above and herein. Exemplary bridging acyl groups include —(C=O)—O-(aliphatic)-NR″NR″—(aliphatic)-NR″-NR″—(C=O)—; —(C=O)-(aliphatic)-NR″NR″-(aliphatic)-NR″NR″—(C=O)—; -(aliphatic)-(C=O)—O-(aliphatic)-NR″NR″-(aliphatic)-NR″NR″—(C=O)—; -(aliphatic)-(C=O)-(aliphatic)-NR″R″—(aliphatic)-NR″-NR″—(C=O)—; -(aliphatic)-O(C=O)-(aliphatic)-; -(aliphatic)-NR″(C=O)-(aliphatic)-; -(aliphatic)-O(C=NR″)-(aliphatic)-; -(aliphatic)-NR″(C=NR″)-(aliphatic)-; -(aliphatic)-(C=O)-(aliphatic)-; -(aliphatic)-(C=NR″)-(aliphatic)-; -(aliphatic)-S(C=S)-(aliphatic)-; -(aliphatic)-NR″(C=S)-(aliphatic)-; -(aliphatic)-S(C=NR″)-(aliphatic)-; -(aliphatic)-O(C=S)-(aliphatic)-; -(aliphatic)-(C=S)-(aliphatic)-; or -(aliphatic)-S(C=O)-(aliphatic)-, and the like, which may bear one or more substituents.

The term "arylene," as used herein refers to an aryl biradical derived from an aryl group by removal of two hydrogen atoms. The term "heteroarylene," as used herein refers to a heteroaryl biradical derived from a heteroaryl group by removal of two hydrogen atoms. Arylene and heteroarylene groups may be substituted or unsubstituted. Additionally, arylene and heteroarylene groups may be incorporated as a linker group into an alkylene, alkenylene, alkynylene, heteroalkylene, heteroalkenylene, or heteroalkynylene group. For example, an arylene or heteroarylene further incorporated into an alkylene group may correspond to the formula —(CH$_2$)$_c$-(arylene or heteroarylene group)-(CH$_2$)$_d$—, wherein c and d are, independently, an integer between 0 to 20. In certain embodiments, c and d are 0. In certain embodiments, c and d are 1.

An "acrylate group," or an "acrylate moiety," as used herein, is an acyl group of the formula: —C(═O)C(R$^e$)═C(R$^f$)$_2$, wherein R$^e$ and R$^f$ are, independently, any substituent which results in a stable acrylate moiety, such as, for example, hydrogen, aliphatic, aryl, heteroaryl, heterocyclyl, or halogen. An "acrylate group," as defined above, comprises "methacrylate," wherein R$^e$ is —CH$_3$ and each R$^f$ is hydrogen.

The term "sulfinyl," as used herein, refers to a group of the formula R$^g$—S(═O)— where there is one double bond between the sulfur and oxygen, and where R$^g$ may be an optionally substituted aliphatic, aryl, hydroxy, thiol, amino, aryl, heteroaryl, or heterocyclyl. The term "aliphaticsulfinyl" refers to a sulfinyl group where R$^g$ may be an optionally substituted aliphatic, heterocyclyl, or heteroaliphatic. The term "arylsulfinyl" refers to a sulfinyl group where R may be an optionally substituted aryl or heteroaryl.

The term "sulfonyl," as used herein, refers to an organic radical (or functional group) obtained from an sulfonic acid by the removal of the hydroxyl group. Sulfonyl groups can be written as having the general formula R$^g$—S(═O)$_2$—, where there are two double bonds between the sulfur and oxygen, and where R$^g$ may be an optionally substituted aliphatic, heteroaliphatic, aryl, hydroxy, thiol, amino, aryl, heteroaryl, or heterocyclic. The term "aliphaticsulfonyl" refers to a sulfonyl group where R$^g$ may be an optionally substituted aliphatic, heteroaliphatic, or heterocyclic. The term "alkylsulfonyl" refers to a sulfonyl group where R$^g$ may be an optionally substituted alkyl. The term "arylsulfonyl" refers to a sulfonyl group where R$^g$ may be an optionally substituted aryl or heteroaryl. Exemplary aryl or alkyl sulfonyl groups include tosyl (toluene sulfonyl, CH$_3$C$_6$H$_4$SO$_2$—), mesyl (methyl sulfonyl, CH$_3$SO$_2$—), and trifluoromethanesulfonyl (CF$_3$SO$_2$—).

The term "amino," as used herein, refers to a group of the formula (—NH$_2$). An "optionally substituted amino" refers to a group of the formula (—NR$^h$$_2$), wherein R$^h$ can be hydrogen, or any substitutent. Substituents include, but are not limited to, any of the substituents described herein, that result in the formation of a stable moiety (for example, an amino group substituted with one or more aliphatic, alkyl, alkenyl, alkynyl, heteroaliphatic, heterocyclic, aryl, heteroaryl, acyl, sulfinyl, sulfonyl, amino, nitro, hydroxy, and/or thio groups).

A "suitable amino-protecting group," as used herein, is well known in the art and include those described in detail in *Protecting Groups in Organic Synthesis*, T. W. Greene and P. G. M. Wuts, 3$^{rd}$ edition, John Wiley & Sons, 1999, the entirety of which is incorporated herein by reference. Suitable amino-protecting groups include methyl carbamate, ethyl carbamate, 9-fluorenylmethyl carbamate (Fmoc), 9-(2-sulfo)fluorenylmethyl carbamate, 9-(2,7-dibromo)fluoroenylmethyl carbamate, 2,7-di-t-butyl-[9-(10,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl)ethyl carbamate (Pyoc), 2-(N,N-dicyclohexylcarboxamido)ethyl carbamate, t-butyl carbamate (BOC), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitrobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl) ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, phenothiazinyl-(10)-carbonyl derivative, N'-p-toluenesulfonylaminocarbonyl derivative, N'-phenylaminothiocarbonyl derivative, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxycarbonylvinyl carbamate, o-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isobornyl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo)benzyl carbamate, 2,4,6-tri-t-butylphenyl carbamate, 4-(trimethylammonium)benzyl carbamate, 2,4,6-trimethylbenzyl carbamate, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitrophenylacetamide, o-nitrophenoxyacetamide, acetoacetamide, (N'-dithiobenzyloxycarbonylamino)acetamide, 3-(p-hydroxyphenyl)propanamide, 3-(o-nitrophenyl)propanamide, 2-methyl-2-(o-nitrophenoxy)propanamide, 2-methyl-2-(o-phenylazophenoxy)propanamide, 4-chlorobutanamide, 3-methyl-3-nitrobutanamide, o-nitrocinnamide, N-acetylmethionine derivative, o-nitrobenzamide, o-(benzoyloxymethyl)benzamide, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyrrolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N—(N',N'-dimethylaminomethylene)amine, N,N'-isopropylidenediamine, N-p-nitrobenzylideneamine, N-salicylideneamine, N-5-chlorosalicylideneamine, N-(5-chloro-2-hydroxyphenyl)phenylmethyleneamine, N-cyclohexylideneamine, N-(5,5-dimethyl-3-oxo-1-cyclohexenyl) amine, N-borane derivative, N-diphenylborinic acid derivative, N-[phenyl(pentacarbonylchromium- or tungsten) carbonyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, 3-nitropyridinesulfenamide (Npys), p-toluenesulfonamide (Ts), benzenesulfonamide, 2,3,6,-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), β-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide.

The term "hydroxy," or "hydroxyl," as used herein, refers to a group of the formula (—OH). An "optionally substituted hydroxy" refers to a group of the formula (—OR$^i$), wherein R$^i$ can be hydrogen, or any substitutent which results in a stable moiety (for example, a hydroxy group substituted with a suitable hydroxyl protecting group, an aliphatic, alkyl, alkenyl, alkynyl, heteroaliphatic, heterocyclic, aryl, heteroaryl, acyl, sulfinyl, and/or sulfonyl group).

An "activated" hydroxyl group, as used herein, includes sulfonyl groups (e.g., O-trifluoromethylsulfonyl (—OTf), O-tolylsulfonyl (—OTs), O-methanesulfonyl (—OMs), O-(4-nitrophenylsulfonyl) (—ONos), and O-(2-nitrophenylsulfonyl) (—ONs)), and acyl groups.

A "suitable hydroxyl protecting group" as used herein, is well known in the art and include those described in detail in *Protecting Groups in Organic Synthesis*, T. W. Greene and P. G. M. Wuts, 3$^{rd}$ edition, John Wiley & Sons, 1999, the entirety of which is incorporated herein by reference. Suitable hydroxyl protecting groups include methyl, methoxylmethyl (MOM), methylthiomethyl (MTM), t-butylthiomethyl, (phenyldimethylsilyl)methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl)ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl, p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxido, diphenylmethyl, p,p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4''-tris(4,5-dichlorophthalimidophenyl)methyl, 4,4',4''-tris(levulinoyloxyphenyl)methyl, 4,4',4''-tris(benzoyloxyphenyl)methyl, 3-(imidazol-1-yl)bis(4',4''-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodithiolan-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), alkyl methyl carbonate, 9-fluorenylmethyl carbonate (Fmoc), alkyl ethyl carbonate, alkyl 2,2,2-trichloroethyl carbonate (Troc), 2-(trimethylsilyl)ethyl carbonate (TMSEC), 2-(phenylsulfonyl)ethyl carbonate (Psec), 2-(triphenylphosphonio) ethyl carbonate (Peoc), alkyl isobutyl carbonate, alkyl vinyl carbonate alkyl allyl carbonate, alkyl p-nitrophenyl carbonate, alkyl benzyl carbonate, alkyl p-methoxybenzyl carbonate, alkyl 3,4-dimethoxybenzyl carbonate, alkyl o-nitrobenzyl carbonate, alkyl p-nitrobenzyl carbonate, alkyl S-benzyl thiocarbonate, 4-ethoxy-1-napththyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxycarbonyl)benzoate, α-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts). For protecting 1,2- or 1,3-diols, the protecting groups include methylene acetal, ethylidene acetal, 1-t-butylethylidene ketal, 1-phenylethylidene ketal, (4-methoxyphenyl)ethylidene acetal, 2,2,2-trichloroethylidene acetal, acetonide, cyclopentylidene ketal, cyclohexylidene ketal, cycloheptylidene ketal, benzylidene acetal, p-methoxybenzylidene acetal, 2,4-dimethoxybenzylidene ketal, 3,4-dimethoxybenzylidene acetal, 2-nitrobenzylidene acetal, methoxymethylene acetal, ethoxymethylene acetal, dimethoxymethylene ortho ester, 1-methoxyethylidene ortho ester, 1-ethoxyethylidine ortho ester, 1,2-dimethoxyethylidene ortho ester, α-methoxybenzylidene ortho ester, 1-(N,N-dimethylamino)ethylidene derivative, α-(N,N'-dimethylamino)benzylidene derivative, 2-oxacyclopentylidene ortho ester, di-t-butylsilylene group (DTBS), 1,3-(1,1,3,3-tetraisopropyldisiloxanylidene) derivative (TIPDS), tetra-t-butoxydisiloxane-1,3-diylidene derivative (TBDS), cyclic carbonates, cyclic boronates, ethyl boronate, and phenyl boronate.

The term "thio," or "thiol," as used herein, refers to a group of the formula (—SH). An "optionally substituted thiol" refers to a group of the formula (—SR$^r$), wherein R$^r$ can be hydrogen, or any substitutent. Substituents include, but are not limited to, any of the substituents described herein, that result in the formation of a stable moiety (for example, a thio group substituted with one or more aliphatic, alkyl, alkenyl, alkynyl, heteroaliphatic, heterocyclic, aryl, heteroaryl, acyl, sulfinyl, and/or sulfonyl).

A "suitable thiol protecting group," as used herein, are well known in the art and include those described in detail in *Protecting Groups in Organic Synthesis*, T. W. Greene and P. G. M. Wuts, 3$^{rd}$ edition, John Wiley & Sons, 1999, the entirety of which is incorporated herein by reference. Examples of suitably protected thiol groups further include, but are not limited to, thioesters, carbonates, sulfonates allyl thioethers, thioethers, silyl thioethers, alkyl thioethers, arylalkyl thioethers, and alkoxyalkyl thioethers. Examples of suitable ester groups include formates, acetates, proprionates, pentanoates, crotonates, and benzoates. Specific examples of suitable ester groups include formate, benzoyl formate, chloroacetate, trifluoroacetate, methoxyacetate, triphenylmethoxyacetate, p-chlorophenoxyacetate, 3-phenylpropionate, 4-oxopentanoate, 4,4-(ethylenedithio)pentanoate, pivaloate (trimethylacetate), crotonate, 4-methoxy-crotonate, benzoate, p-benzylbenzoate, 2,4,6-trimethylbenzoate. Examples of suitable carbonates include 9-fluorenylmethyl, ethyl, 2,2,2-trichloroethyl, 2-(trimethylsilyl)ethyl, 2-(phenylsulfonyl)ethyl, vinyl, allyl, and p-nitrobenzyl carbonate. Examples of suitable silyl groups include trimethylsilyl, triethylsilyl, t-butyldimethylsilyl, t-butyldiphenylsilyl, triisopropylsilyl ether, and other trialkylsilyl ethers. Examples of suitable alkyl groups include methyl, benzyl, p-methoxybenzyl, 3,4-dimethoxybenzyl, trityl, t-butyl, and allyl ether, or derivatives thereof. Examples of suitable arylalkyl groups include benzyl, p-methoxybenzyl (MPM), 3,4-dimethoxybenzyl, O-nitrobenzyl, p-nitrobenzyl, p-halobenzyl, 2,6-dichlorobenzyl, p-cyanobenzyl, 2- and 4-picolyl ethers.

The terms "halo" and "halogen" as used herein refer to an atom selected from fluorine (fluoro, —F), chlorine (chloro, —Cl), bromine (bromo, —Br), and iodine (iodo, —I).

The term "cyano," as used herein, refers to a group of the formula (—CN).

The term "isocyano," as used herein, refers to a group of the formula (—NC).

The term "azido," as used herein, refers to a group of the formula (—N$_3$). An "optionally substituted azido" refers to a group of the formula (—N$_3$R$^i$), wherein R$^i$ can be any substitutent (other than hydrogen). Substituents include, but are not limited to, any of the substituents described herein, that result in the formation of a stable moiety (for example, an azido group substituted with one or more aliphatic, alkyl, alkenyl, alkynyl, heteroaliphatic, heterocyclic, aryl, heteroaryl, acyl, sulfinyl, and/or sulfonyl groups).

The term "hydrazine" or "hydrazino," as used herein, refers to the group of the formula —N(R$^j$)N(R$^j$)$_2$, wherein R$^j$ can be any substituent. Substituents include, but are not limited to, any of the substituents described herein, that result in the formation of a stable moiety (for example, an hydrazino group substituted with one or more hydrogens, aliphatic, alkyl, alkenyl, alkynyl, heteroaliphatic, heterocyclic, aryl, heteroaryl, acyl, sulfinyl, and/or sulfonyl groups).

The term "nitro," as used herein, refers to a group of the formula (—NO$_2$).

The term "oxo," as used herein, refers to a group of the formula (=O).

The term "thiooxo," as used herein, refers to a group of the formula (=S).

The term "imino," as used herein, refers to a group of the formula (=NR$^r$), wherein R$^r$ corresponds to hydrogen or any substituent as described herein, that results in the formation of a stable moiety (for example, a suitable amino protecting group; substituted or unsubstituted amino; acyl; cyclic or acyclic, branched or unbranched, substituted or unsubstituted alkyl; cyclic or acyclic, branched or unbranched, substituted or unsubstituted alkenyl; cyclic or acyclic, branched or unbranched, substituted or unsubstituted alkynyl; cyclic or acyclic, branched or unbranched, substituted or unsubstituted heteroalkyl; cyclic or acyclic, branched or unbranched, substituted or unsubstituted heteroalkenyl; cyclic or acylic, branched or unbranched, substituted or unsubstituted heteroalkynyl; substituted or unsubstituted aryl; or substituted or unsubstituted heteroaryl).

The following definitions are more general terms used throughout the present application:

The term "subject," as used herein, refers to any animal. In certain embodiments, the subject is a mammal. In certain embodiments, the term "subject", as used herein, refers to a human (e.g., a man, a woman, or a child).

The terms "administer," "administering," or "administration," as used herein refers to implanting, absorbing, ingesting, injecting, or inhaling, the inventive polymer or compound.

The terms "treat" or "treating," as used herein, refers to partially or completely alleviating, inhibiting, ameliorating, and/or relieving the disease or condition from which the subject is suffering.

The terms "effective amount" and "therapeutically effective amount," as used herein, refer to the amount or concentration of a biologically active agent conjugated to an inventive polymer of the presently claimed invention, or amount or concentration of an inventive polymer, that, when administered to a subject, is effective to at least partially treat a condition from which the subject is suffering.

As used herein, when two entities are "conjugated" to one another they are linked by a direct or indirect covalent or non-covalent interaction. In certain embodiments, the association is covalent. In other embodiments, the association is non-covalent. Non-covalent interactions include hydrogen bonding, van der Waals interactions, hydrophobic interactions, magnetic interactions, electrostatic interactions, etc. An indirect covalent interaction is when two entities are covalently connected through a linker group.

"Biocompatible": The term "biocompatible", as used herein is intended to describe inventive polymers that do not elicit a substantial detrimental response in vivo. In certain embodiments, the inventive polymers are "biocompatible" if they are not toxic to cells. In certain embodiments, the inventive polymers are "biocompatible" if their addition to cells in vitro results in less than or equal to 20% cell death, and/or their administration in vivo does not induce inflammation or other such adverse effects. In certain embodiments, biocompatible polymers are also biodegradable.

"Biodegradable": As used herein, "biodegradable" inventive polymers are those that, when introduced into cells, are broken down by the cellular machinery (e.g., enzymatic degradation) or by hydrolysis into components that the cells can either reuse or dispose of without significant toxic effects on the cells. In certain embodiments, the components do not induce inflammation and/or other adverse effects in vivo. In certain embodiments, the chemical reactions relied upon to break down the biodegradable inventive polymers are enzymatically broken down. For example, the inventive polymers may be broken down in part by the hydrolysis of ester bonds. In certain embodiments, biodegradable polymers are polymers that fully degrade down to their monomeric components under physiological conditions. In certain embodiments, biodegradable polymers are also biocompatible.

The term "pharmaceutically acceptable salt" includes acid addition salts, that is salts derived from treating a compound of the presently claimed invention with an organic or inorganic acid such as, for example, acetic, lactic, citric, cinnamic, tartaric, succinic, fumaric, maleic, malonic, mandelic, malic, oxalic, propionic, hydrochloric, hydrobromic, phosphoric, nitric, sulfuric, glycolic, pyruvic, methanesulfonic, ethanesulfonic, toluenesulfonic, salicylic, benzoic, or similarly known acceptable acids. Where a compound the presently claimed invention contains a substituent with acidic properties, for instance, a carboxylic acid, the term also includes salts derived from bases, for example, sodium, potassium, calcium, magnesium, lithium, and barium salts.

The term "hydrogel," as used herein, is a polymer which absorbs at least 10 wt % of water (in the presence of an abundance of water). When the content of water exceeds 95% of the total weight (i.e., 95 wt %), the hydrogel is a superabsorbent hydrogel.

The term "elastomer," as used herein, is a polymer that can return rapidly to the approximate shape from which it has been substantially distorted by a weak stress. In certain embodiments, the elastomer can be stretched repeatedly to at least twice its original length and which, upon release of the stress, will immediately return to approximately its original length. In certain embodiments, the elastomer polymer does not sustain permanent structural deformation upon stretching the elastomer polymer between about 1% to 300% its original length.

As used herein, the term "substantially clear," or "clear," "optically clear," or "transparent," refers to a sample specimen with a light transmission percentage of at least 85%, at least 90%, at least 95%, or at least 99%. It is possible to measure the degree of light transmission using ASTM D-1003 (Standard Test Method for Haze and Luminous Transmittance of Transparent Plastics), and this test method is used to evaluate light transmission and scattering of transparent plastics for a defined specimen thickness. The term "substantially clear," or "clear," "optically clear," or "transparent," may also refer to a sample specimen which has a constant refractive index through the sample in the viewing direction. The perceived transparency or optical clarity is dependent on the thickness of the sample used for assessment, and the optical clarity will decrease with increasing thickness. Any areas of opaque material (such as colorants) or areas of different refractive index, will result in a loss of optical clarity due to refraction and scattering. Optical clarity is also dependent on surface reflections from the sample.

PLGA. Images are 10× and bars represent 200 µm. P=polymer, C=fibrous capsule, S=skin, and M=muscle.

Figure 10:
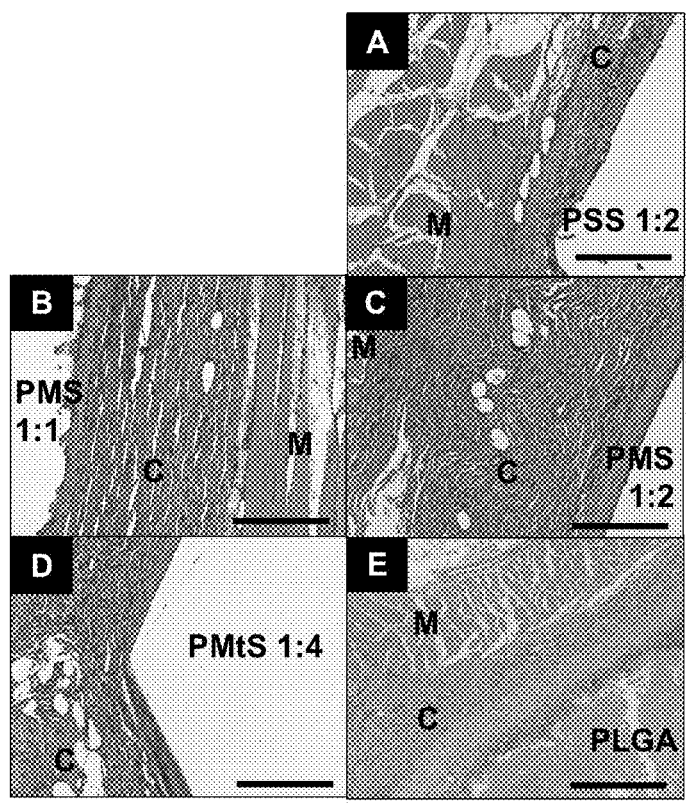

FIG. 10. Representative images of H&E stained sections demonstrating the chronic inflammatory response to subcutaneous implanted PPS polymers, 12 weeks after implantation. The PSS 1:1 elastomer had completely degraded at this time. (A) PSS 1:2, (B) PMS 1:1, (C) PMS 1:2, (D) PMtS 1:4 and (E) PLGA. Images A-D are 20×, and bars represent 100 jam. Image E is 10×, and bar represents 200 µm. P=polymer, C=fibrous capsule, S=skin, and M=muscle.

Figure 11:
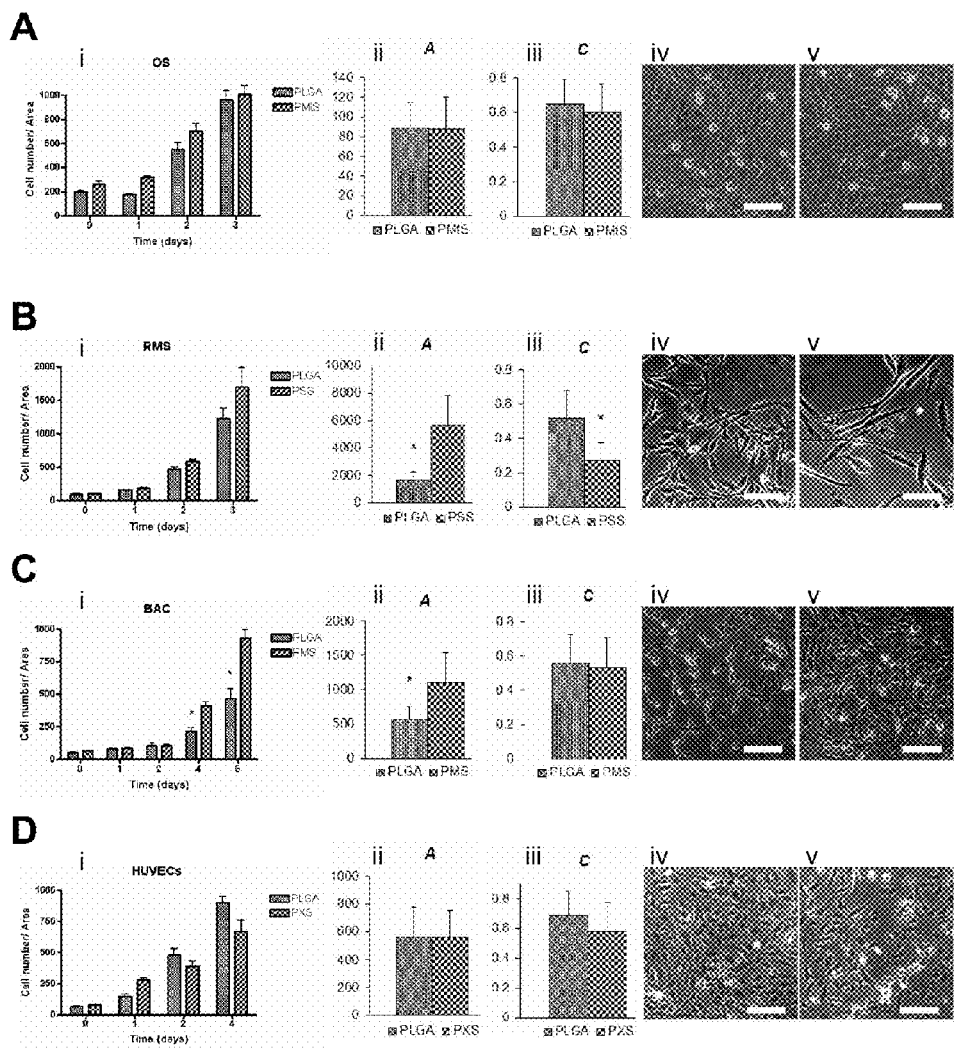

FIG. 11. Initial in vitro analysis of PPS polymers for musculoskeletal tissues. (A) Attachment and subsequent proliferation of an OS cell-line derived from human bone on PMtS 1:4 films, compared to PLGA (i). OS cell morphology was quantified by cell area (A) (ii) and circularity (C) (iii), also demonstrated by representative phase-contrast images of OS cells (iv) and (v) (10×, bars represent 100 µm). (B) Attachment and proliferation of RMS cells derived from human muscle on PSS 1:2 and compared to PLGA films (i), as well as cell morphology: (ii) for A and (iii) for C (* indicate p<0.05). Representative images (iv) (v) demonstrated the difference (10×, bars represent 100 µm). (C) Seeding of primary BACs on PMS 1:2 and PLGA: attachment and subsequent cell numbers (i) (* indicate p<0.05), as well as A (ii) (p<0.05) and C (iv) (p>0.05). Representative images are shown: (iv) and (v). (D) HUVECs attached and proliferated on PXS 1:1 elastomers similar to PLGA (i), and revealed similar cell shape (ii) and (iii), also demonstrated by phase contrast images (iv) and (v) (20×, bars represent 50 µm).

Figure 12:
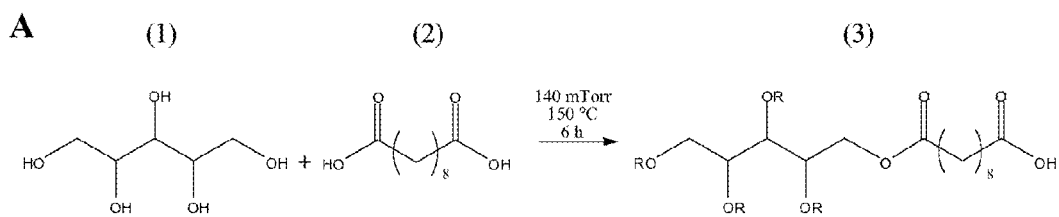
Figure 12:
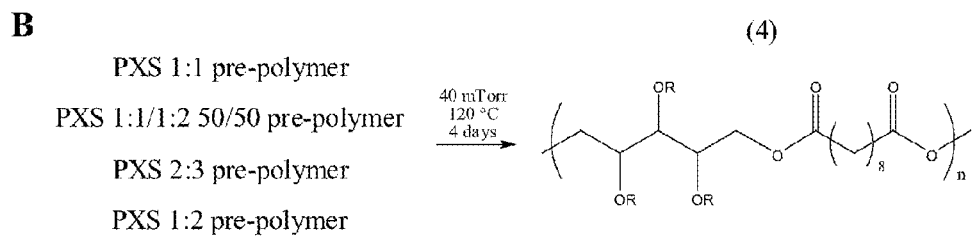

FIG. 12. General synthetic scheme of PXS elastomers. Xylitol was polymerized with sebacic acid in different stoichiometries. A simplified representation of the pre-polymers is shown. R can be a hydrogen, or a xylitol or sebacic acid molecule.

Figure 13:
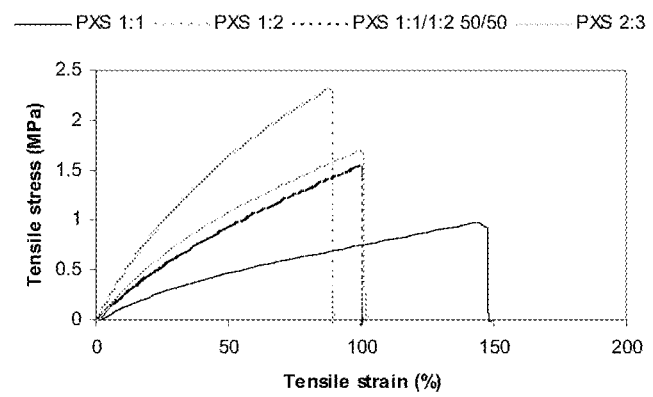

FIG. 13. Representative tensile stress versus strain plots of PXS elastomers studied here.

Figure 14:
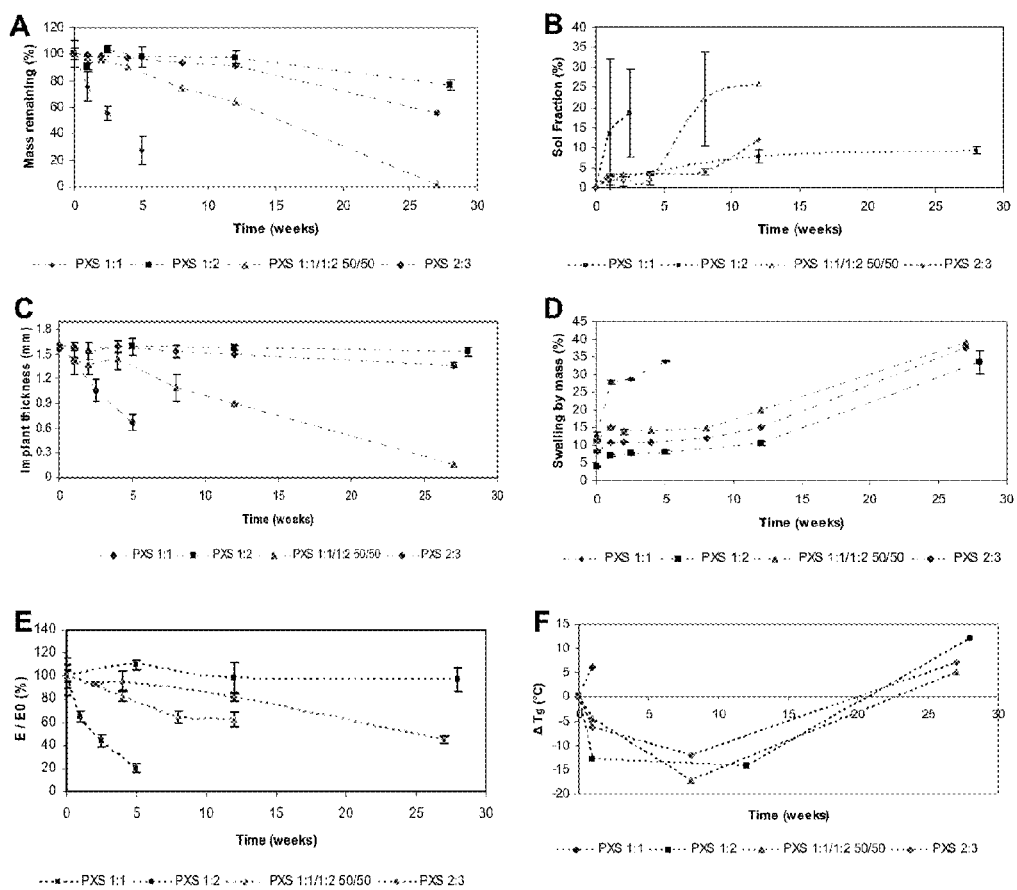

FIG. 14. In vivo behavior of PXS elastomers over time: mass loss (A), sol fraction (B), implant thickness (C), hydration by mass (D), mechanical properties (E) and ΔTg (F).

Figure 15:
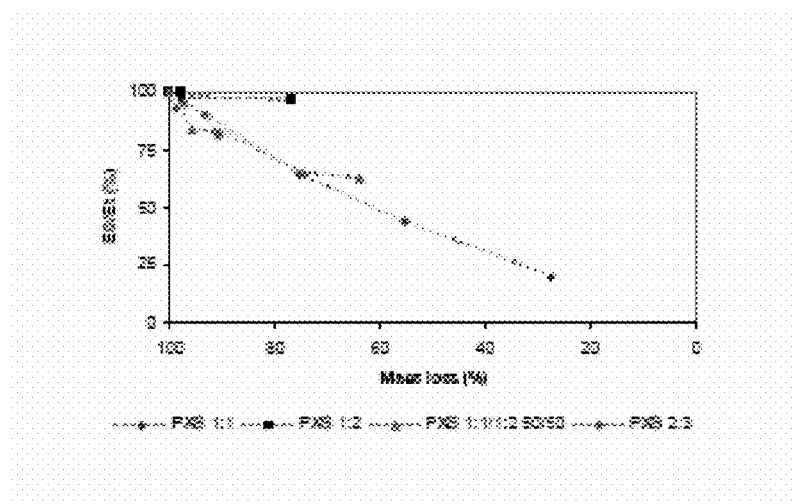

FIG. 15. Loss of mechanical properties (E0/Et×100%) versus mass loss (%) for PXS elastomers.

Figure 16:
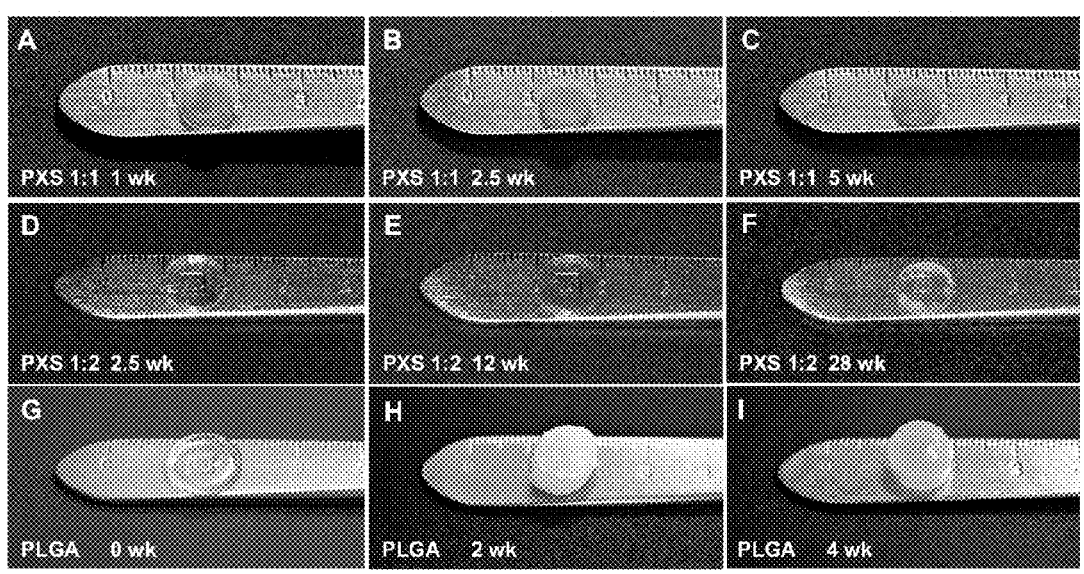

FIG. 16. Gross morphology of ex vivo implants: PXS 1:1 implants became opaque after 1 week (A) but did not swell during degradation, at 2.5 (B), and 5 (C) weeks. PXS 1:2 implants remained optically transparent after 2.5 (D) and 12 (E) weeks, and became slightly opaque after 28 (F) weeks of implantation. PLGA implants (G) became swollen and opaque at 2 (H) and 4 (I) weeks.

Figure 17:
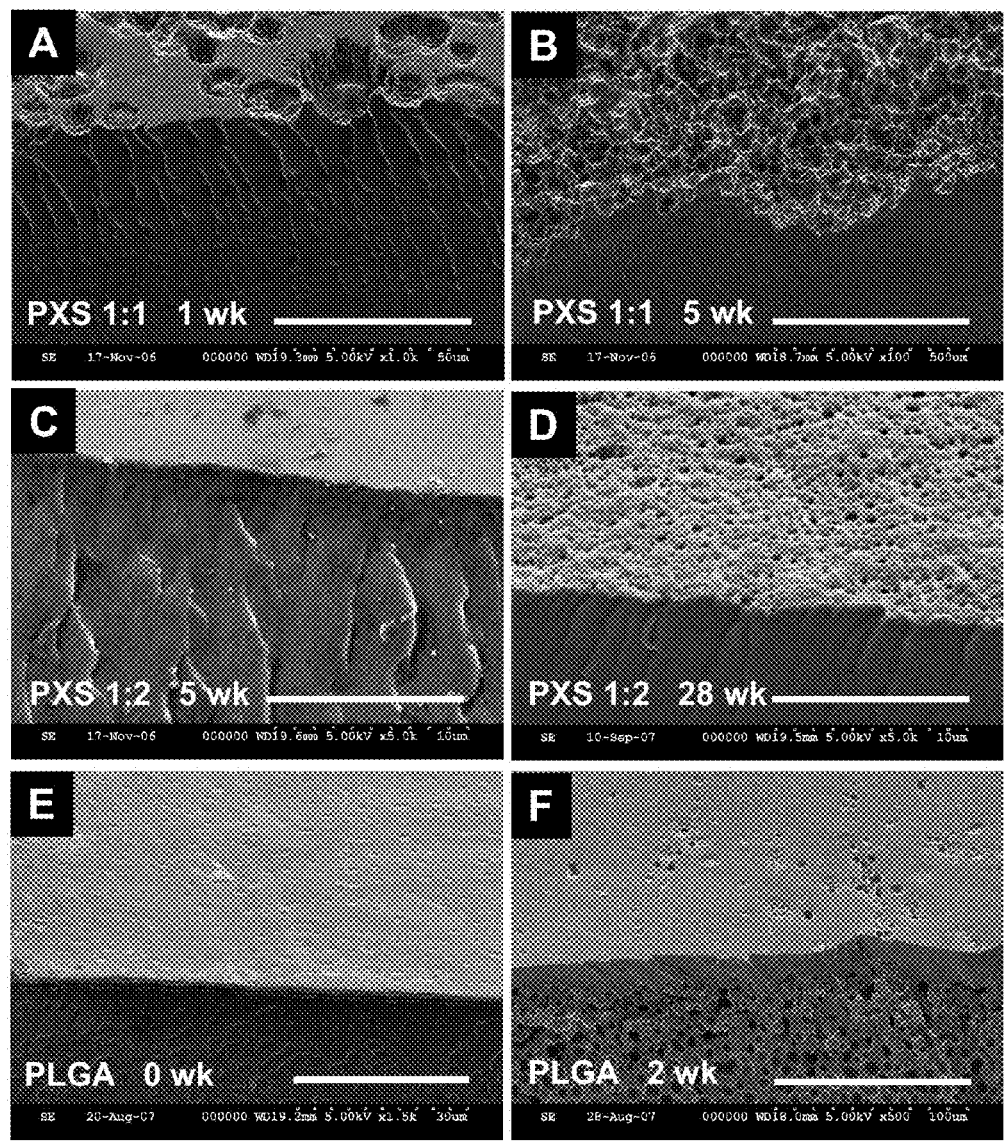

FIG. 17. SEM micrographs of PXS and PLGA implants. Representative images of PXS 1:1 at 1 week (A) (bar represents 50 µm) and at 5 weeks in vivo (B) (bar represents 500 µm), PXS 1:2 at 5 weeks (C) (bar represents 10 µm) and at 28 weeks in vivo (D) (bar represents 10 µm), and PLGA at 0 weeks (E) (bar represents 30 µm) and at 2 weeks in vivo (F) (bar represents 100 µm) are shown.

Figure 18:
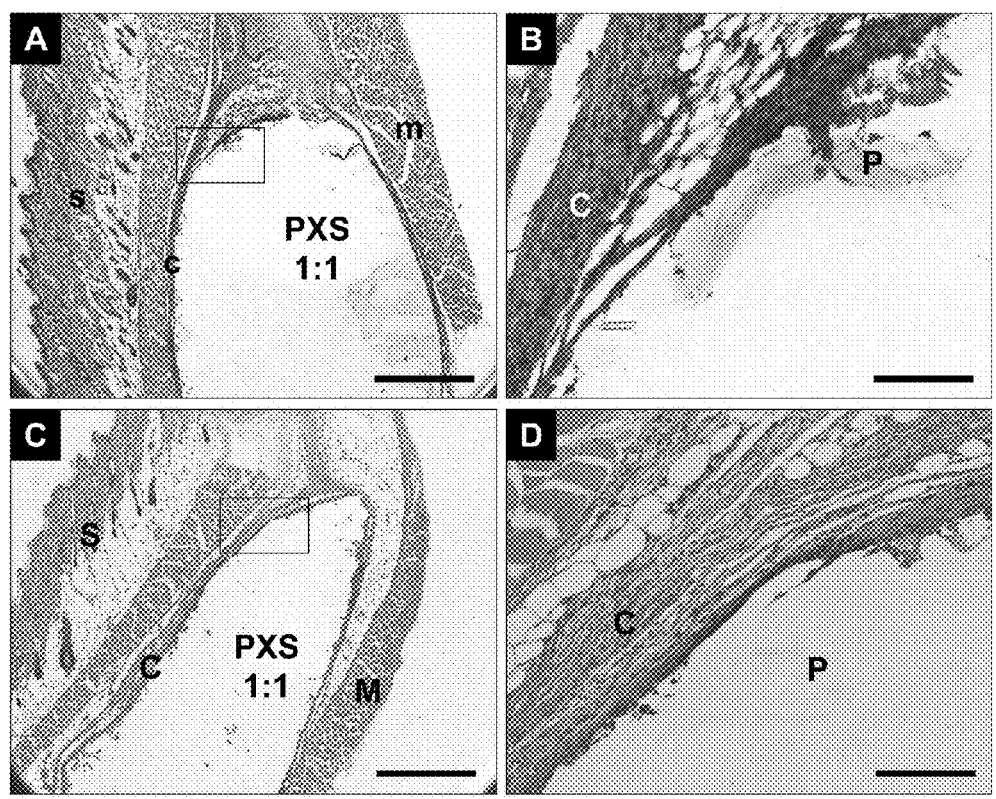

FIG. 18. Representative images of H&E stained sections of subcutaneous implantation sites of PXS 1:1 elastomers. An overview of the acute inflammatory response surrounding PXS 1:1 implants at week 1 is shown at 2.5× (A) (bar represents 500 µm), and in more detail at 20× (B) (bar represents 75 µm). An overview of the chronic foreign body response surrounding degrading PXS 1:1 implants is shown at 2.5× (C) (bar represents 500 µm), and in more detail at 20× (D) (bar represents 75 µm). The areas of the detailed images are represented in A and C by the black rectangular. P=polymer, C=fibrous capsule, S=skin and M=muscle.

Figure 19:
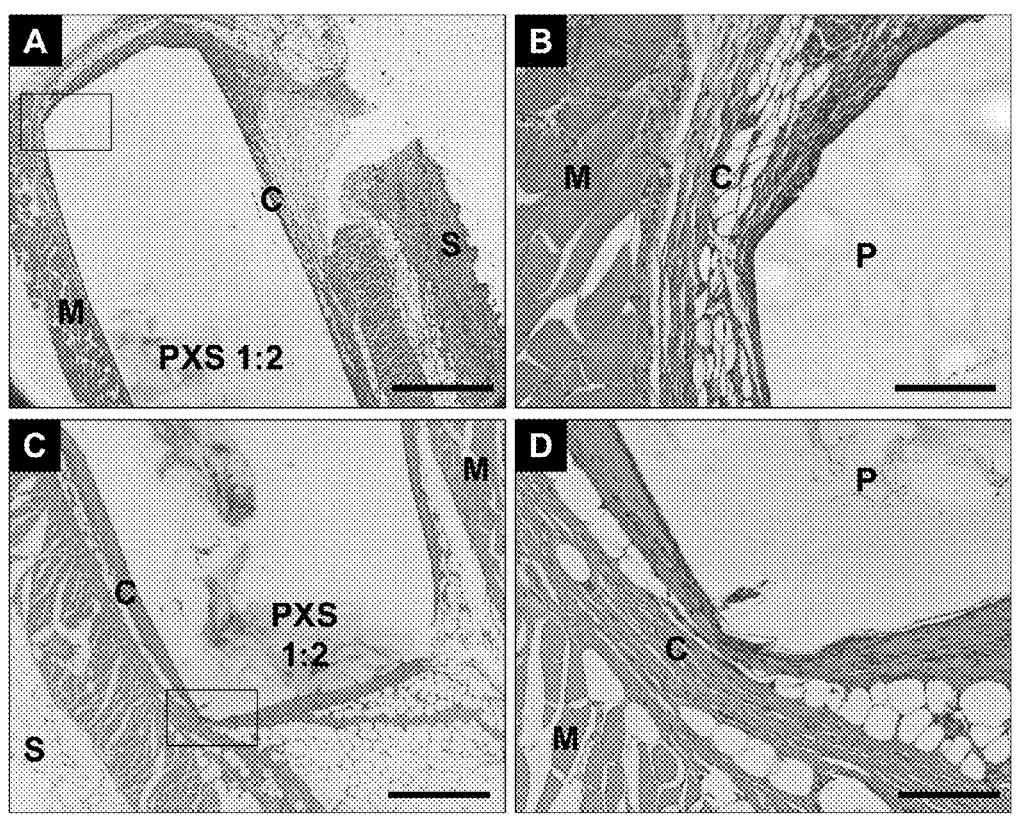

FIG. 19. Representative images of H&E stained sections of subcutaneous implantation sites of PXS 1:2 elastomers. An overview of the acute inflammatory response surrounding PXS 1:2 implants at week 1 is shown at 2.5× (A) (bar represents 500 µm), and in more detail at 10× (B) (bar represents 150 µm). An overview of the chronic foreign body response surrounding degrading PXS 1:2 implants at 28 weeks is shown at 5× (C) (bar represents 250 µm), and in more detail at 20× (D) (bar represents 75 µm). The areas of the detailed images are represented in A and C by the black rectangular. P=polymer, C=fibrous capsule, S=skin and M=muscle.

Figure 20:
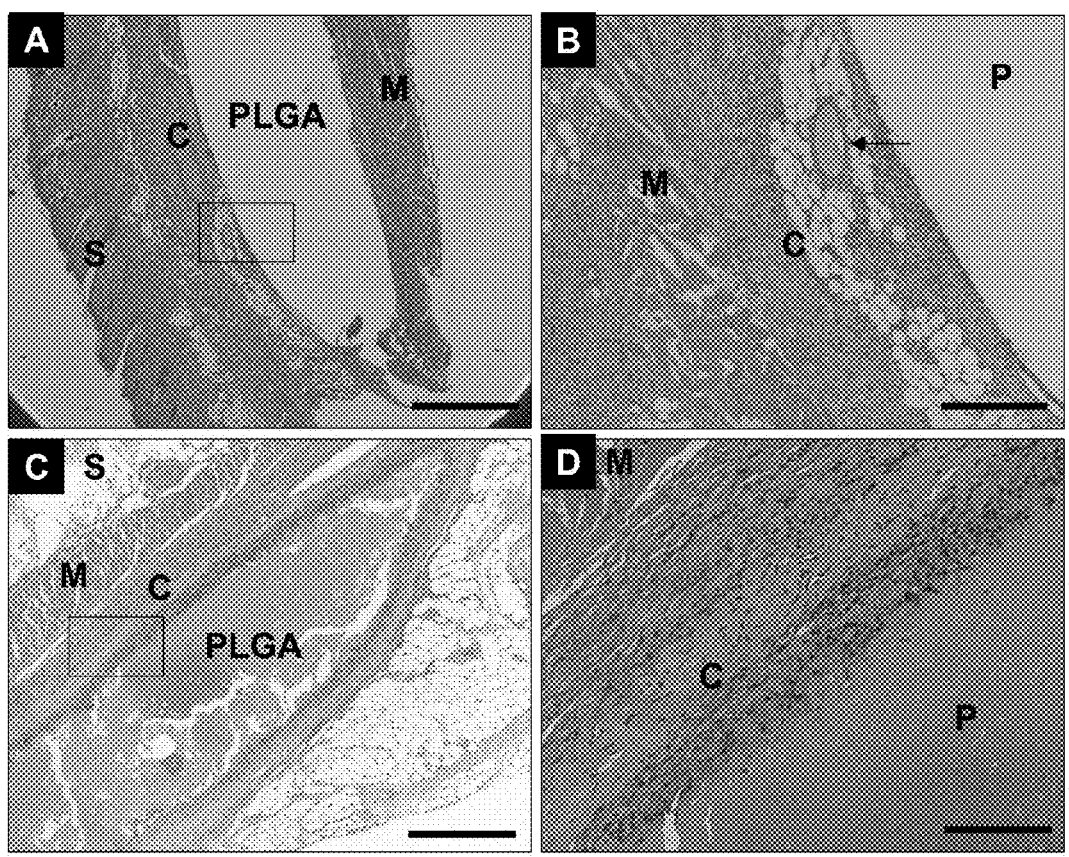

FIG. 20. Representative images of H&E stained sections of subcutaneous implantation sites of PLGA implants. An overview of the acute inflammatory response surrounding PLGA implants at week 1 is shown at 2.5× (A) (bar represents 500 µm), and in more detail at 10× (B) (bar represents 150 µm). An overview of the chronic foreign body response surrounding degrading PLGA implants at 12 weeks is shown at 5× (C) (bar represents 250 µm), and in more detail at 20× (D) (bar represents 75 µm). The areas of the detailed images are represented in A and C by the black rectangular. P=polymer, C=fibrous capsule, S=skin and M=muscle. The arrow points to a large vessel of the fibrous capsule surrounding the PLGA implant.

Figure 21:
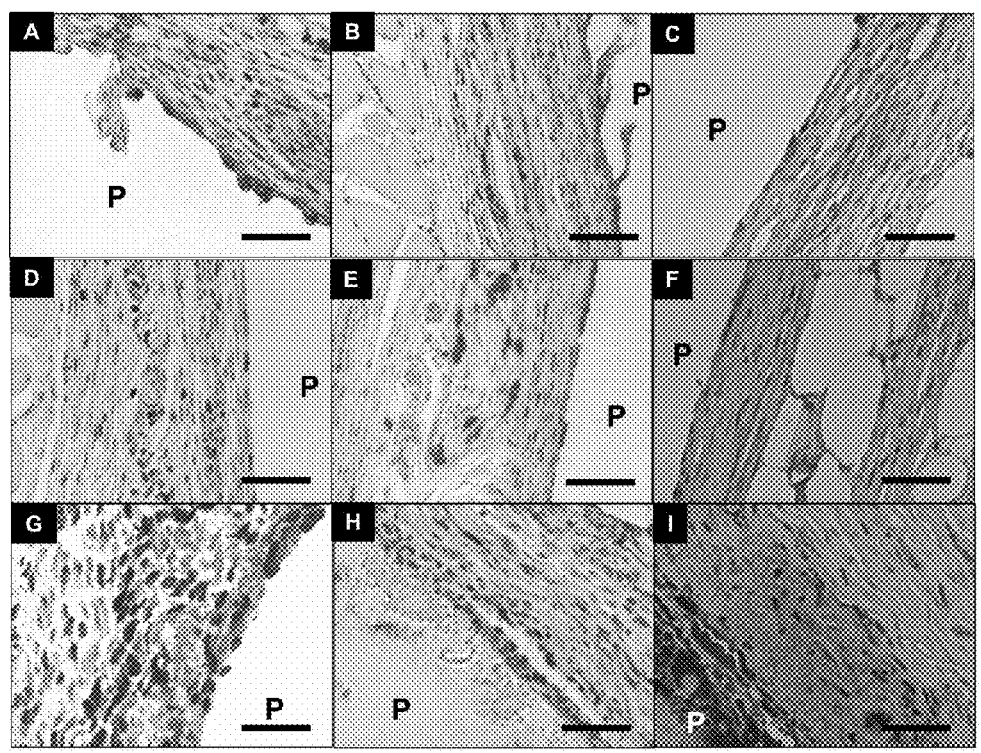

FIG. 21. Representative images of CD68 stained sections of subcutaneous implantation sites of PXS and PLGA implants. Recruited and activated macrophages are CD68+ (Greaves et al., $Int. J. Hemtol.$ 76(1):6-15, 2002). All images are magnified at 20× (bars represent 25 λm). Fibrous capsules surrounding PXS 1:1 at 1 week (A), 2 weeks (B), and 5 weeks (C) showed CD68+ cells, similar to the PXS 1:2 at 1 week (D), 2 weeks (E) and 12 weeks (F). Fibrous capsules surrounding the PLGA implants seemed to have more CD68+ cells at 1 week (G), 2 weeks (H), and 12 weeks (I).

Figure 22:
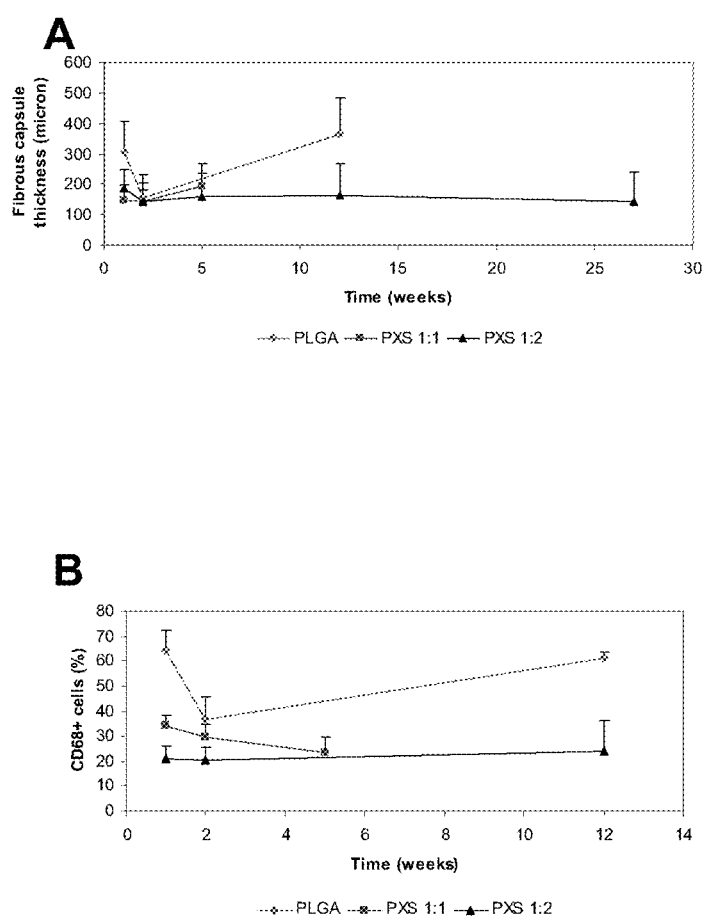

FIG. 22. Quantitative analysis of in vivo biocompatibility. Fibrous capsule thicknesses were measured and compared for PXS 1:1, 1:2, and PLGA implants (A) as well as numbers of activated macrophages (CD68+) within the fibrous capsules (B).

Figure 23:
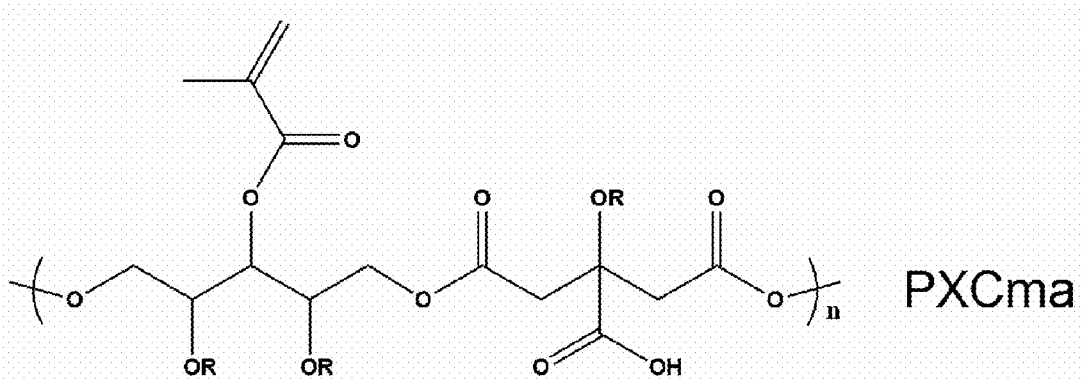
Figure 23:
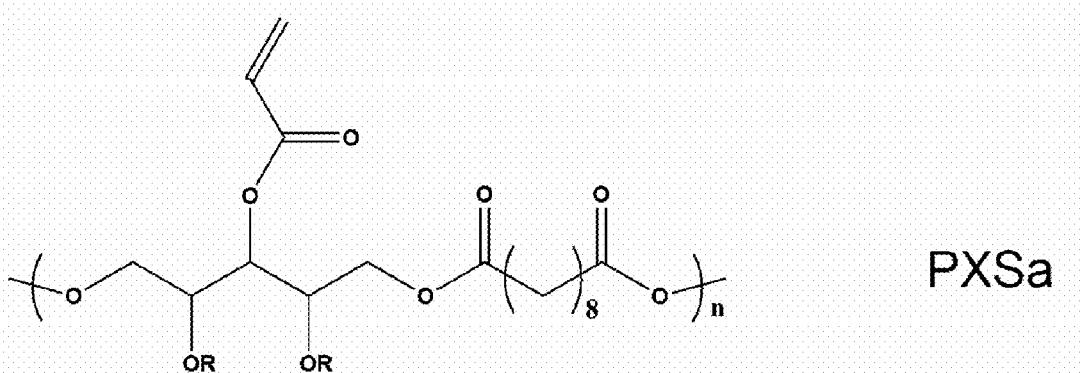

FIG. 23. Exemplary acrylated polymers, PXCma and PXSa. The R groups may be, independently, hydrogen, a suitable hydroxyl protecting group, an acrylate moiety, or other any other group as described herein.

Figure 24:
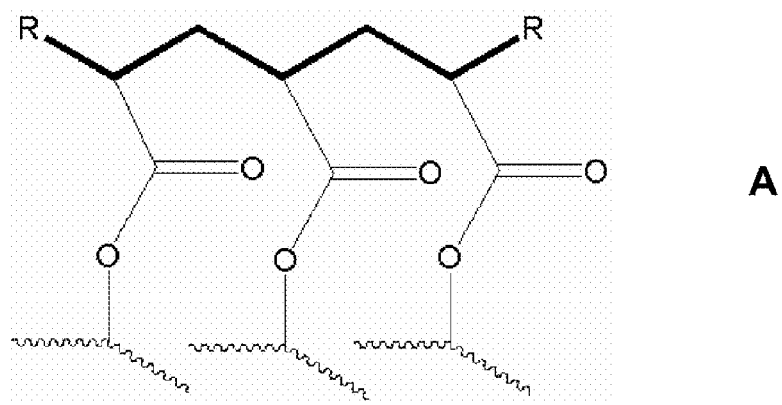
Figure 24:
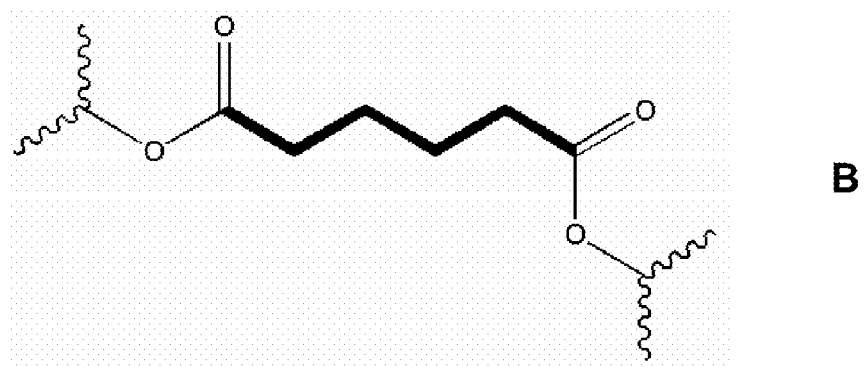

FIG. 24. Exemplary linkage groups formed via polymerization of acrylate groups present on an inventive polymer.

Figure 25:
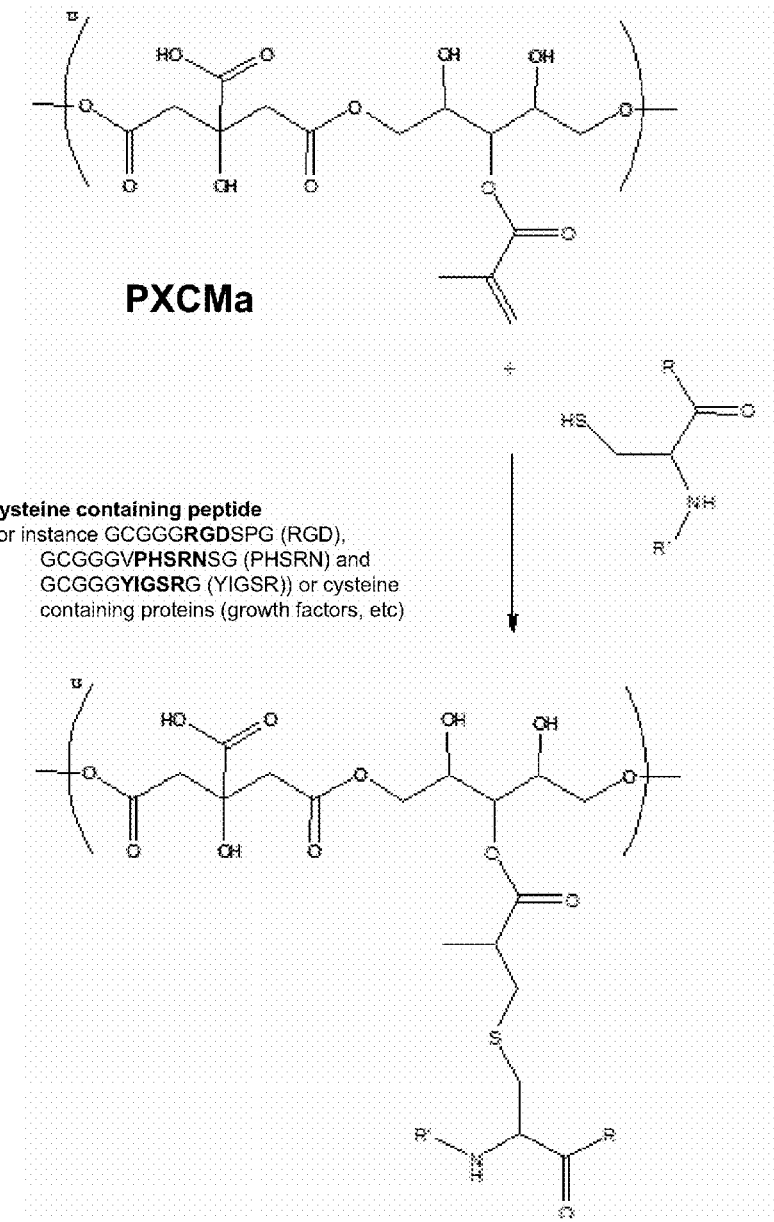

FIG. 25. Reaction of acrylate moieties present on an inventive polymer can also be used to covalently bind biological active structures.

Figure 26A:
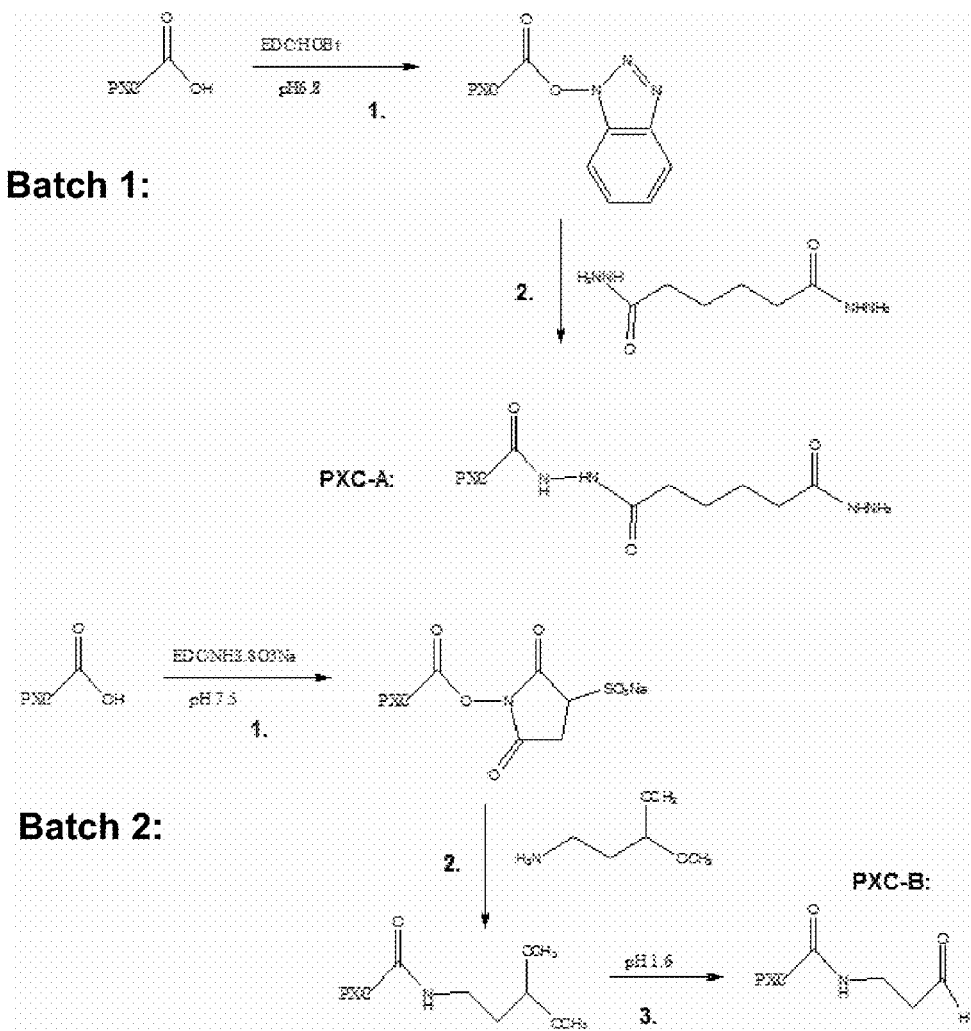
Figure 26B:
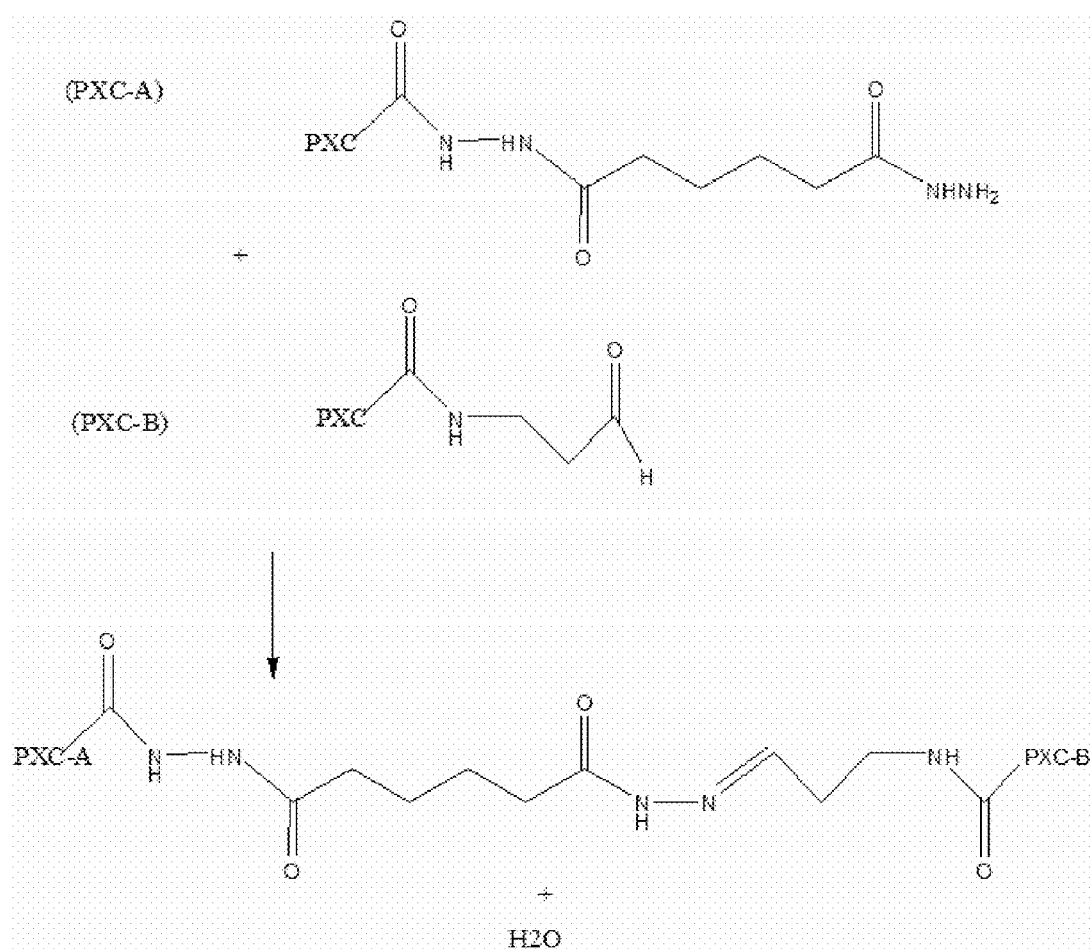

FIGS. 26A-26B. PXC-Aldehyde (PXC-ALD) and PXC-Adipic Dihydrazide (PXC-ADH) In situ Crosslinking. FIG. 26A: Batch 1. Coupling of PXC to adipic dihydrazide; Batch 2: Modification of PXC to provide an aldehyde functional group; FIG. 26B: Mixing the two batches to provide a crosslinked polymer.

Figure 27:
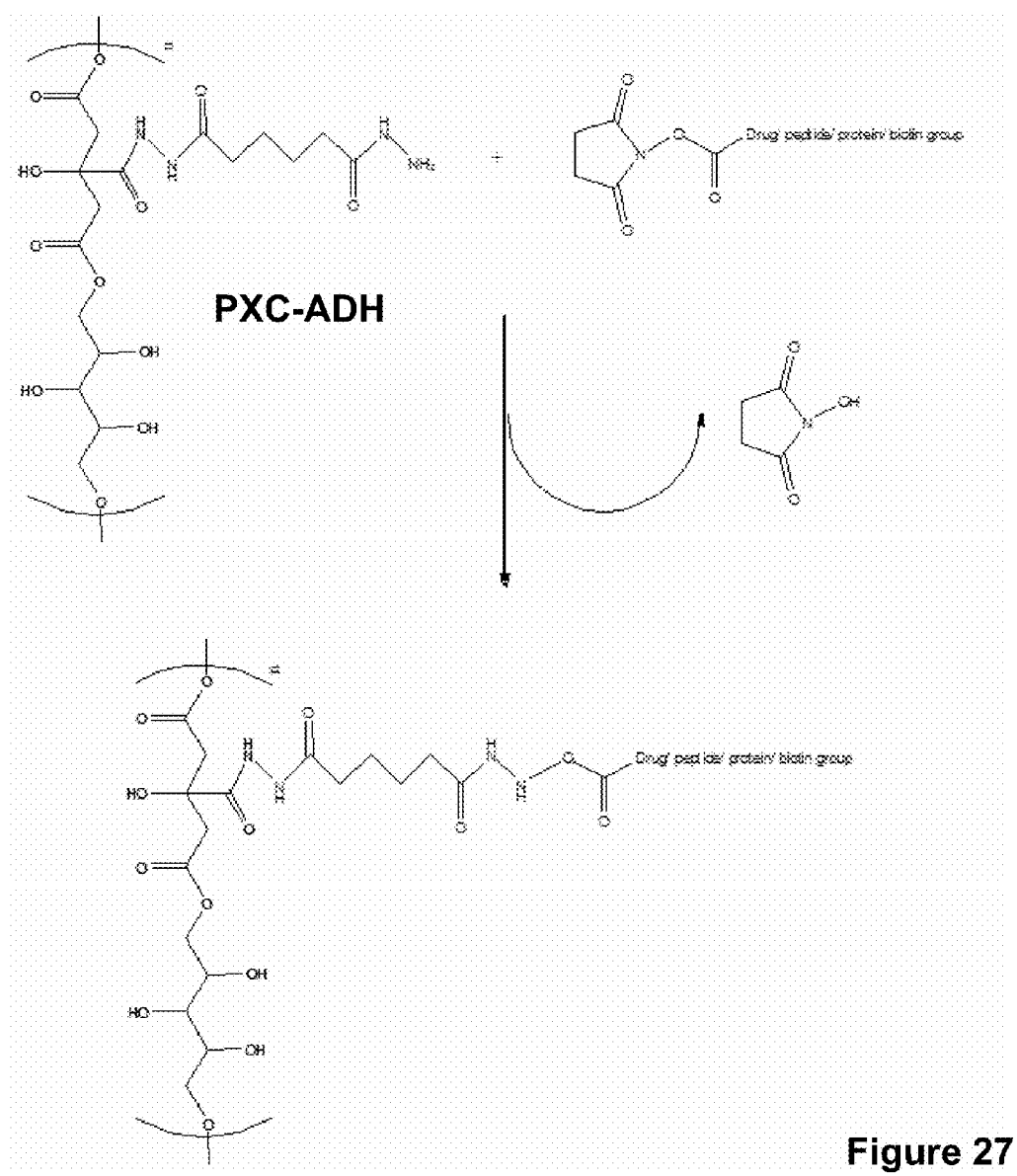

FIG. 27. Exemplary Reaction Between PXC-ADH and an activated carboxylate (e.g., a modified N-hydroxysuccinimide (NHS)-ester).

Figure 28:
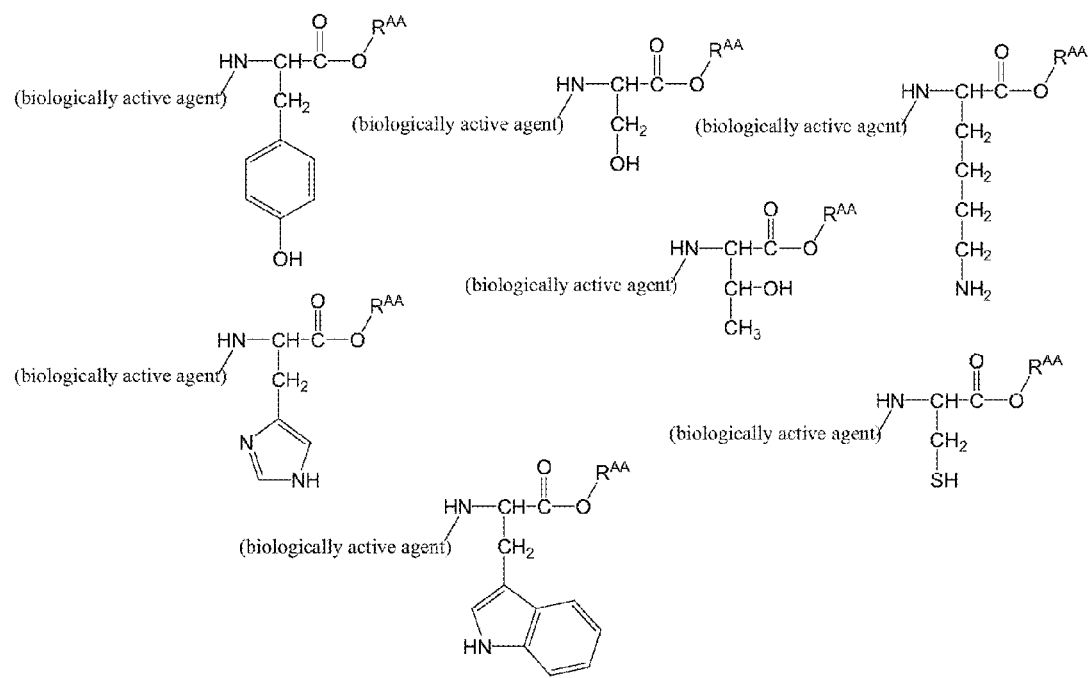

FIG. 28. Biologically active agents tethered to amino acids which contain nucleophilic oxygen, sulfur, or nitrogen groups.

DETAILED DESCRIPTION OF CERTAIN EMBODIMENTS OF THE INVENTION

The present invention provides novel polyol-based polymers; novel polyol-based polymers comprising one or more biologically active agents; pharmaceutical compositions comprising an inventive polyol-based polymer; pharmaceutical compositions comprising an inventive polyol-based polymer and one or more biologically active agents; and methods of making and using an inventive polyol-based polymer or an inventive polyol-based polymer conjugated to one or more biologically active agents.

Inventive Polymers

In certain aspects of the present invention, a polymer of the present invention has the following formula:

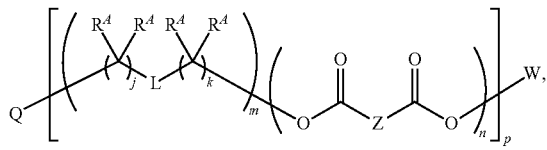

wherein:

each instance of Z and L, are, independently, cyclic or acyclic, branched or unbranched, substituted or unsubstituted alkylene; cyclic or acyclic, branched or unbranched, substituted or unsubstituted alkenylene; cyclic or acyclic, branched or unbranched, substituted or unsubstituted alkynylene; cyclic or acyclic, branched or unbranched, substituted or unsubstituted heteroalkylene; cyclic or acyclic, branched or unbranched, substituted or unsubstituted heteroalkenylene; cyclic or acyclic, branched or unbranched, substituted or unsubstituted heteroalkynylene; substituted or unsubstituted arylene; substituted or unsubstituted heteroarylene; or substituted or unsubstituted acylene;

each instance of $R^A$ is, independently, hydrogen; Q; $-OR^C$; acyl; cyclic or acyclic, branched or unbranched, substituted or unsubstituted alkyl; cyclic or acyclic, branched or unbranched, substituted or unsubstituted alkenyl; cyclic or acyclic, branched or unbranched, substituted or unsubstituted alkynyl; cyclic or acyclic, branched or unbranched, substituted or unsubstituted heteroalkyl; cyclic or acyclic, branched or unbranched, substituted or unsubstituted heteroalkenyl; cyclic or acyclic, branched or unbranched, substituted or unsubstituted heteroalkynyl; substituted or unsubstituted aryl; or substituted or unsubstituted heteroaryl; or two $R^A$ groups are joined to form (=O), (=S), or (=$NR^B$), wherein $R^B$ is hydrogen; a suitable amino protecting group; substituted or unsubstituted amino; acyl; cyclic or acyclic, branched or unbranched, substituted or unsubstituted alkyl; cyclic or acyclic, branched or unbranched, substituted or unsubstituted alkenyl; cyclic or acyclic, branched or unbranched, substituted or unsubstituted alkynyl; cyclic or acyclic, branched or unbranched, substituted or unsubstituted heteroalkyl; cyclic or acyclic, branched or unbranched, substituted or unsubstituted heteroalkenyl; cyclic or acyclic, branched or unbranched, substituted or unsubstituted heteroalkynyl; substituted or unsubstituted aryl; or substituted or unsubstituted heteroaryl;

W is hydrogen, or a suitable carboxylic acid protecting group;

Q is $-OR^C$, wherein $R^C$ is hydrogen; a suitable hydroxyl protecting group; acyl; cyclic or acyclic, branched or unbranched, substituted or unsubstituted alkyl; cyclic or acyclic, branched or unbranched, substituted or unsubstituted alkenyl; cyclic or acyclic, branched or unbranched, substituted or unsubstituted alkynyl; cyclic or acyclic, branched or unbranched, substituted or unsubstituted heteroalkyl; cyclic or acyclic, branched or unbranched, substituted or unsubstituted heteroalkenyl; cyclic or acyclic, branched or unbranched, substituted or unsubstituted heteroalkynyl; substituted or unsubstituted aryl; or substituted or unsubstituted heteroaryl; or Q corresponds to the formula:

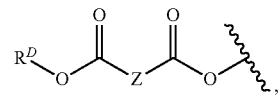

wherein:

$R^D$ is hydrogen, or a suitable carboxylic acid protecting group;

each instance of j is, independently, 0, 1, or 2;
each instance of k is, independently, 0, 1, or 2;
each instance of m is, independently, 1 to 200;
each instance of n is, independently, 1 to 200; and
each instance of p is, independently, 1 to 1000.

In certain embodiments, $R^A$ is hydrogen.

In certain embodiments, j is 0 or 1. In certain embodiments, k is 0 or 1.

In certain embodiments, m is 1 to 100. In certain embodiments, m is 1 to 50. In certain embodiments, m is 1 to 25. In certain embodiments, m is 1 to 10. In certain embodiments, m is 1 to 5. In certain embodiments, m is 1 to 4. In certain embodiments, m is 1 to 3. In certain embodiments, m is 1 to 2. In certain embodiments, m is 1.

In certain embodiments, n is 1 to 100. In certain embodiments, n is 1 to 50. In certain embodiments, n is 1 to 25. In certain embodiments, n is 1 to 10. In certain embodiments, n is 1 to 5. In certain embodiments, n is 1 to 4. In certain embodiments, n is 1 to 3. In certain embodiments, n is 1 to 2. In certain embodiments, n is 1.

In certain embodiments, p is 1 to 900. In certain embodiments, p is 1 to 800. In certain embodiments, p is 1 to 700. In certain embodiments, p is 1 to 600. In certain embodiments, p is 1 to 500. In certain embodiments, p is 1 to 400. In certain embodiments, p is 1 to 300. In certain embodiments, p is 1 to 200. In certain embodiments, p is 1 to 100. In certain embodiments, p is 1 to 50. In certain embodiments, p is 1 to 25. In certain embodiments, p is 1 to 10. In certain embodiments, p is 1 to 5.

In certain embodiments, the term "substituted" includes substitution with a "biologically-active agent," as defined herein. In certain embodiments, the term "substituted" includes substitution with another inventive polymer, as defined herein.

In certain embodiments, Z is cyclic or acyclic, branched or unbranched, substituted or unsubstituted $C_{1-20}$ alkylene; cyclic or acyclic, branched or unbranched, substituted or unsubstituted $C_{1-20}$ alkenylene; cyclic or acyclic, branched or unbranched, substituted or unsubstituted $C_{1-20}$ alkynylene, cyclic or acyclic, branched or unbranched, substituted or unsubstituted $C_{1-20}$ heteroalkylene; cyclic or acyclic, branched or unbranched, substituted or unsubstituted $C_{1-20}$ heteroalkenylene; cyclic or acyclic, branched or unbranched, substituted or unsubstituted $C_{1-20}$ heteroalkynylene; or substituted or unsubstituted $C_{1-20}$ acylene.

In certain embodiments, Z is cyclic or acyclic, branched or unbranched, substituted or unsubstituted $C_{1-15}$ alkylene; cyclic or acyclic, branched or unbranched, substituted or unsubstituted $C_{1-15}$ alkenylene; cyclic or acyclic, branched or unbranched, substituted or unsubstituted $C_{1-15}$ alkynylene; cyclic or acyclic, branched or unbranched, substituted or unsubstituted $C_{1-15}$ heteroalkylene; cyclic or acyclic, branched or unbranched, substituted or unsubstituted $C_{1-15}$ heteroalkenylene; cyclic or acyclic, branched or unbranched, substituted or unsubstituted $C_{1-15}$ heteroalkynylene; or substituted or unsubstituted $C_{1-15}$ acylene.

In certain embodiments, Z is a cyclic or acylic, branched or unbranched, substituted or unsubstituted $C_{1-10}$ alkylene; cyclic or acylic, branched or unbranched, substituted or unsubstituted $C_{1-10}$ alkenylene; cyclic or acylic, branched or unbranched, substituted or unsubstituted $C_{1-10}$ alkynylene; cyclic or acylic, branched or unbranched, substituted or unsubstituted $C_{1-10}$ heteroalkylene; cyclic or acylic, branched or unbranched, substituted or unsubstituted $C_{1-10}$ heteroalkenylene; cyclic or acylic, branched or unbranched, substituted or unsubstituted $C_{1-10}$ heteroalkynylene; or substituted or unsubstituted $C_{1-10}$ acylene.

In certain embodiments, Z is a cyclic or acylic, branched or unbranched, substituted or unsubstituted $C_{5-10}$ alkylene; cyclic or acylic, branched or unbranched, substituted or unsubstituted $C_{5-10}$ alkenylene; cyclic or acylic, branched or unbranched, substituted or unsubstituted $C_{5-10}$ alkynylene; cyclic or acylic, branched or unbranched, substituted or unsubstituted $C_{5-10}$ heteroalkylene; cyclic or acylic, branched or unbranched, substituted or unsubstituted $C_{5-10}$ heteroalkenylene; cyclic or acylic, branched or unbranched, substituted or unsubstituted $C_{5-10}$ heteroalkynylene; or substituted or unsubstituted $C_{5-10}$ acylene.

In certain embodiments, Z is acyclic.
In certain embodiments, Z is unbranched.
Additionally, in certain embodiments, Z is unsubstituted. For example, in certain embodiments, each instance of $R^Z$ is hydrogen. In certain embodiments, Z corresponds to the formulae:

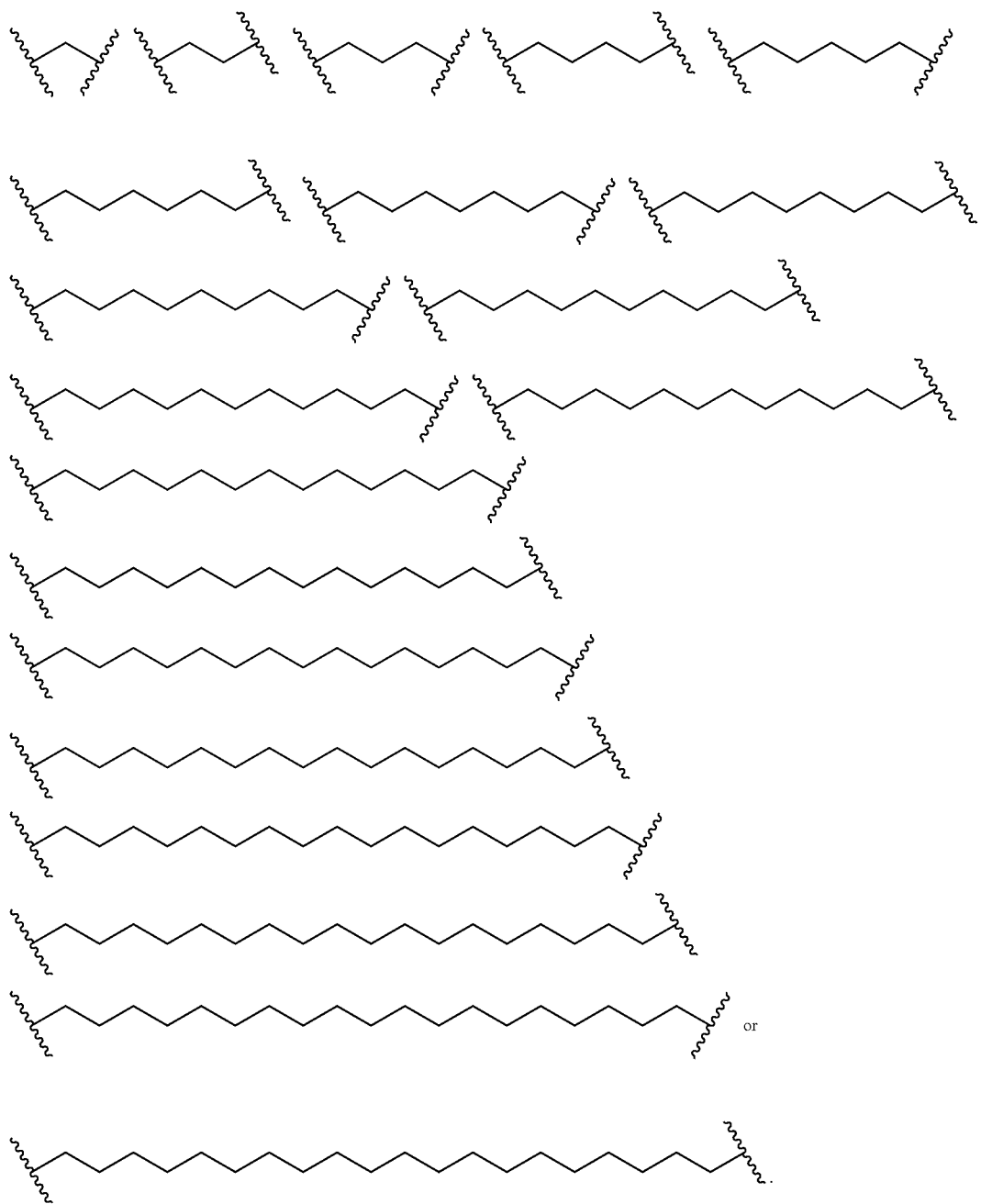

Alternatively, in certain embodiments, Z is substituted.

In certain embodiments, Z is substituted with one or more oxo; thiooxo; imino; substituted or unsubstituted hydroxyl; substituted or unsubstituted amino; substituted or unsubstituted thiol; acyl; cyclic or acylic, branched or unbranched, substituted or unsubstituted alkyl; cyclic or acylic, branched or unbranched, substituted or unsubstituted alkenyl; cyclic or acylic, branched or unbranched, substituted or unsubstituted alkynyl; cyclic or acylic, branched or unbranched, substituted or unsubstituted heteroalkyl; cyclic or acylic, branched or unbranched, substituted or unsubstituted heteroalkenyl; cyclic or acylic, branched or unbranched, substituted or unsubstituted heteroalkynyl; substituted or unsubstituted aryl; or substituted or unsubstituted heteroaryl groups.

In certain embodiments, Z corresponds to the formula:

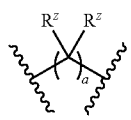

wherein
each instance of $R^Z$ is, independently, hydrogen; acyl; substituted or unsubstituted hydroxyl; substituted or unsubstituted amino; substituted or unsubstituted thiol; cyclic or acylic, branched or unbranched, substituted or unsubstituted alkyl; cyclic or acylic, branched or unbranched, substituted or unsubstituted alkenyl; cyclic or acylic, branched or unbranched, substituted or unsubstituted alkynyl; cyclic or acylic, branched or unbranched, substituted or unsubstituted heteroalkyl; cyclic or acylic, branched or unbranched, substituted or unsubstituted heteroalkenyl; cyclic or acylic, branched or unbranched, substituted or unsubstituted heteroalkynyl; substituted or unsubstituted aryl; substituted or unsubstituted heteroaryl; nitro; cyano; azido; hydrazino; halo; isocyano; or two $R^Z$ groups are joined to form (=O), (=S), or (=NR$^R$), wherein $R^R$ is hydrogen; a suitable amino protecting group; substituted or unsubstituted amino; acyl; cyclic or acylic, branched or unbranched, substituted or unsubstituted alkyl; cyclic or acylic, branched or unbranched, substituted or unsubstituted alkenyl; cyclic or acylic, branched or unbranched, substituted or unsubstituted alkynyl; cyclic or acylic, branched or unbranched, substituted or unsubstituted heteroalkyl; cyclic or acylic, branched or unbranched, substituted or unsubstituted heteroalkenyl; cyclic or acylic, branched or unbranched, substituted or unsubstituted heteroalkynyl; or substituted or unsubstituted aryl; or substituted or unsubstituted heteroaryl; and
each instance of a is, independently, 1 to 20.

In certain embodiments, each instance of a is, independently, 1 to 15. In certain embodiments, each instance of a is, independently, 1 to 10. In certain embodiments, each instance of a is, independently, 1 to 5. In certain embodiments, each instance of a is 1.

In certain embodiments, Z corresponds to the formula:

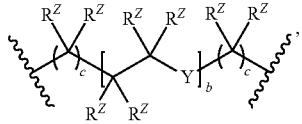

wherein
$R^Z$ is defined as described herein;
Y is —O—, —S—, or —N(R$^Y$)—, wherein $R^Y$ is a hydrogen; a suitable amino protecting group; acyl; cyclic or acylic, branched or unbranched, substituted or unsubstituted alkyl; cyclic or acylic, branched or unbranched, substituted or unsubstituted alkenyl; cyclic or acylic, branched or unbranched, substituted or unsubstituted alkynyl; cyclic or acylic, branched or unbranched, substituted or unsubstituted heteroalkyl; cyclic or acylic, branched or unbranched, substituted or unsubstituted heteroalkenyl; cyclic or acylic, branched or unbranched, substituted or unsubstituted heteroalkynyl; substituted or unsubstituted aryl; or substituted or unsubstituted heteroaryl;
b is, independently, 1 to 20; and
each instance of c is, independently, 0 to 10.

In certain embodiments, b is 1 to 10. In certain embodiments, b is 1 to 5. In certain embodiments, b is 1 to 2.

In certain embodiments, c is 1 to 10. In certain embodiments, c is 1 to 5. In certain embodiments, c is 1 to 3. In certain embodiments, c is 0.

In certain embodiments, at least one $R^Z$ is a —CHO group.
In certain embodiments, at least one $R^Z$ is a —CO$_2$H group.
In certain embodiments, at least one $R^Z$ is a —CO$_2$R$^{F1}$ group, wherein $R^{F1}$ is hydrogen; acyl; a suitable carboxylic acid protecting group; cyclic or acylic, branched or unbranched, substituted or unsubstituted alkyl; cyclic or acylic, branched or unbranched, substituted or unsubstituted alkenyl; cyclic or acylic, branched or unbranched, substituted or unsubstituted alkynyl; cyclic or acylic, branched or unbranched, substituted or unsubstituted heteroalkyl; cyclic or acylic, branched or unbranched, substituted or unsubstituted heteroalkenyl; cyclic or acylic, branched or unbranched, substituted or unsubstituted heteroalkynyl; substituted or unsubstituted aryl; or substituted or unsubstituted heteroaryl.

In certain embodiments, at least one $R^Z$ is a —C(O)N(R$^{F2}$)(R$^{F3}$) group, wherein each instance of $R^{F2}$ and $R^{F3}$ is, independently, hydrogen; acyl; substituted or unsubstituted amino; cyclic or acylic, branched or unbranched, substituted or unsubstituted alkyl; cyclic or acylic, branched or unbranched, substituted or unsubstituted alkenyl; cyclic or acylic, branched or unbranched, substituted or unsubstituted alkynyl; cyclic or acylic, branched or unbranched, substituted or unsubstituted heteroalkyl; cyclic or acylic, branched or unbranched, substituted or unsubstituted heteroalkenyl; cyclic or acylic, branched or unbranched, substituted or unsubstituted heteroalkynyl; substituted or unsubstituted aryl; or substituted or unsubstituted heteroaryl.

In certain embodiments, at least one $R^Z$ is a substituted or unsubstituted hydroxyl group. In certain embodiments, at least one $R^Z$ is a —CHO group and at least one $R^Z$ is a hydroxyl group. In certain embodiments, at least one $R^Z$ is a —CO$_2$H group or a —CO$_2$R$^{F1}$ group and at least one $R^Z$ is a substituted or unsubstituted hydroxyl group. In certain embodiments, at least one $R^Z$ is a —C(O)N(R$^{F2}$)(R$^{F3}$) group and at least one $R^Z$ is a substituted or unsubstituted hydroxyl group.

For example, in certain embodiments, Z corresponds to the formulae:

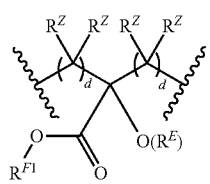

wherein $R^E$ is hydrogen or a suitable hydroxyl protecting group;
each instance of d is, independently, 0 to 10, and
$R^Z$, and $R^{F1}$ are defined above and herein.

Additionally, in certain embodiments, Z corresponds to the formulae:

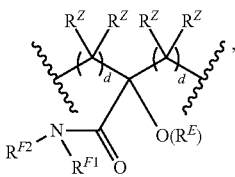

wherein d, $R^E$, $R^Z$, $R^{F2}$ and $R^{F3}$ are defined above and herein.

In certain embodiments, Z corresponds to the formula:

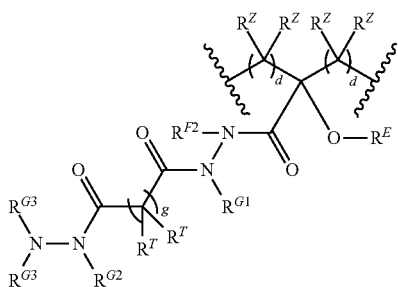

wherein:

each instance of $R^T$ is, independently, hydrogen; acyl; substituted or unsubstituted amino; substituted or unsubstituted hydroxyl; substituted or unsubstituted thiol; acylic, branched or unbranched, substituted or unsubstituted alkyl; cyclic or acyclic, branched or unbranched, substituted or unsubstituted alkenyl; cyclic or acyclic, branched or unbranched, substituted or unsubstituted alkynyl; cyclic or acyclic, branched or unbranched, substituted or unsubstituted heteroalkyl; cyclic or acyclic, branched or unbranched, substituted or unsubstituted heteroalkenyl; cyclic or acyclic, branched or unbranched, substituted or unsubstituted heteroalkynyl; substituted or unsubstituted aryl; substituted or unsubstituted heteroaryl, nitro; cyano; azido; hydrazino; halo; isocyano;

each instance of $R^{G1}$ and $R^{G2}$ is, independently, hydrogen; acyl; substituted or unsubstituted amino; a suitable amino protecting group; cyclic or acyclic, branched or unbranched, substituted or unsubstituted alkyl; cyclic or acyclic, branched or unbranched, substituted or unsubstituted alkenyl; cyclic or acyclic, branched or unbranched, substituted or unsubstituted alkynyl; cyclic or acyclic, branched or unbranched, substituted or unsubstituted heteroalkyl; cyclic or acyclic, branched or unbranched, substituted or unsubstituted heteroalkenyl; cyclic or acyclic, branched or unbranched, substituted or unsubstituted heteroalkynyl; substituted or unsubstituted aryl; or substituted or unsubstituted heteroaryl;

each instance of $R^{G3}$ is, independently, hydrogen; acyl; substituted or unsubstituted amino; a suitable amino protecting group; cyclic or acyclic, branched or unbranched, substituted or unsubstituted alkyl; cyclic or acyclic, branched or unbranched, substituted or unsubstituted alkenyl; cyclic or acyclic, branched or unbranched, substituted or unsubstituted alkynyl; cyclic or acyclic, branched or unbranched, substituted or unsubstituted heteroalkyl; cyclic or acyclic, branched or unbranched, substituted or unsubstituted heteroalkenyl; cyclic or acyclic, branched or unbranched, substituted or unsubstituted heteroalkynyl; or substituted or unsubstituted aryl, or two $R^{G3}$ groups are joined to form a doubled bond substituted with acyl; cyclic or acylic, branched or unbranched, substituted or unsubstituted alkyl; cyclic or acyclic, branched or unbranched, substituted or unsubstituted alkenyl; cyclic or acyclic, branched or unbranched, substituted or unsubstituted alkynyl; cyclic or acyclic, branched or unbranched, substituted or unsubstituted heteroalkyl; cyclic or acyclic, branched or unbranched, substituted or unsubstituted heteroalkenyl; cyclic or acyclic, branched or unbranched, substituted or unsubstituted heteroalkynyl; substituted or unsubstituted aryl; or substituted or unsubstituted heteroaryl.

g is 1 to 20, and wherein d, $R^E$, $R^{F2}$, $R^Z$, are defined above and herein.

In certain embodiments, the group

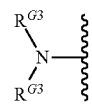

corresponds to the group:

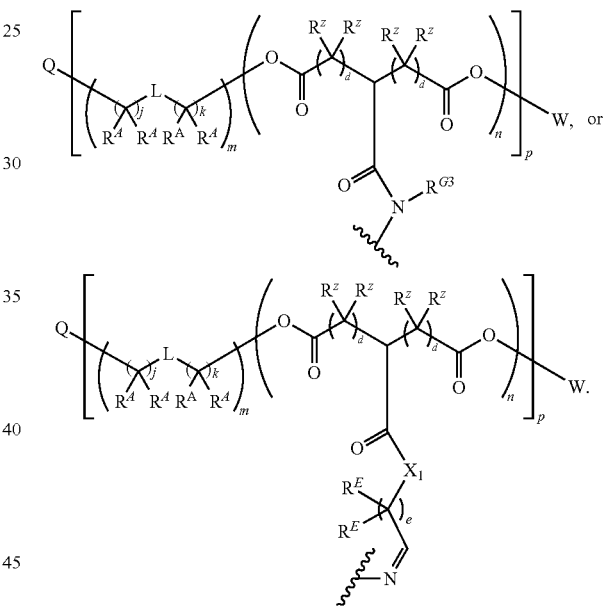

wherein e is 1 to 10;

$X_1$ is $-(CR^{X1})_2-$, $-O-$, $-S-$, or $-N(R^{X2})-$, wherein $R^{X1}$ is a hydrogen; acyl; cyclic or acyclic, branched or unbranched, substituted or unsubstituted alkyl; cyclic or acyclic, branched or unbranched, substituted or unsubstituted alkenyl; cyclic or acyclic, branched or unbranched, substituted or unsubstituted alkynyl; cyclic or acyclic, branched or unbranched, substituted or unsubstituted heteroalkyl; cyclic or acyclic, branched or unbranched, substituted or unsubstituted heteroalkenyl; cyclic or acyclic, branched or unbranched, substituted or unsubstituted heteroalkynyl; substituted or unsubstituted aryl; or substituted or unsubstituted heteroaryl, and $R^{X2}$ is a hydrogen; a suitable amino protecting group; acyl; cyclic or acyclic, branched or unbranched, substituted or unsubstituted alkyl; cyclic or acyclic, branched or unbranched, substituted or unsubstituted alkenyl; cyclic or acyclic, branched or unbranched, substituted or unsubstituted alkynyl; cyclic or acyclic, branched or unbranched, substituted or unsubstituted heteroalkyl; cyclic or acylic, branched or unbranched, substituted or unsubstituted heteroalkenyl; cyclic or acylic, branched or unbranched, substituted or unsubstituted heteroalkynyl; substituted or unsubstituted aryl; or substituted or unsubstituted heteroaryl; and each instance of $R^E$ is, independently, a hydrogen; substituted or unsubstituted hydroxyl; substituted or unsubstituted thiol; substituted or unsubstituted amino; acyl; cyclic or acylic, branched or unbranched, substituted or unsubstituted alkyl; cyclic or acylic, branched or unbranched, substituted or unsubstituted alkenyl; cyclic or acylic, branched or unbranched, substituted or unsubstituted alkynyl; cyclic or acylic, branched or unbranched, substituted or unsubstituted heteroalkyl; cyclic or acylic, branched or unbranched, substituted or unsubstituted heteroalkenyl; cyclic or acylic, branched or unbranched, substituted or unsubstituted heteroalkynyl; substituted or unsubstituted aryl; substituted or unsubstituted heteroaryl; cyano; isocyano; nitro; halo; hydrazino; or azido.

In certain embodiments, Z corresponds to the formula:

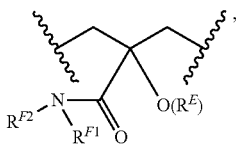

wherein $R^E$, $R^{F2}$, and $R^{F3}$ are described above and herein.

In certain embodiments, Z corresponds to the formulae:

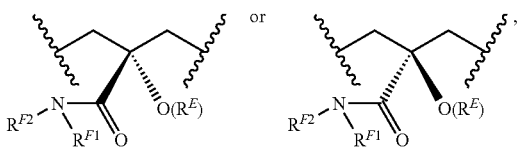

wherein $R^E$, $R^{F2}$, and $R^{F3}$ are described above and herein.

In certain embodiments, Z corresponds to the formula:

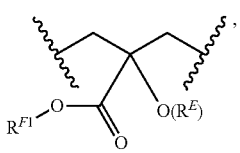

wherein $R^E$ and $R^{F1}$ are described above and herein.

In certain embodiments, Z corresponds to the formulae:

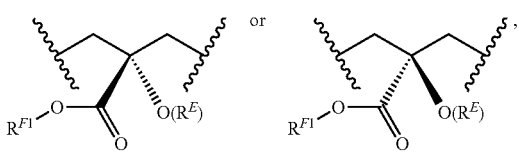

wherein $R^E$ and $R^{F1}$ are described above and herein.

In certain embodiments, L is cyclic or acylic, branched or unbranched, substituted or unsubstituted $C_{1-20}$ alkylene; cyclic or acylic, branched or unbranched, substituted or unsubstituted $C_{1-20}$ alkenylene; cyclic or acylic, branched or unbranched, substituted or unsubstituted $C_{1-20}$ alkynylene; cyclic or acylic, branched or unbranched, substituted or unsubstituted $C_{1-20}$ heteroalkylene; cyclic or acylic, branched or unbranched, substituted or unsubstituted $C_{1-20}$ heteroalkenylene; cyclic or acylic, branched or unbranched, substituted or unsubstituted $C_{1-20}$ heteroalkynylene; or substituted or unsubstituted $C_{1-20}$ acylene.

In certain embodiments, L is cyclic or acylic, branched or unbranched, substituted or unsubstituted $C_{1-15}$ alkylene; cyclic or acylic, branched or unbranched, substituted or unsubstituted $C_{1-15}$ alkenylene; cyclic or acylic, branched or unbranched, substituted or unsubstituted $C_{1-15}$ alkynylene; cyclic or acylic, branched or unbranched, substituted or unsubstituted $C_{1-15}$ heteroalkylene; cyclic or acylic, branched or unbranched, substituted or unsubstituted $C_{1-15}$ heteroalkenylene; cyclic or acylic, branched or unbranched, substituted or unsubstituted $C_{1-15}$ heteroalkynylene; or substituted or unsubstituted $C_{1-15}$ acylene.

In certain embodiments, L is a cyclic or acylic, branched or unbranched, substituted or unsubstituted $C_{1-10}$ alkylene; cyclic or acylic, branched or unbranched, substituted or unsubstituted $C_{1-10}$ alkenylene; cyclic or acylic, branched or unbranched, substituted or unsubstituted $C_{1-10}$ alkynylene; cyclic or acylic, branched or unbranched, substituted or unsubstituted $C_{1-10}$ heteroalkylene; cyclic or acylic, branched or unbranched, substituted or unsubstituted $C_{1-10}$ heteroalkenylene; cyclic or acylic, branched or unbranched, substituted or unsubstituted $C_{1-10}$ heteroalkynylene; or substituted or unsubstituted $C_{1-10}$-acylene.

In certain embodiments, L is cyclic or acylic, branched or unbranched, substituted or unsubstituted $C_{5-10}$ alkylene; cyclic or acylic, branched or unbranched, substituted or unsubstituted $C_{5-10}$ alkenylene; cyclic or acylic, branched or unbranched, substituted or unsubstituted $C_{5-10}$ alkynylene; cyclic or acylic, branched or unbranched, substituted or unsubstituted $C_{5-10}$ heteroalkylene; cyclic or acylic, branched or unbranched, substituted or unsubstituted $C_{5-10}$ heteroalkenylene; cyclic or acylic, branched or unbranched, substituted or unsubstituted $C_{5-10}$ heteroalkynylene; or substituted or unsubstituted $C_{5-10}$ acylene.

As used herein, when L is "hydroxylated," at least one carbon atom of L is substituted with a substituted or unsubstituted hydroxyl group. As used herein, when L is "partially-hydroxylated," at least one carbon atom of L is not substituted with a substituted or unsubstituted hydroxyl group, and at least one carbon atom of L is substituted with a substituted or unsubstituted hydroxyl group. As used herein, when L is "fully-hydroxylated," every carbon atom of L is substituted with a substituted or unsubstituted hydroxyl group. Thus, in certain embodiments, L is hydroxylated; in certain embodiments, L is partially-hydroxylated; and, in certain embodiments, L is fully-hydroxylated.

For example, in certain embodiments, L is cyclic or acylic, branched or unbranched, hydroxylated $C_{1-20}$ alkylene; cyclic or acylic, branched or unbranched, hydroxylated $C_{1-20}$ alkenylene; cyclic or acylic, branched or unbranched, hydroxylated $C_{1-20}$ alkynylene; cyclic or acylic, branched or unbranched, hydroxylated $C_{1-20}$ heteroalkylene; cyclic or acylic, branched or unbranched, hydroxylated $C_{1-20}$ heteroalkenylene; cyclic or acylic, branched or unbranched, hydroxylated $C_{1-20}$ heteroalkynylene; or hydroxylated $C_{1-20}$ acylene.

In certain embodiments, L is cyclic or acylic, branched or unbranched, hydroxylated $C_{1-15}$ alkylene; cyclic or acylic, branched or unbranched, hydroxylated $C_{1-15}$ alkenylene; cyclic or acylic, branched or unbranched, hydroxylated $C_{1-15}$ alkynylene; cyclic or acylic, branched or unbranched, hydroxylated $C_{1-15}$ heteroalkylene; cyclic or acylic, branched or unbranched, hydroxylated $C_{1-15}$ heteroalkenylene; cyclic or acylic, branched or unbranched, hydroxylated $C_{1-15}$ heteroalkynylene; or hydroxylated $C_{1-15}$ acylene.

In certain embodiments, L is a cyclic or acylic, branched or unbranched, hydroxylated $C_{1-10}$ alkylene; cyclic or acylic, branched or unbranched, hydroxylated $C_{1-10}$ alkenylene; cyclic or acylic, branched or unbranched, hydroxylated $C_{1-10}$ alkynylene; cyclic or acylic, branched or unbranched, hydroxylated $C_{1-10}$ heteroalkylene; cyclic or acylic, branched or unbranched, hydroxylated $C_{1-10}$ heteroalkenylene; cyclic or acylic, branched or unbranched, hydroxylated $C_{1-10}$ heteroalkynylene; or hydroxylated $C_{1-10}$ acylene.

In certain embodiments, L is cyclic or acylic, branched or unbranched, hydroxylated $C_{5-10}$ alkylene; cyclic or acylic, branched or unbranched, hydroxylated $C_{5-10}$ alkenylene; cyclic or acylic, branched or unbranched, hydroxylated $C_{5-10}$ alkynylene; cyclic or acylic, branched or unbranched, hydroxylated $C_{5-10}$ heteroalkylene; cyclic or acylic, branched or unbranched, hydroxylated $C_{5-10}$ heteroalkenylene; cyclic or acylic, branched or unbranched, hydroxylated $C_{5-10}$ heteroalkynylene; or hydroxylated $C_{5-10}$ acylene.

In certain embodiments, L is acyclic.

In certain embodiments, L is unbranched.

In certain embodiments, L is hydroxylated, partially hydroxylated, or fully hydroxylated. For example, in certain embodiments, L corresponds to the formulae:

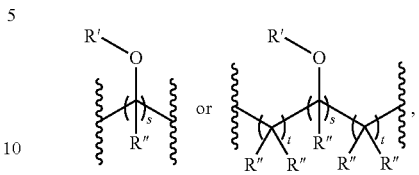

wherein:
each instance of s is, independently, 1 to 6;
each instance of t is, independently, 0 to 5;
each instance of R' is, independently, hydrogen; a suitable hydroxyl protecting group; acyl; cyclic or acylic, branched or unbranched, substituted or unsubstituted alkyl; cyclic or acylic, branched or unbranched, substituted or unsubstituted alkenyl; cyclic or acylic, branched or unbranched, substituted or unsubstituted alkynyl; cyclic or acylic, branched or unbranched, substituted or unsubstituted heteroalkyl; cyclic or acylic, branched or unbranched, substituted or unsubstituted heteroalkenyl; or cyclic or acylic, branched or unbranched, substituted or unsubstituted heteroalkynyl; substituted or unsubstituted aryl; or substituted or unsubstituted heteroaryl; or R' corresponds to the formulae:

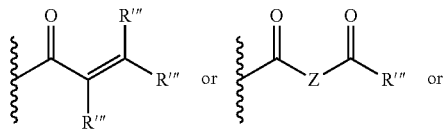

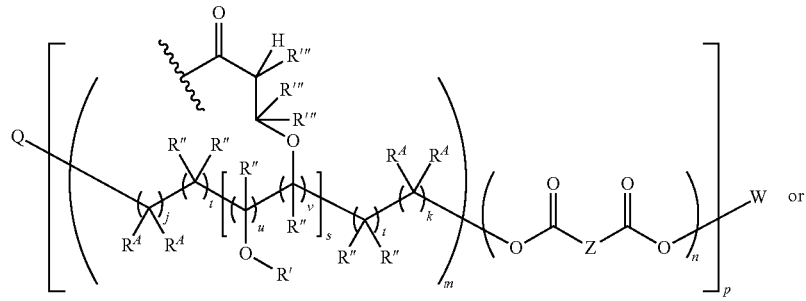

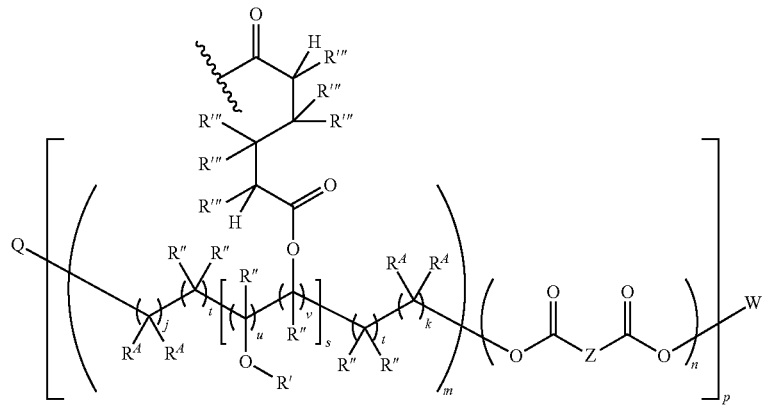

wherein:
each instance of u is, independently, 0 to 5;
each instance of v is, independently, 1 to 6;
each instance of R''' is, independently, hydrogen; acyl; cyclic or acylic, branched or unbranched, substituted or unsubstituted alkyl; cyclic or acylic, branched or unbranched, substituted or unsubstituted alkenyl; cyclic or acylic, branched or unbranched, substituted or unsubstituted alkynyl; cyclic or acylic, branched or unbranched, substituted or unsubstituted heteroalkyl; cyclic or acylic, branched or unbranched, substituted or unsubstituted heteroalkenyl; cyclic or acylic, branched or unbranched, substituted or unsubstituted heteroalkynyl; or substituted or unsubstituted aryl;

each instance of R''' is, independently, hydrogen; halo; cyclic or acylic, branched or unbranched, substituted or unsubstituted alkyl; cyclic or acylic, branched or unbranched, substituted or unsubstituted alkenyl; cyclic or acylic, branched or unbranched, substituted or unsubstituted alkynyl; cyclic or acylic, branched or unbranched, substituted or unsubstituted heteroalkyl; cyclic or acylic, branched or unbranched, substituted or unsubstituted heteroalkenyl; or cyclic or acylic, branched or unbranched, substituted or unsubstituted heteroalkynyl; substituted or unsubstituted aryl; or substituted or unsubstituted heteroaryl;

each instance of R'''' is —(OR$^X$), wherein R$^X$ is hydrogen; a suitable carboxylic acid protecting group; acyl; cyclic or acylic, branched or unbranched, substituted or unsubstituted alkyl; cyclic or acylic, branched or unbranched, substituted or unsubstituted alkenyl; cyclic or acylic, branched or unbranched, substituted or unsubstituted alkynyl; cyclic or acylic, branched or unbranched, substituted or unsubstituted heteroalkyl; cyclic or acylic, branched or unbranched, substituted or unsubstituted heteroalkenyl; or cyclic or acylic, branched or unbranched, substituted or unsubstituted heteroalkynyl; substituted or unsubstituted aryl; or substituted or unsubstituted heteroaryl; or R'''' corresponds to the formula:

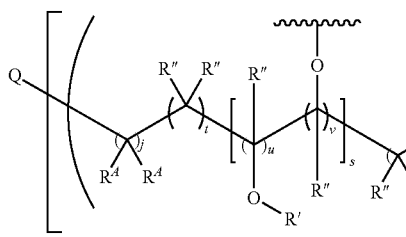

and wherein L, Q, W, R', R'', R$^A$, R$^Z$, R$^T$, R$^{G1}$, R$^{G2}$, R$^{G3}$, g, s, t, m, n, j, k, p, and g, are defined above and herein.

In certain embodiments, the ratio of m to n is about 1:1; 2:1; 3:1; 4:5:1; 6:1; 7:1; 8:1; 9:1; or 10:1. In certain embodiments, the ratio of m to n is 1:2; 1:3; 1:4; 1:5; 1:6; 1:7; 1:8; 1:9; or 1:10. In certain embodiments, the ratio of m to n is 2:3, 3:2, 3:4, or 4:3. In certain embodiments, the polymer is the result of a mixture of two or more different ratios. The ratio of m to n, inherently, represents the ratio of polyol to polycarboxylic acid used to form the inventive polymer.

In certain embodiments, R' is hydrogen. In certain embodiments, R'' is hydrogen.

In certain embodiments, t is 0. In certain embodiments, each instance of s is, independently, 2 to 6. In certain embodiments, each instance of s is, independently, 2 to 5. In certain embodiments, each instance of s is, independently, 2 to 4. In certain embodiments, s is 3 to 5. In certain embodiments, s is 3.

In certain embodiments, L corresponds to the formulae:

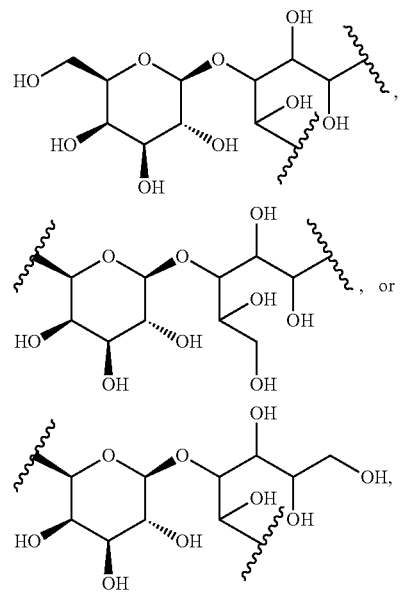

or L is a mixture thereof.

In certain embodiments, L corresponds to the formulae:

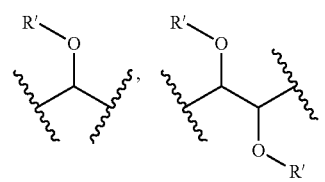

-continued

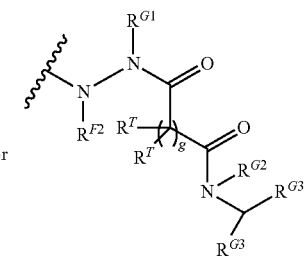

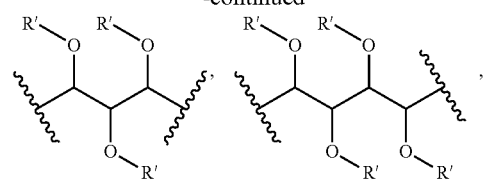

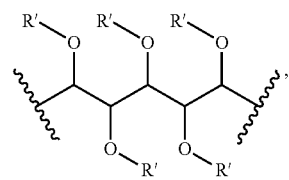

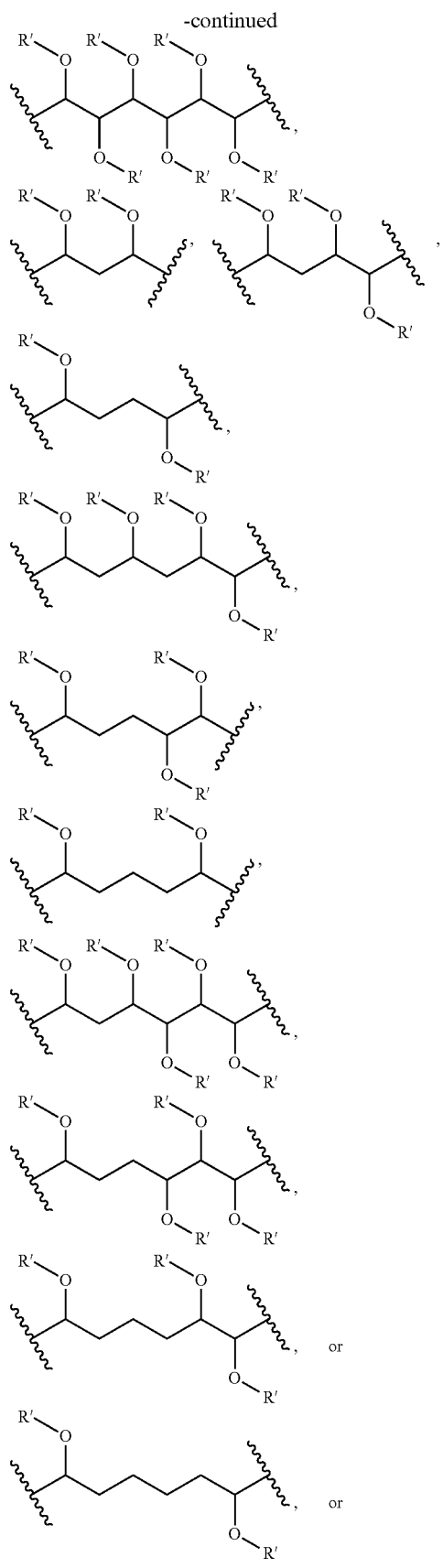
L is a mixture thereof,
wherein R' is defined above and herein.
In certain embodiments, L corresponds to the formulae:
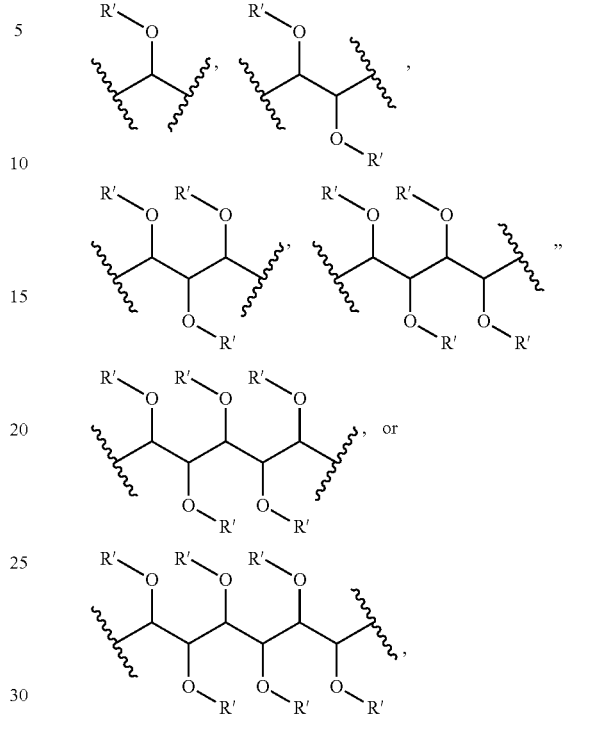
or L is a mixture thereof, wherein R' is defined above and herein.
In certain embodiments, L corresponds to the formulae:
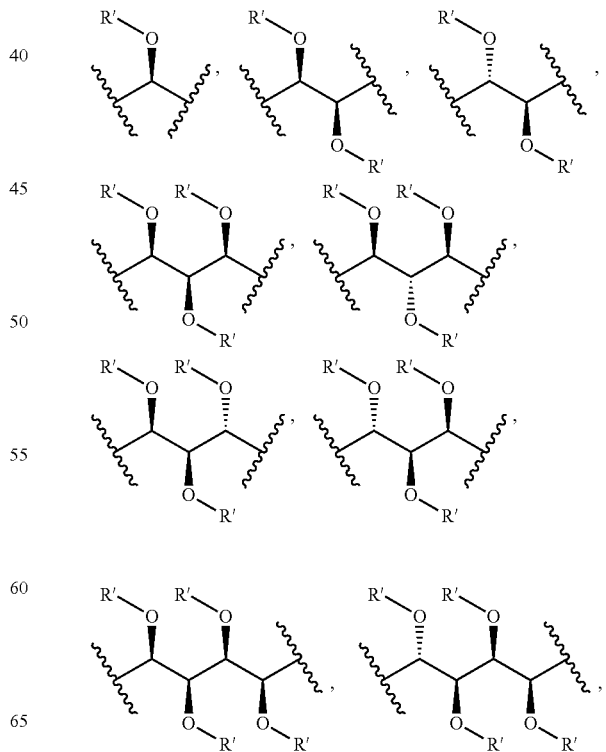

-continued

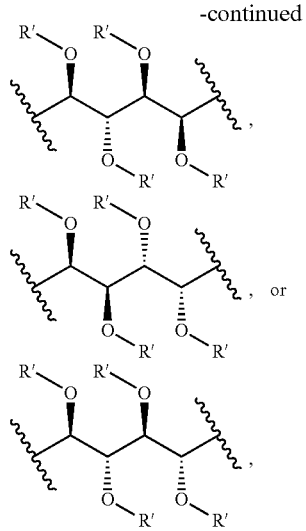

or L is a mixture thereof, wherein R' is defined above and herein.

In certain embodiments, L corresponds to the formula:

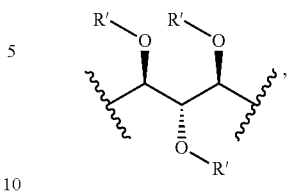

wherein R' is defined above and herein.

In certain embodiments, L corresponds to a polyol selected from Table 1 (provided below). In certain embodiments, L corresponds to a polyol selected from glycerol, erythritol, threitol, ribitol, arabinitol, xylitol, allitol, altritol, galactritol, sorbitol, mannitol, iditol, lactitol, isomalt, or maltitol, wherein the functional groups present on the polyol are optionally substituted, as described above. In certain embodiments, L corresponds to a polyol selected from xylitol, mannitol, sorbitol, or maltitol, wherein the functional groups present on the polyol are optionally substituted, as described above.

TABLE 1

Exemplary polyols

Sugar alcohols glycerol; glyceritol; Propane-1,2,3-triol erythritol threitol ribitol; adonitol arabinitol xylitol allitol altritol galacitol TABLE 1-continued Exemplary polyols

|   CH₂OH    |   CH₂OH    |   CH₂OH    |
|   H—OH     |   HO—H     |   HO—H     |
|   HO—H     |   HO—H     |   H—OH     |
|   H—OH,    |   H—OH,    |   H—OH,    |
|   H—OH     |   H—OH     |   H—OH     |
|   CH₂OH    |   CH₂OH    |   CH₂OH    |
| glucitol; sorbitol | mannitol | iditol |

Cyclic sugars  
Maltitol, lactitol, isomalt e.g., maltitol e.g., lactitol e.g., isomalt e.g., monosaccharides which include hexoses (allose, altrose, glucose, mannose, gulose, idose, galactose, talose) and pentoses (ribose, arabinaose, xylose, lyxose); disaccharides which include maltose, cellobiose. sucrose, and lactose; polysaccharides which include amylose, amylopectin, glycogen, and cellulose; fructofuranose, glucopyranose. sorbose, rhaminose, tagatose, apiose, deoxyribose, ribofructose, 1,3.6-tri-O-galloyl-β-D-glucopyranose (tannic acid); amino- containing cyclic sugars (e.g., N-acetyl glucoseamine (sialic acid), glucoseamine); amide-containing cyclic sugars (e.g., glucoronamide); carboxyl containing sugars (e.g., galacturonic acid); as well as protected derivatives, such as alkyl- and acyl-derivatives, and stereoisomers thereof.

Pentaerythritols, and structural derivatives thereof, such as methylated, ethylated, acetate, ethoxylale, and propoxylate derivatives.

e.g., pentaerythritol

TABLE 1-continued

Exemplary polyols

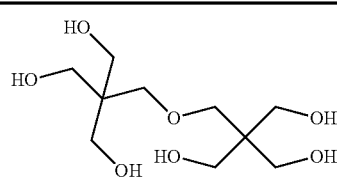

dipentaerythritol

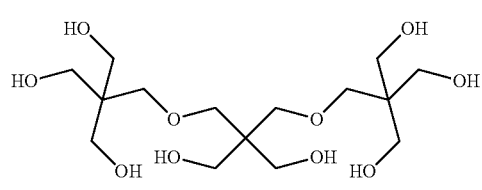

tripentaerythritol

| | |
|---|---|
| Phenolic polyols | e.g., resorcinol, orcinol, 2-methylresorcinol, phloroglucinol, 1,2,4 benzenetriol, pyrogallol, 4-ethylresorcinol. 5-methyl benzene 1,2,3triol, 2-methoxyhydroquinone, 3,5dihydroxylbenzyl alcohol, 2,4,6 trihydroxytoluene, 2,4,5-trihydroxybenzaldehyde, 2,3,4-trihydroxybenzaldehyde, 2,4,6,-trihydroxybenzaldehyde, gallacetophenone, 3,4,5-trihydroxybenzamide, gallic acid, 2,4,5-trihydroxybenzoic acid, 2,3,4-trihydroxybenzoic acid, 2-nitrophloroglucinol; naturally occurring phenolic compounds, such as carnosol, rosmanol (7α-), epirosmanol (7β-) from rosemary (Rosmarinus officialis L.); rosemaric acid from rosemary and oregano (Oreganum vulgare L.); capsicin and dihydrocapsicin, hot-lasting compounds, from hot pepper (Capsicinum annuum L.); ferulic acid amide of tyramine from black pepper (Piper nigrum L.); piperin-related compound from thyme (Thymus serpyllum L.); and apigenin and apiin from parsley |
| Miscellaneous polyols | e.g., |

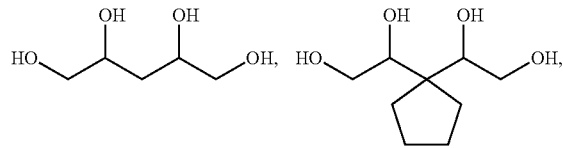 [SMILES: OCC(O)CC(O)CO ; OCC(O)C1(C(O)CO)CCCC1]

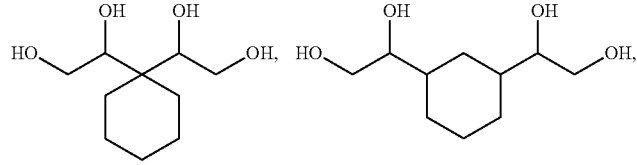 [SMILES: OCC(O)C1(C(O)CO)CCCCC1 ; OCC(O)C1CCCC(C(O)CO)C1]

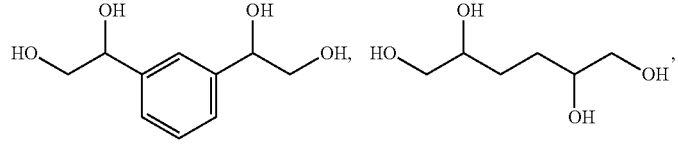 [SMILES: OCC(O)c1cccc(C(O)CO)c1 ; OCC(O)CCC(O)CO]

TABLE 1-continued

Exemplary polyols

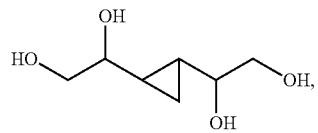

In certain embodiments, Z corresponds to a polycarboxylic acid selected from Table 2 (provided below). In certain embodiments, Z corresponds to a polycarboxylic acid selected from the group consisting of succinic acid, fumaric acid, α-ketoglutaric acid, oxaloacetic acid, malic acid, oxalosuccinic acid, isocitric acid, cis-aconitic acid, citric acid, 2-hydroxy-malonic acid, tartaric acid, ribaric acid, arabinaric acid, xylaric acid, allaric acid, altraric acid, galactaric acid, glucaric acid, or mannaric acid, dimercaptosuccinic acid, oxalic acid, malonic acid, succinic acid, glutaric acid, adipic acid, pimelic acid, suberic acid, azelaic acid, and sebacic acid, wherein the functional groups present on polycarboxylic acids are optionally substituted, as described above. In certain embodiments, Z corresponds to citric acid. In certain embodiments, Z corresponds to sebacic acid. In certain embodiments Z corresponds to a polycarboxylic acid selected from glutaric acid, citric acid and sebacic acid, wherein the functional groups present on polycarboxylic acids are optionally substituted, as described herein.

TABLE 2

| Exemplary Polycarboxylic Acids | |
|---|---|
| Oxalic acid | 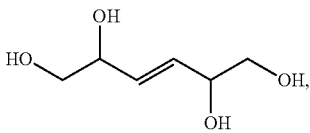 |
| Malonic acid (propanedioic acid) | 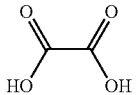 |
| Succinic acid, succinate (butanedioic acid) | 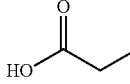 |
| Glutaric acid (pentanedioic acid) | 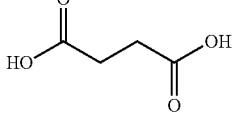 |
| Adipic acid (hexanedioic acid) | 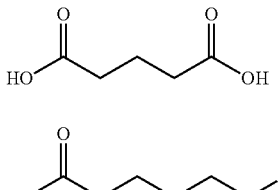 |
| Pimelic acid (heptanedioic acid) | 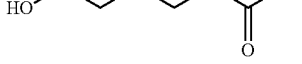 |
| Suberic acid (octanedioic acid) | 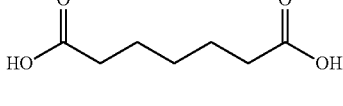 |
| Azelaic acid (nonanedioic acid) | 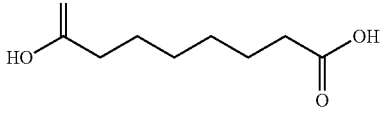 |

TABLE 2-continued

Exemplary Polycarboxylic Acids

Sebaic acid
(decanedioic acid)

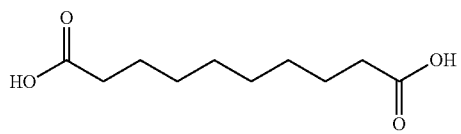 [SMILES: O=C(O)CCCCCCCCC(=O)O]

Aldaric acids

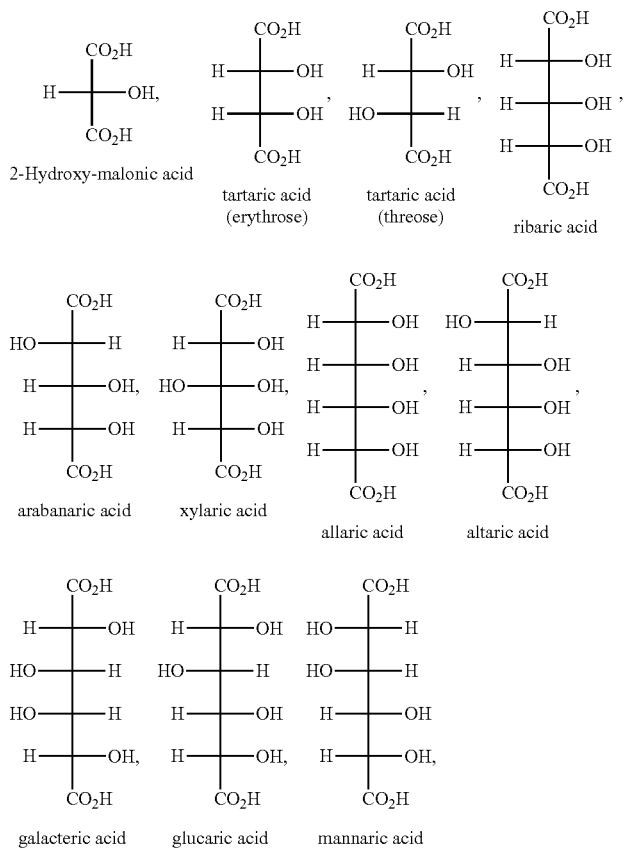

2-Hydroxy-malonic acid, tartaric acid (erythrose), tartaric acid (threose), ribaric acid arabanaric acid, xylaric acid, allaric acid, altaric acid galacteric acid, glucaric acid, mannaric acid Aspartic acid

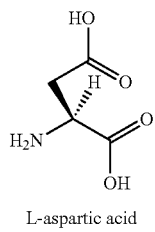

L-aspartic acid

DMSA
(Dimercapto-succinic acid, 2,3-bis-sulfanylbutanedioic acid)

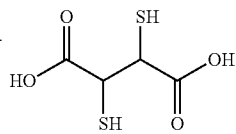

fumaric acid

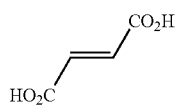

maleic acid

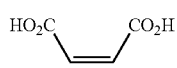

TABLE 2-continued

Exemplary Polycarboxylic Acids glutaconic acid

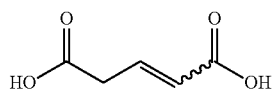

glutamic
Acid, Gln, Glutamate

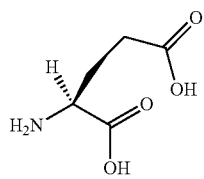

α-ketoglutaric acid;
Oxopentanedioic acid;

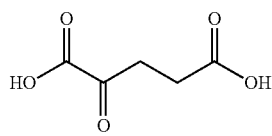

β-ketoglutaric acid

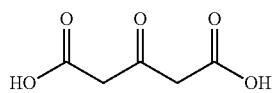

Oxaloacetic acid;
Oxaloacetate;

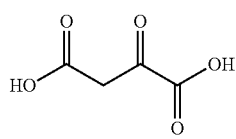

Malic acid;
Malate; hydroxysuccinic acid

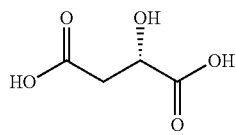

e.g., L-Malic acid fumaric acid;
fumarate

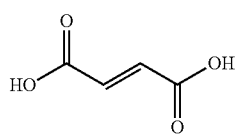

oxalosuccinic acid:
oxalosuccinate

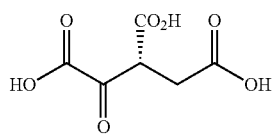 [SMILES: O=C(O)C[C@@H](C(=O)O)C(=O)C(=O)O]

isocitric acid:
isocitrate

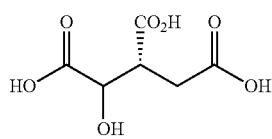 [SMILES: O=C(O)C[C@@H](C(=O)O)C(O)C(=O)O]

cis-aconitic acid

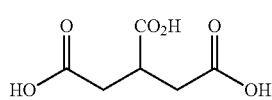

Citric acid;
citrate

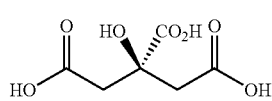

TABLE 2-continued

Exemplary Polycarboxylic Acids

Itaconic acid: methylenesuccininc acid

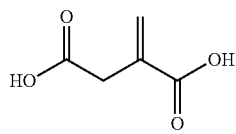

mesaconic acid: (2E)-2-Methyl-2-butenedioic acid

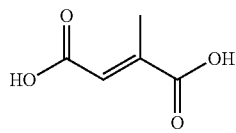

Tartaric acid, 2-3-dihydroxybutanedioic acid,, 3-dihydroxysuccinic acid; thearic acid; uvic acid; paratartaric acid

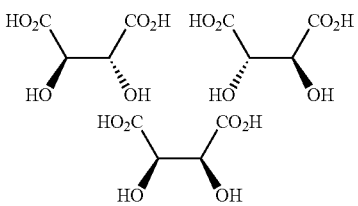

Traumatic acid; dodec-2-enedioic acid

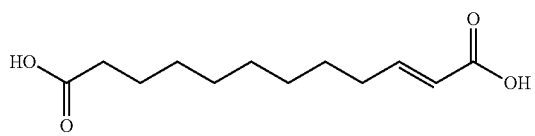 [SMILES: O=C(O)/C=C/CCCCCCCCC(=O)O]

In certain embodiments, the polymer is of the formula:

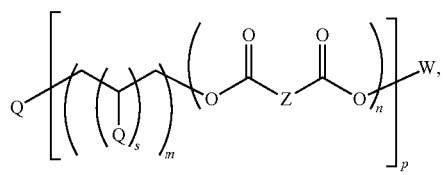

wherein:

each instance of Z, is, independently, cyclic or acylic, branched or unbranched, substituted or unsubstituted alkylene; cyclic or acylic, branched or unbranched, substituted or unsubstituted alkenylene; cyclic or acylic, branched or unbranched, substituted or unsubstituted alkynylene; cyclic or acylic, branched or unbranched, substituted or unsubstituted heteroalkylene; cyclic or acylic, branched or unbranched, substituted or unsubstituted heteroalkenylene; cyclic or acylic, branched or unbranched, substituted or unsubstituted heteroalkynylene; substituted or unsubstituted arylene; substituted or unsubstituted heteroarylene; or substituted or unsubstituted acylene;

W is hydrogen, or a suitable carboxylic acid protecting group;

Q is —$OR^C$, wherein $R^C$ is hydrogen; a suitable hydroxyl protecting group; acyl; cyclic or acylic, branched or unbranched, substituted or unsubstituted alkyl; cyclic or acylic, branched or unbranched, substituted or unsubstituted alkenyl; cyclic or acylic, branched or unbranched, substituted or unsubstituted alkynyl; cyclic or acylic, branched or unbranched, substituted or unsubstituted heteroalkyl; cyclic or acylic, branched or unbranched, substituted or unsubstituted heteroalkenyl; cyclic or acylic, branched or unbranched, substituted or unsubstituted heteroalkynyl; substituted or unsubstituted aryl; or substituted or unsubstituted heteroaryl;

or Q corresponds to the formula:

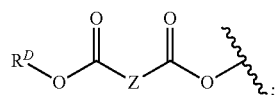

wherein:

$R^D$ is hydrogen or a suitable carboxylic acid protecting group;

each instance of s is, independently, 1 to 6;
each instance of m is, independently, 1 to 200;
each instance of n is, independently, 1 to 200; and
each instance of p is, independently, 1 to 1000.

In certain embodiments, the polymer is of the formula:

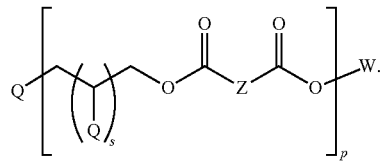

In certain embodiments, the polymer is of the formula:

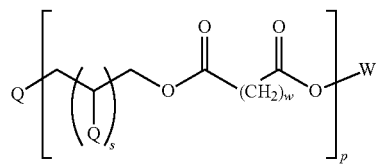

wherein each occurrence of w is 1 to 20, inclusive. In certain embodiments, w is 4. In certain embodiments, w is 6. In certain embodiments, w is 8. In certain embodiments, w is 10. In certain embodiments, w is 12. In certain embodiments, w is 14.

In certain embodiments, the polymer is based on the polyol xylitol is of the formula:

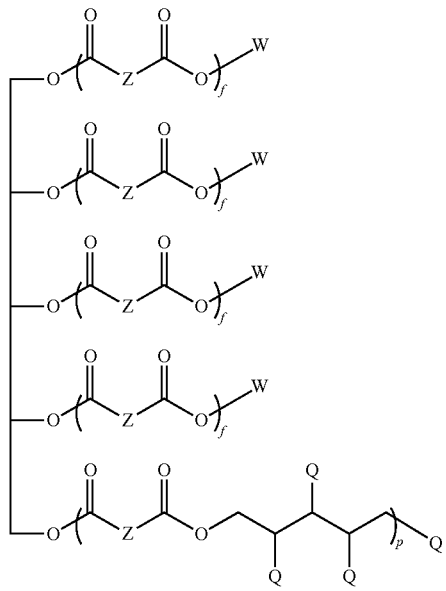

wherein each occurrence of f is an integer between 0 and 1, inclusive;

p is an integer between 1 and 1000, inclusive;

each occurrence of Q is, independently, —OR$^C$, wherein R$^C$ is hydrogen; a suitable hydroxyl protecting group; acyl; cyclic or acyclic, branched or unbranched, substituted or unsubstituted alkyl; cyclic or acyclic, branched or unbranched, substituted or unsubstituted alkenyl; cyclic or acyclic, branched or unbranched, substituted or unsubstituted alkynyl; cyclic or acyclic, branched or unbranched, substituted or unsubstituted heteroalkyl; cyclic or acyclic, branched or unbranched, substituted or unsubstituted heteroalkenyl; cyclic or acyclic, branched or unbranched, substituted or unsubstituted heteroalkynyl; substituted or unsubstituted aryl; or substituted or unsubstituted heteroaryl; or Q corresponds to the formula:

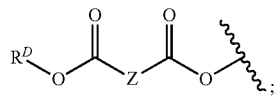

wherein R$^D$ is hydrogen or a suitable carboxylic acid protecting group;

each occurrence of Z is, independently, cyclic or acyclic, branched or unbranched, substituted or unsubstituted alkylene; cyclic or acyclic, branched or unbranched, substituted or unsubstituted alkenylene; cyclic or acyclic, branched or unbranched, substituted or unsubstituted alkynylene; cyclic or acyclic, branched or unbranched, substituted or unsubstituted heteroalkylene; cyclic or acyclic, branched or unbranched, substituted or unsubstituted heteroalkenylene; cyclic or acyclic, branched or unbranched, substituted or unsubstituted heteroalkynylene; substituted or unsubstituted arylene; substituted or unsubstituted heteroarylene; or substituted or unsubstituted acylene; and each occurrence of W is, independently, hydrogen or a suitable carboxylic acid protecting group. As would be appreciated by one of skill in the art, analogous polymers may be prepared using other polyols such as sorbitol or mannitol.

In another aspect, the present invention provides a branched polymer comprising alternating polyol and polycarboxylic acid units, wherein the polycarboxylic acid(s) used to form the polymer comprises at least two (2) carboxylic acid groups, and the polyol(s) used to form the polymer comprises at least three (3) hydroxyl groups. In certain embodiments, the branched polymer comprises one or more polyols. In certain embodiments, the branched polymer comprises one or more polycarboxylic acids.

In certain embodiments, the polyol(s) used to form the polymer has at least two (2) hydroxyl groups. In certain embodiments, the polyol(s) used to form the polymer has at least three (3) hydroxyl groups. In certain embodiments, the polyol(s) used to form the polymer has at least four (4) hydroxyl groups. In certain embodiments, the polyol(s) used to form the polymer has at least five (5) hydroxyl groups. In certain embodiments, the polyol(s) used to form the polymer has at least six (6) hydroxyl groups. In certain embodiments, the polyol(s) used to form the polymer has at least seven (7) hydroxyl groups. In certain embodiments, the polyol(s) used to form the polymer has at least eight (8) hydroxyl groups. In certain embodiments, the polyol(s) used to form the polymer includes between 3 to 10 hydroxyl groups. In certain embodiments, the polyol(s) used to form the polymer includes between 3 to 6 hydroxyl groups. Exemplary polyols used to form the inventive polymer include, but are not limited to, those depicted and listed in Table 1.

The polycarboxylic acid(s) used to form the polymer may further include at least two (2), three (3), four (4), five (5), or six (6) carboxylic acid groups. In certain embodiments, the polycarboxylic acid(s) used to form the polymer includes between two (2) to six (6) carboxylic acid groups. In certain embodiments, the polycarboxylic acid(s) used to form the polymer is a dicarboxylic acid (e.g., contains two carboxylic acid groups). In certain embodiments, the polycarboxylic acid(s) used to form the polymer is a tricarboxylic acid (e.g., contains three carboxylic acid groups). In certain embodiments, the polycarboxylic acid(s) is symmetrical. Exemplary polycarboxylic acids used to form the inventive polymer include, but are not limited to, those depicted and listed in Table 2.

In certain embodiments, the ratio of polyol to polycarboxylic acid (which also correspond to the variables m and n, respectively, in the formulae provided herein) in the polymer is about 1 to 1; 1 to 1.25; 1 to 1.5; 1 to 1.75; 1 to 2; 1 to 2.25; 1 to 2.50; 1 to 2.75; 1 to 3; 1 to 3.25; 1 to 3.50; 1 to 3.75; 1 to 4; 1 to 4.25; 1 to 4.50; 1 to 4.75; 1 to 5; 1 to 5.25; 1 to 5.50; 1 to 5.75; 1 to 6; 1 to 6.25; 1 to 6.50; 1 to 6.75; 1 to 7; 1 to 7.25; 1 to 7.50; 1 to 7.75; 1 to 8; 1 to 8.25; 1 to 8.50; 1 to 8.75; 1 to 9; 1 to 9.25; 1 to 9.50; 1 to 9.75; or 1 to 10 molecules of polyol to molecules of polycarboxylic acid.

In certain embodiments, the ratio of polyol to polycarboxylic acid in the polymer is 1 to 1.

In certain embodiments, the ratio of polyol to polycarboxylic acid in the polymer is 1 to 2.

In certain embodiments, the ratio of polyol to polycarboxylic acid (which also correspond to the variables m and n, respectively, in the formulae provided herein) in the polymer is about 2 to 1; 2.25 to 1; 2.50 to 1; 2.75 to 1; 3 to 1; 3.25 to 1;

3.50 to 1; 3.75 to 1; 4 to 1; 4.25 to 1; 4.50 to 1; 4.75 to 1; 5 to 1; 5.25 to 1; 5.50 to 1; 5.75 to 1; 6 to 1; 6.25 to 1; 6.50 to 1; 6.75 to 1; 7 to 1; 7.25 to 1; 7.50 to 1; 7.75 to 1; 8 to 1; 8.25 to 1; 8.50 to 1; 8.75 to 1; 9 to 1; 9.25 to 1; 9.50 to 1; 9.75 to 1; or 10 to 1 molecules of polyol to molecules of polycarboxylic acid.

In certain embodiments, wherein the inventive polymer comprises two different polyols, the two polyols may be present in a ratio of about 1 to 1; 1 to 1.25; 1 to 1.5; 1 to 1.75; 1 to 2; 1 to 2.25; 1 to 2.50; 1 to 2.75; 1 to 3; 1 to 3.25; 1 to 3.50; 1 to 3.75; 1 to 4; 1 to 4.25; 1 to 4.50; 1 to 4.75; 1 to 5; 1 to 5.25; 1 to 5.50; 1 to 5.75; 1 to 6; 1 to 6.25; 1 to 6.50; 1 to 6.75; 1 to 7; 1 to 7.25; 1 to 7.50; 1 to 7.75; 1 to 8; 1 to 8.25; 1 to 8.50; 1 to 8.75; 1 to 9; 1 to 9.25; 1 to 9.50; 1 to 9.75; or 1 to 10. In certain embodiments, the inventive polymer is a mixture of two or more ratios of polyols.

In certain embodiments, wherein the inventive polymer comprises two different polycarboxylic acids, the two polycarboxylic acids may be present in a ratio of about 1 to 1; 1 to 1.25; 1 to 1.5; 1 to 1.75; 1 to 2; 1 to 2.25; 1 to 2.50; 1 to 2.75; 1 to 3; 1 to 3.25; 1 to 3.50; 1 to 3.75; 1 to 4; 1 to 4.25; 1 to 4.50; 1 to 4.75; 1 to 5; 1 to 5.25; 1 to 5.50; 1 to 5.75; 1 to 6; 1 to 6.25; 1 to 6.50; 1 to 6.75; 1 to 7; 1 to 7.25; 1 to 7.50; 1 to 7.75; 1 to 8; 1 to 8.25; 1 to 8.50; 1 to 8.75; 1 to 9; 1 to 9.25; 1 to 9.50; 1 to 9.75; or 1 to 10. In certain embodiments, the inventive polymer is a mixture of two or more ratios of polycarboxylic acids.

The hydroxyl substituents present on the polyol used to form the polymer, and those which may, optionally, be present on the polycarboxylic acid unit, are either free hydroxyl groups (i.e., —OH) or are optionally substituted with an acyl group (such as an acrylate group, or an ester group formed from condensation with a polycarboxylic acid molecule), aliphatic, or a suitable hydroxyl protecting group. Additionally, two hydroxyl groups may be covalently conjugated to each other via a bridging acyl linkage, alkylene, or heteroalkylene linkage, and the two hydroxyl groups may be present on the same polymeric chain, or on different polymeric chains. In the case of the formation of a covalent bond or bridge between two different polymeric chains, the branched polymer may also be referred to as a "cross-linked polymer." In certain embodiments, the hydroxyl groups of the polyol and the polycarboxylic acid used to form the inventive polymer are free hydroxyl groups.

Additionally, one or more carboxylic acid substituents which may be present on a polycarboxylic acid unit may, optionally, be covalently conjugated via a bridging acyl linkage, alkylene, or heteroalkylene linkage, and the two carboxylic acid groups so joined may be present on the same polymeric chain, or on different polymeric chains. In the case of the formation of a covalent bond or bridge between two different polymeric chains, the branched polymer may also be referred to as a "cross-linked polymer." In certain embodiments, the hydroxyl groups of the polyol and the polycarboxylic acid used to form the inventive polymer are free hydroxyl groups.

The polyol and polycarboxylic acid used to form the polymer of the present invention, the polyol and/or the polycarboxylic acid may be present in its salt-free form, or may be a salt-form thereof. Exemplary pharmaceutically salts are described herein. Each of the polyols and polycarboxylic acids, as well, may be derivatives of known polyols and polycarboxylic acids; for example, a synthetic derivative (a carboxylic acid, an ester, an amide, and an acyl chloride are synthetic derivatives), or a synthetic analog. Derivatives and analogs may be synthesized from the inventive compound or polymer itself, or from other starting materials to make structural versions of the compound or polymer.

In certain aspects of the present invention, the polyol monomer used in the formation of the inventive polymer is an organic compound found in nature, or derived from nature. Such a compound can either be synthesized in a laboratory or isolated from natural sources. In certain embodiments, the polyol is endogenous to the human metabolic system. In certain embodiments, the polyol is non-toxic. In certain embodiments, the polyol is an optically enriched polyol. In certain embodiments, the polyol is an aliphatic polyol (i.e., does not contain arylene or heteroarylene groups).

In certain embodiments, the polyol is a food additive. Exemplary food additives include lactitol, isomalt, maltitol, and sugar alcohols. Exemplary sugar alcohols include glyceritol (i.e., glycerol), erythritol, threitol, ribitol, arabinitol, xylitol, allitol, altritol, galactritol, sorbitol, mannitol, and iditol.

In certain embodiments, the polyol is erythritol, threitol, ribitol, arabinitol, xylitol, allitol, altritol, galactritol, sorbitol, mannitol, iditol, lactitol, isomalt, or maltitol. In certain functions. Exemplary aldaric acids include 2-hydroxy-malonic acid, tartaric acid, ribaric acid, arabinaric acid, xylaric acid, allaric acid, altraric acid, galactaric acid, glucaric acid, or mannaric acid.

In certain embodiments, the polycarboxylic acid used in the formation of the inventive polymer comprises an optionally substituted alkanedioic acid. The term "alkanedioic acid," as used herein, refers to a dicarboxylic acid having the formula HO(O=)C—(CH$_2$)$_x$—C(=O)OH, wherein x is an integer of between 1 to 20, inclusive. When x is 1, the alkanedioic acid may be referred to as a "C$_1$ alkanedioic acid." When x is 20, the alkanedioic acid may be referred to as a "C$_{20}$ alkanedioic acid." In certain embodiments, the alkanedioic acid is a C$_1$-C$_{20}$ alkanedioic acid, a C$_1$-C$_{15}$ alkanedioic acid, a C$_1$-C$_{10}$ alkanedioic acid, a C$_1$-C$_{12}$ alkanedioic acid, a C$_1$-C$_{10}$ alkanedioic acid, a C$_5$-C$_{15}$ alkanedioic acid, a C$_5$-C$_{12}$ alkanedioic acid, a C$_5$-C$_{10}$ alkanedioic acid, or a C$_8$-C$_{12}$ alkanedioic acid. Exemplary alkanedioic acids include dimercaptosuccinic acid, oxalic acid, malonic acid, succinic acid, glutaric acid, adipic acid, pimelic acid, suberic acid, azelaic acid, or sebacic acid.

In certain embodiments, the polycarboxylic acid used in the formation of the inventive polymer comprises an optionally substituted alkenedioic acid. The term "alkenedioic acid," as used herein, refers to an alkanedioic acid, as defined herein, with at least one internal double bond, e.g., HO(O=)C—(CH=CH)$_z$—(CH$_2$)$_y$—C(=O)OH), wherein (2z+y) is an integer between 2 to 20. For example, when y is 0 and z is 1, the alkenedioic acid may be referred to as a "C$_2$ alkenedioic acid." When (2z+y) equals 20, the alkenedioic acid may be referred to as a "C$_{20}$ alkenedioic acid." Exemplary alkenedioic acids include fumaric acid, maleic acid, glutaconic acid, itaconic acid, mesaconic acid, or traumatic acid.

In certain embodiments, the polycarboxylic acid used in the formation of the inventive polymer is an optionally substituted glutaric acid, adipic acid, pimelic acid, suberic acid, azelaic acid, or sebacic acid. In certain embodiments, the polycarboxylic acid is optionally substituted glutaric acid. In certain embodiments, the polycarboxylic acid is optionally substituted sebacic acid. In certain embodiments, the polymer formed from an alkanedioic acid and the polyol glycerol is specifically excluded. In certain embodiments, the polymer formed from sebacic acid and the polyol glycerol is specifically excluded. In certain embodiments, the polymer formed from citric acid and the polyol glycerol is specifically excluded. Furthermore, in certain embodiments, the polymer formed from glutaric acid and the polyol glycerol is specifically excluded.

In certain embodiments, the inventive polymer comprises a polyol from Table 1, and a polycarboxylic acid from Table 2. In certain embodiments, the polyol is a sugar alcohol and the polycarboxylic acid is a metabolite, as described above and herein. In certain embodiments, the polyol is a sugar alcohol and the polycarboxylic acid is an optionally substituted alkanedioic acid, as described above and herein.

In certain embodiments, the polyol is xylitol, mannitol, sorbitol, or maltitol and the polycarboxylic acid is a metabolite. In certain embodiments, the polyol is xylitol, mannitol, sorbitol, or maltitol, and the polycarboxylic acid is citric acid.

In certain embodiments, the polyol is xylitol, mannitol, sorbitol, or maltitol and the polycarboxylic acid is an optionally substituted alkanedioic acid. In certain embodiments, the polyol is xylitol, mannitol, sorbitol, or maltitol and the polycarboxylic acid is optionally substituted glutaric acid. In certain embodiments, the polyol is xylitol, mannitol, sorbitol, or maltitol and the polycarboxylic acid is optionally substituted sebacic acid.

Properties of the Inventive Polymers

In certain aspects, the inventive polymer is biodegradable. In certain aspects, the inventive polymer is non-toxic. In certain embodiments, the inventive polymer, upon biodegrading, degrades to non-toxic products. In certain embodiments, the non-toxic products are endogenous to the human metabolic system. In certain embodiments, the non-toxic products are not harmful to the environment. In certain embodiments, the non-toxic products are not harmful to humans. In certain embodiments, the non-toxic products have been (or will be) approved by the U.S. Food and Drug Administration as safe for human consumption or medical applications.

Thus, in one aspect of the present invention, the inventive polymer, upon biodegrading, degrades to non-toxic alcohols. In certain embodiments, the non-toxic alcohols are sugar alcohols. In certain embodiments, the non-toxic alcohols are biologically active. In certain aspects, the activity of the biologically active alcohols comprise antimicrobial, antifungal, and/or antibacterial activity. In certain aspects, the biologically active alcohol is xylitol. The safety and administration of xylitol as a nutrient and medicament to humans has been well-documented (see, for example, Uhari et al., *Vaccine* (2001) 19:S144-S147; Pizzo et al., *Microbiologica* (2000) 23:63-71; Brown et al., *Laryngoscope* (2004) 114:2021-2024; Mattila et al., *Metabolism* (2002) 51:92-96; Mattila et al., *Journal of Nutrition*, (1998) 1811-1814; and Ly et al., *Pediatric Dentistry* (2006) 28:154-163).

In certain aspects, the inventive polymer is a substantially clear polymer. "Substantially clear" refers to a sample specimen with a light transmission percentage of at least 85%, or greater, and, optionally, when the refractive index is constant through the sample in the viewing direction. In certain embodiments, the light transmission percentage is at least about 85%, 90%, 95%, or 99%.

In certain aspects, the inventive polymer is pH responsive. As used herein "pH responsive" refers to a change in the physical properties (e.g., swelling-deswelling as the pH drops/rises; morphology; solubility; elasticity) of an inventive polymer as a result of a change in the pH of its environment. For example, an inventive polymer which is solubilized, partially-solubilized, or suspended in a suitable medium may be exposed to a change in the pH of the medium (the pH may be acidic, basic, or neutral). In certain embodiments, the suitable medium comprises water, a polar protic solvent such as water or alcohol (e.g., methanol, ethanol, isopropanol), a polar aprotic solvent (e.g., dimethylformamide (DMF), dimethylacetamide (DMA), dimethylsulfoxide (DMSO), N-methylpyrrolidinone (NMP)), ethers (e.g., diethyl ether, dioxane, tetrahydrofuran (THF)), halogenated hydrocarbons (e.g., dichloromethane (DCM), dichloroethane (DCE), chloroform), aromatic solvents (e.g., toluene, benzene), or a mixture thereof.

A polymer of the presently claimed invention may take on many different forms, properties, 3-dimensional shapes, and/or sizes. For example, in certain embodiments, the inventive polymer is a bead, microsphere, nanoparticle, pellet, matrix, mesh, gauze, strand, thread, fiber, film, or coating. In certain embodiments, the inventive polymer has a disc-like or spheroidal-like shape.

In certain embodiments, the inventive polymer is a plastic (e.g., is malleable, having the property of plasticity). In certain embodiments, the inventive polymer is a thermoplastic. In certain embodiments, the polymer is a thermoset polymer.

In certain embodiments, the inventive polymer is a paste or a wax or has a paste-like or wax-like consistency.

In certain embodiments, the inventive polymer is water soluble, or partially water soluble. In certain embodiments, the inventive polymer is not water soluble.

In certain embodiments, the inventive polymer is a hydrogel.

In certain embodiments, the inventive polymer is a stiff, hard biomaterial (e.g., is not malleable). In certain embodiments, the inventive polymer is a brittle biomaterial.

As used herein, a hydrogel is a polymer which absorbs at least about 10 wt % of water (in the presence of an abundance of water). In certain embodiments, the hydrogel polymer absorbs between about 10 to 100%, 10 to 90 wt %, 10 to 80 wt %, 10 to 70 wt %, 10 to 60 wt %, 10 to 50 wt %, 10 to 40 wt %, 10 to 30 wt %, 10 to 20 wt %, or 10 to 15 wt % of water. In certain embodiments, the hydrogel polymer has an in-vivo half life of between about 1 week to 2 years. In certain embodiments, the hydrogel has an in-vivo half life of at least about 1 week, 2 weeks, 3 weeks, 4 weeks, 2 months, 3 months, 4 months, 5 months, 6 months, 7 months, 8 months, 9 months, 10 months, 11 months, 1 year, 1.5 years, or 2 years. In certain embodiments, the ratio of polyol to polycarboxylic acid in the hydrogel is 1 to 1.

In certain embodiments, the inventive polymer is an elastomer. Elastomers include tough elastomers and hydrated elastomers.

In certain embodiments, the inventive polymer is a tough elastomer (i.e., an elastomer which is not a hydrogel). In certain embodiments, the tough elastomer absorbs between about 0 to 9.5% water. In certain embodiments, the tough elastomer has an in-vivo half life of between about 1 week to 2 years. In certain embodiments, the tough elastomer has an in-vivo half life of at least about 1 week, 2 weeks, 3 weeks, 4 weeks, 2 months, 3 months, 4 months, months, 6 months, 7 months, 8 months, 9 months, 10 months, 11 months, 1 year, 1.5 years, or 2 years. In certain embodiments, the tough elastomer does not sustain permanent structural deformation upon stretching the polymer between about 1 to 2, 1 to 6, 1 to 8, 1 to 10, 1 to 20, 1 to 30, 1 to 40, 1 to 50, 1 to 60, 1 to 70, 1 to 80, 1 to 90, 1 to 100, 1 to 150, 1 to 200, 1 to 250, or 1 to 300% of its original length. In certain embodiments, the tough elastomer has a Young's moduli of at least about 0.5 to about 12 MPa. In certain embodiments, the tough elastomer has a Young's moduli of at least about 0.5 to about 6 MPa. In certain embodiments, the hydrated elastomer has a Young's moduli of about 12 MPa.

In certain embodiments, the tough elastomer maintains a three-dimensional shape. In certain embodiments, the ratio of polyol to polycarboxylic acid in the tough elastomer is 1 to 2.

In certain embodiments, the polymer is a hydrated elastomer (i.e., having the properties of both a hydrogel and an elastomer). In certain embodiments, the hydrated elastomer has an in-vivo half life of between about 1 week to about 2 years. In certain embodiments, the hydrated elastomer has an in-vivo half life of at least about 1 week, 2 weeks, 3 weeks, 4 weeks, 2 months, 3 months, 4 months, 5 months, 6 months, 7 months, 8 months, 9 months, 10 months, 11 months, 1 year, 1.5 years, or 2 years. In certain embodiments, the hydrated elastomer absorbs between about 10 to 100%, 10 to 90 wt %, 10 to 80 wt %, 10 to 70 wt %, 10 to 60 wt %, 10 to 50 wt %, 10 to 40 wt %, 10 to 30 wt %, 10 to 20 wt %, or 10 to 15 wt % of water. In certain embodiments, the hydrated elastomer does not sustain permanent structural deformation upon stretching the polymer between about 1 to 2, 1 to 6, 1 to 8, 1 to 10, 1 to 20, 1 to 30, 1 to 40, 1 to 50, 1 to 60, 1 to 70, 1 to 80, 1 to 90, 1 to 100, 1 to 150, 1 to 200, 1 to 250, or 1 to 300% of its original length. In certain embodiments, the hydrated elastomer has a Young's moduli of at least about 0.5 to about 12 MPa. In certain embodiments, the hydrated elastomer has a Young's moduli of at least about 0.5 to about 6 MPa. In certain embodiments, the hydrated elastomer has a Young's moduli of about 12 MPa.

In certain embodiments, an inventive elastomeric polymer is obtained by reacting a water soluble polyol with a water insoluble polycarboxylic acid. In certain embodiments, an inventive elastomeric polymer is obtained by reacting a water insoluble polyol with a water soluble polycarboxylic acid. In certain embodiments, an inventive elastomeric polymer is obtained by reacting a water insoluble polyol with a water insoluble polycarboxylic acid.

In certain embodiments, an inventive hydrogel polymer is obtained by reacting a water soluble polyol with a water soluble polycarboxylic acid.

In certain embodiments, an inventive hydrogel polymer is obtained by first reacting a water soluble polyol with a water soluble polycarboxylic acid, and then cross-linking the polymer in an aqueous environment.

In another aspect of the present invention, the inventive polymer further comprises, or is further modified with, a biologically active agent. In certain embodiments, the inventive polymer comprises at least one biologically active agent. In certain embodiments, the inventive polymer comprises at least two biologically active agents.

As used herein, a "biologically active agent" or "active agent," refers to therapeutic cells, organic molecules (e.g., drug compounds), peptides (e.g., dipeptides, polypeptides, proteins), antibodies, modified antibodies, receptors, aptamers, drug/peptide modified amino acids, enzymes, carbohydrates (e.g., monosaccharides, oligosaccharides, polysaccharides), nucleoproteins, mucoproteins, lipoproteins, glycoproteins, steroids, nucleic acids, DNAs, RNAs, nucleotides, nucleosides, polynucleotides, antisense oligonucleotides, lipids, hormones, and vitamins, metals, transition metals, or a combination thereof.

In certain embodiments, the biologically active agent is covalently conjugated to the polymer. In certain embodiments, the biologically active agent is covalently conjugated to the inventive polymer via an ester or amide linkage.

In certain embodiments, the biologically active agent is non-covalently conjugated to the polymer. In certain embodiments, the biologically active agent is entrapped (e.g., encapsulated) by the inventive polymer.

In certain embodiments, the biologically active agent is a "prodrug" when conjugated to the inventive polymer, and is administered to a subject in an inactive (or significantly less active) form. Once administered, the conjugated prodrug is metabolised in vivo, for example, by deacylation, dephosphorylation, hydrolysis, or epimerization, to a more active form.

However, in certain embodiments, the biologically active agent is as active, or partially active, when conjugated to the polymer (or when entrapped by the polymer) as compared to the free biologically active agent (i.e., not conjugated or entrapped).

In certain embodiments, the biologically active agent is a cell. Exemplary cells include immune system cells (e.g., mast cell, lymphocyte, plasma cell, macrophage, dendritic cell, neutrophils, eosinophils), connective tissue cells (e.g., blood cells, erythrocytes, leucocytes, megakaryocytes, fibroblasts, osteoclasts), stem cells (e.g., embryonic stem cells, adult stem cells), bone cells, glial cells, pancreatic cells, kidney cells, nerve cells, skin cells, liver cells, muscle cells, adipocytes, Schwann cells, Langerhans cells, as well as (micro)-tissues such as the Islets of Langerhans.

In certain embodiments, the biologically active agent is a small organic molecule. In certain embodiments, a small organic molecule is non-peptidic. In certain embodiments, a small organic molecule is non-oligomeric. In certain embodiments, a small organic molecule is a natural product or a natural product-like compound having a partial structure (e.g., a substructure) based on the full structure of a natural product. Exemplary natural products include steroids, penicillins, prostaglandins, venoms, toxins, morphine, paclitaxel (Taxol), morphine, cocaine, digitalis, quinine, tubocurarine, nicotine, muscarine, artemisinin, cephalosporins, tetracyclines, aminoglycosides, rifamycins, chloramphenicol, asperlicin, lovastatin, cyclosporin, curacin A, eleutherobin, discodermolide, bryostatins, dolostatins, cephalostatins, antibiotic peptides, epibatidine, α-bungarotoxin, tetrodotoxin, teprotide, and neurotoxins from *Clostridium botulinum*. In certain embodiments, a small organic molecule is a drug approved by the Food and Drugs Administration as provided in the Code of Federal Regulations (CFR).

In certain embodiments, the biologically active agent is a peptide. According to the present invention, a "peptide" or "protein" comprises a string of at least two amino acids linked together by peptide bonds. The terms "protein" and "peptide" may be used interchangeably. Peptide may refer to an individual peptide or a collection of peptides. Peptides may contain natural amino acids and/or non-natural amino acids (i.e., compounds that do not occur in nature but that can be incorporated into a polypeptide chain) and/or amino acid analogs, as are known in the art. Exemplary peptides include GCGGGRGDSPG (RGD), GCGGGVPHSRNSG (PHSRN), GCGGGYIGSRG (YIGSR), growth factors, and the like. One or more of the amino acids in a peptide may be modified, for example, by the addition of a chemical entity such as a carbohydrate group, a phosphate group, a farnesyl group, an isofarnesyl group, a fatty acid group, a linker for conjugation, functionalization, by the addition of a biologically active agent, or by other structural modifications. In certain embodiments, structural modifications of a peptide lead to a more stable peptide (e.g., greater half-life in vivo). Other structural modifications may include cyclization of the peptide, incorporation of D-amino acids, etc. None of the modifications should substantially interfere with the desired biological activity of the peptide.

In certain embodiments, the biologically active agent is a polynucleotide (e.g., a polymer of nucleotides). A polynucleotide comprises at least three nucleotides. The polymer may include natural nucleosides (i.e., adenosine, thymidine, guanosine, cytidine, uridine, deoxyadenosine, deoxythymidine, deoxyguanosine, and deoxycytidine), nucleoside analogs (e.g., 2-aminoadenosine, 2-thiothymidine, inosine, pyrrolopyrimidine, 3-methyl adenosine, C5-propynylcytidine, C5-propynyluridine, C5-bromouridine, C5-fluorouridine, C5-iodouridine, C5-methylcytidine, 7-deazadenosine, 7-deazaguanosine, 8-oxoadenosine, 8-oxoguanosine, O(6)-methylguanine, and 2-thiocytidine), chemically modified bases, biologically modified bases (e.g., methylated bases), intercalated bases, modified sugars (e.g., 2'-fluororibose, ribose, 2'-deoxyribose, arabinose, and hexose), or modified phosphate groups (e.g., phosphorothioates and 5'-N-phosphoramidite linkages).

In certain embodiments, the biologically active agent is modified with a linker group in order to facilitate attachment to an inventive polymer. In certain embodiments, the biologically active agent is modified with a nucleophilic or electrophilic group in order to facilitate attachment to an inventive polymer. For example, in certain embodiments, the biologically active agent is modified with an amino acid (or a peptide containing an amino acid modified with a biologically active agent) which bears a nucleophilic thiol, nucleophilic hydroxyl, or nucleophilic —NH— moiety (e.g., the amino acids cysteine, tyrosine, histidine, tryptophan, serine, threonine and lysine as depicted in FIG. 32; wherein $R^{AA}$ is a suitable carboxylic acid protecting group, as defined herein, or is a different, yet suitable group, such as an amino acid or peptide chain). The nucleophilic moiety of the amino acid (modified with a biologically active agent) may facilitate covalent attachment via its addition to an electrophilic group present on the inventive polymer, or displacement of a suitable leaving group. Electrophilic groups present on the inventive polymer include, for example, oxo group (═O), thiooxo group (═S), acrylate groups a double bond, a triple bond, a carboxylic acid moiety (—$CO_2H$), a —CHO group, an ester group, an activated carboxylic acid moiety (as defined herein), and the like. Suitable leaving groups present on the inventive polymer include, for example, a halogen, a hydroxyl moiety, an activated hydroxyl moiety (as defined herein), and the like. Alternatively, an electrophilic moiety of the amino acid, such as the carboxylic acid moiety of the amino acid, may facilitate covalent attachment via reaction with a nucleophilic group present on the inventive polymer.

Pharmaceutical Compositions and Formulations

The present invention provides a pharmaceutical composition comprising an inventive polymer. In certain embodiments, the pharmaceutical composition further comprises a biologically active agent, as described herein. In certain embodiments, the pharmaceutical composition includes any number of additional biologically active agents, for example, a second, a third, a fourth, or a fifth, biologically active agent.

In certain embodiments, the pharmaceutical composition further comprises a pharmaceutically acceptable carrier, adjuvant, or vehicle, which, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Remington's Pharmaceutical Sciences, Sixteenth Edition, E. W. Martin (Mack Publishing Co., Easton, Pa., 1980) discloses various carriers used in formulating pharmaceutically acceptable compositions and known techniques for the preparation thereof. Except insofar as any conventional carrier medium is incompatible with the polymer of the present invention, such as by producing any undesirable biological effect or otherwise interacting in a deleterious manner with any other component(s) of the pharmaceutically acceptable composition, its use is contemplated to be within the scope of this invention.

Some examples of materials which can serve as pharmaceutically acceptable carriers include, but are not limited to, ion exchangers, alumina, aluminum stearate, lecithin, triethyl citrate, serum proteins, such as human serum albumin, buffer substances such as phosphates, glycine, sorbic acid, or potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, polyacrylates, waxes, polyethylene-polyoxypropylene-block polymers, wool fat, sugars such as lactose, glucose and sucrose; starches such as corn starch and potato starch; cellulose and its derivatives such as sodium carboxymethyl cellulose, microcrystalline cellulose, ethyl cellulose and cellulose acetate; powdered tragacanth; malt; gelatin; hypromellose (vegetarian version of gelatin); talc; excipients such as cocoa butter and suppository waxes; oils such as peanut oil, cottonseed oil; safflower oil; sesame oil; olive oil; corn oil and soybean oil; glycols; such a propylene glycol or polyethylene glycol; esters such as ethyl oleate and ethyl laurate; agar; buffering agents such as sodium hydroxide, magnesium hydroxide and aluminum hydroxide; alginic acid; pyrogen-free water; isotonic saline; Ringer's solution; ethyl alcohol, and phosphate buffer solutions; inorganic or organic salts such as sodium chloride, sodium hydrogen phosphate, sodium nitrate and sodium acetate, or acids and salts such as tartaric, citric or succinic acid; sugars, e.g. mannitol, glucose, fructose, lactose and dextran compounds; as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition.

Uses of the Inventive Polymers

The inventive polymers may be useful in drug delivery (e.g., delivery of antibiotics, drugs, bioactive agents); as an injectable drug delivery system for mechanically taxing environments (such as within joints) where the material may release a drug in a controlled manner without being compromised by a dynamic or static external environment; as chewing gum for delivering biologically active materials and/or nutrients and/or vitamins); as an I.V. infusion material for patients requiring an osmotic active agent to reduce brain oedema, to reduce swelling of any other kind of tissue or organ, and/or for patients requiring colloid volume expansion; as a hydrogel used for cell-encapsulation; as long term circulating particles for applications including targeted drug delivery, blood substitutes; patches for diabetic ulcers; intra-abdominal implant to prevent adhesions; in vivo and in vitro sensors; as edible films (e.g., for taking a medication); fiber optics (e.g., provide a porous network for delivering fluids in vivo); intraocular devices; in formation of nerve conduits; in mesh repair of herniae (e.g., abdominal herniae); in ligament repair; as osteo-synthesis material (e.g., screws); in intervertebral disc repair; in soft tissue repair; in bone tissue repair; in heart valve replacement; in osmotically active infusions; use of biodegradable particles, tubes, spheres, strands, threads, coiled strands, films, sheets, fibers, meshes, and the like; as catheters, intravenous (IV) lines, feeding tubes, O-rings, septa, and the like; in sutures (tunable for fast or slow degradation); in surgical glue and adhesives; in post-trauma surgery adhesion prevention; as components of contact lenses; for medical implant coatings (e.g., stents); for injectables; for vascular grafts; microfabrication applications (capillary networks, diagnostics) for tissue engineering (i.e., bladder, bone, brain, nerve, skin, cardiac tissue, ligament, cartilage, tendon, genital, muscle, artery, veins, kidney, pancreas, liver, intestine, stomach, and other tissues); and as an injectable (e.g., to aid in cosmetic and/or surgical procedures). In the industrial field, the inventive biodegradable polymers may be useful in the fields of agriculture and landscaping (e.g., seeding strips and tapes); biodegradable packaging (e.g., food containers; gift wrappings; foams; filters; disposable bags); biodegradable outdoor items (e.g., as a core material of balls such as golf balls, baseballs, and bouncing balls; as a material for inflatable balloons; as a ski or board wax; as a material for fishing lures); as a component in cosmetics (e.g., as an alternative hair product to wax products; as an injectable for cosmetic surgery); as a material in absorbent garments (e.g., disposable diapers; panty liners; incontinence protectors); edible films (e.g., protection of freshness of food product and be completely biodegradable within the digestive tract; flavor and/or aroma barriers); and as a material in food formulations (e.g., diet formulations). The present invention contemplates, but is not limited to, all such useful applications for polymers of the presently claimed invention.

Methods of Using an Inventive Polymer

The present invention provides a method of using an inventive polymer or a polymer composition, as described above and herein, comprising administering to a subject suffering from a disease, condition, or disorder an inventive polymer or polymer composition.

In certain embodiments, a therapeutically effective amount of the inventive polymer or composition is administered. As used herein, a "therapeutically effective amount" of an inventive polymer or composition is an amount that can achieve a desired therapeutic and/or prophylactic effect. A "therapeutically effective amount" is at least a minimal amount of an inventive polymer or composition which is sufficient for preventing, ameliorating, reducing, delaying, or diminishing severity of a disease, disorder, or condition from which a subject is suffering.

Exemplary diseases, conditions, or disorders which may be treatable by the polymers or pharmaceutical compositions of the present invention include: anxiety, convulsions or epilepsy, depression, pain, bacterial infections, viral infections, fungal infections, hormonal imbalances, chemical imbalances, allergic disorders or conditions, external or internal lesions, diseased tissue, bone or muscle injuries, bone breakage or fracture, joint conditions, arthritis, sepsis, necrosis, autoimmune diseases, blood disorders, bone disorders, cancers, circulation diseases, dental conditions, digestion and nutrition disorders, gastrointestinal diseases, genetic disorders, heart diseases, hormonal disorders, infectious diseases, inflammation, kidney diseases, liver diseases, mental health disorders, metabolic diseases, neurological disorders, skin conditions, and the like.

In certain embodiments, the inventive polymer, or pharmaceutical composition comprising the inventive polymer, is administered to the subject by any known means, e.g., transdermally, orally, per anum, parenterally, intravenously (IV), intra-arterially, subcutaneously, intracutaneously, intradural, subdural, epidural, by surgically implantation, absorption, ingestion, injection, or inhalation of the inventive polymer or pharmaceutical composition.

In certain embodiments, the inventive polymer is a component of a biomedical device or implant. In certain embodiments, the inventive polymer is a polymer film or coating on an implant. In certain embodiments, the inventive polymer is an implant. In certain embodiments, the inventive polymer implant is a polymer matrix.

In certain embodiments, the inventive polymer is injected or implanted into a subject. In certain embodiments, the pre-polymer to the inventive polymer (i.e., prior to polymerization) is injected or implanted into a subject. In certain embodiments, the pre-polymer is injected or surgically implanted, and polymerized in vivo.

In one embodiment, the inventive polymer is surgically implanted or injected into a subject on or near diseased or damaged tissue. In certain embodiments, the inventive polymer implant aids in the in-growth of surrounding healthy tissue to the diseased area.

In certain embodiments, the inventive polymer further includes a biologically active agent. Biologically active agents include any substance used as a medicine for treatment, prevention, delay, reduction or amelioration of a disease, condition, or disorder, and refers to a substance that is useful for therapy, including prophylactic and therapeutic treatment. A biologically active agent also includes a compound that increases the effect or effectiveness of another compound, for example, by enhancing potency or reducing adverse effects of the other compound.

In certain embodiments, the biologically active agent is cleaved from the inventive polymer upon enzymatic hydrolysis. In certain embodiments, the biologically active agent, upon release or cleavage, participates in treating a condition, disease, or disorder from which a subject is suffering.

Methods of Making an Inventive Polymer

The present invention provides a method of making an inventive polymer comprising the steps of:

(i) providing a polyol;

(ii) providing a polycarboxylic acid, or derivative thereof; and (iii) reacting the polyol with the polycarboxylic acid to provide the inventive polymer.

In certain embodiments, the inventive polymer, so provided, is a water insoluble polymer. In certain embodiments, the inventive polymer, so provided, is a water soluble polymer. The polyol and polycarboxylic acid of step (i) and (ii) may be any polyol and polycarboxylic acid so described above and herein; thus the inventive polymer formed from the above method may be any combination or ratio of polyol to polycarboxylic acid, as described above and herein.

One of ordinary skill in the art will appreciate that a wide variety of reaction conditions may be employed to promote the above transformation, therefore, a wide variety of reaction conditions are envisioned; see generally, *March's Advanced Organic Chemistry: Reactions, Mechanisms, and Structure*, M. B. Smith and J. March, $5^{th}$ Edition, John Wiley & Sons, 2001, and *Comprehensive Organic Transformations*, R. C. Larock, $2^{nd}$ Edition, John Wiley & Sons, 1999, the entirety of both of which are incorporated herein by reference.

In certain embodiments, the reaction of step (iii) is a condensation reaction (e.g., reaction between a carboxylic acid or derivative thereof and an alcohol, with the extrusion of water, an alcohol by-product, or a suitable leaving group). In certain embodiments, the condensation reaction of step (iii) employs Schotten-Baumann reaction conditions. The Schotten-Baumann reaction is a well-known reaction to those skilled in the art; see generally Sonntag et al., *Chem. Rev.* (1953) 52:237-4161, and Challis and Butler, *Chem. Amino Group* (1968) 277-347, the entirety of both of which are incorporated herein by reference.

In certain embodiments, the reaction of step (iii) further comprises the application of heat. In certain embodiments, the reaction of step (iii) comprises heating the polyol and the polycarboxylic acid to a temperature of at least 50° C. In certain embodiments, the reaction is heated to a temperature of at least 60° C., 70° C., 80° C., 90° C., 100° C., 110° C., 120° C., 125° C., 130° C., 135° C., 140° C., 145° C., 150° C., 155° C., 160° C., 165° C., or 170° C.

In certain embodiments, the reaction of step (iii) further comprises conducting the reaction under reduced pressure (i.e., in a vacuum, in vacuo).

In certain embodiments, the condensation reaction of step (iii) further includes an activating agent. Exemplary activating agents include, but are not limited to, thionyl chloride, thionyl bromide, oxalyl chloride, Bronstead acids, and Lewis acids. Exemplary Bronstead acids include, but are not limited to, hydrogen chloride, hydrogen bromide, acetic acid, formic acid, and the like. Exemplary Lewis acids include, but are not limited to, aluminum chloride, iron chloride, boron trifluoride, boron tribromide, and boron trichloride.

In certain embodiments, the reaction of step (iii) further includes a suitable solvent. However, in certain embodiments, the reaction of step (iii) does not include a solvent.

A "suitable solvent" is a solvent that, in combination with the combined reacting partners and reagents, facilitates the progress of the reaction there-between. A suitable solvent may solubilize one or more of the reaction components, or, alternatively, the suitable solvent may facilitate the suspension of one or more of the reaction components; see, generally, March (2001). Suitable solvents include ethers, halogenated hydrocarbons, aromatic solvents, polar aprotic solvents, polar protic solvents, or mixtures thereof. In certain embodiments, the solvent comprises water, diethyl ether, dioxane, tetrahydrofuran (THF), dichloromethane (DCM), dichloroethane (DCE), chloroform, toluene, benzene, dimethylformamide (DMF), dimethylacetamide (DMA), dimethylsulfoxide (DMSO), N-methylpyrrolidinone (NMP), or mixtures thereof.

In certain embodiments, the polyol is a fully unprotected polyol (i.e., comprising free, unprotected, —OH groups). In certain embodiments, the polycarboxylic acid is a fully unprotected polycarboxylic acid (i.e., comprising free, unprotected, —COOH groups). In certain embodiments, both the polyol and the polycarboxylic acid are fully unprotected.

In certain embodiments, the polycarboxylic acid is an activated or a protected polycarboxylic acid. Activated carboxylic acids are well known to one skilled in the art. Exemplary activated carboxylic acids include, but are not limited to, carboxylic acids activated as anhydrides or as acyl halides (e.g., acyl chloride, acyl bromide). Exemplary protected carboxylic acids, such as esters, are also well known to one skilled in the art; see generally, Greene (1999). Suitable carboxylic acid protecting groups include, but are not limited to, silyl-, alkyl-, alkenyl-, aryl-, and arylalkyl-protected carboxylic acids. Examples of suitable silyl groups include trimethylsilyl, triethylsilyl, t-butyldimethylsilyl, t-butyldiphenylsilyl, triisopropylsilyl, and the like. Examples of suitable alkyl groups include methyl, ethyl, n-propyl, isopropyl, allyl, n-butyl, sec-butyl, or t-butyl group, benzyl, p-methoxybenzyl, 3,4-dimethoxybenzyl, trityl, t-butyl, tetrahydropyran-2-yl. Examples of suitable alkenyl groups include allyl. Examples of suitable aryl groups include optionally substituted phenyl, biphenyl, or naphthyl. Examples of suitable arylalkyl groups include optionally substituted benzyl (e.g., p-methoxybenzyl (MPM), 3,4-dimethoxybenzyl, O-nitrobenzyl, p-nitrobenzyl, p-halobenzyl, 2,6-dichlorobenzyl, p-cyanobenzyl), and 2- and 4-picolyl.

In certain embodiments, for example, when the polycarboxylic acid is a protected polycarboxylic acid, the reaction of step (iii) may further comprise a base. Exemplary bases include potassium carbonate, potassium hydroxide, sodium hydroxide, tetrabutylammonium hydroxide, benzyltrimethylammonium hydroxide, triethylbenzylammonium hydroxide, 1,1,3,3-tetramethylguanidine, 1,8-diazabicyclo[5.4.0]undec-7-ene (DBU), N-methylmorpholine, diisopropylethylamine (DIPEA), tetramethylethylenediamine, pyridine, N,N-dimethylamino pyridine (DMAP), or triethylamine.

In certain embodiments, the product of step (iii) is a hydrogel. In certain embodiments, the product of step (iii) is a tough elastomer. In certain embodiments, the product of step (iii) is a hydrated elastomer. In certain embodiments, the product of step (iii) is a stiff, hard polymer.

In certain embodiments, the product of step (iii) is water-soluble. In certain embodiments, when the product of step (iii) is water-soluble, the polyol of step (i) is also water-soluble. In certain embodiments, when the product of step (iii) is water-soluble, the polycarboxylic acid of step (ii) is also water soluble. In certain embodiments, when product of step (iii) is water-soluble, both the polyol of step (i) and the polycarboxylic acid are water-soluble. In certain embodiments, the water-soluble product of step (iii) is also a hydrogel or a hydrated elastomer.

In certain embodiments, the product of step (iii) is not water-soluble. In certain embodiments, when the product of step (iii) is water-insoluble, the polyol of step (i) is also embodiments, the polyol is xylitol, mannitol, sorbitol, or maltitol. In certain embodiments, the polyol is xylitol. In certain embodiments, the sugar alcohol glycerol is specifically excluded.

Similarly, in certain aspects of the present invention, the polycarboxylic acid monomer used in the formation of the inventive polymer is a compound found in nature, or derived from nature. In certain embodiments, the polycarboxylic acid is endogenous to the human metabolic system. In certain embodiments, the polycarboxylic acid is non-toxic. In certain embodiments, the polycarboxylic acid is an aliphatic polycarboxylic acid (i.e., does not contain arylene or heteroarylene groups). In certain embodiments, the polycarboxylic acid is optically enriched. In certain embodiments, the polycarboxylic acid has a center of symmetry.

In certain embodiments, the polycarboxylic acid used in the formation of the inventive polymer is a dicarboxylic acid. In certain embodiments, the polycarboxylic acid is a tricarboxylic acid.

In certain embodiments, the polycarboxylic acid used in the formation of the inventive polymer is an amino acid. Exemplary amino acids include aspartic acid or glutamic acid.

In certain embodiments, the polycarboxylic acid used in the formation of the inventive polymer is a polypeptide. In certain embodiments, the polycarboxylic acid used in the formation of the inventive polymer is an oligopeptide. In certain embodiments, the polycarboxylic acid used in the formation of the inventive polymer is a protein.

In certain embodiments, the polycarboxylic acid used in the formation of the inventive polymer is a metabolite. In certain embodiments, the metabolite is a citric acid cycle (Kreb's cycle) metabolite. Exemplary metabolites include succinic acid, fumaric acid, $\alpha$-ketoglutaric acid, oxaloacetic acid, malic acid, oxalosuccinic acid, isocitric acid, cis-aconitic acid, and citric acid. In certain embodiments, the polycarboxylic acid is optionally substituted citric acid. However, in certain embodiments, citric acid is specifically excluded. Furthermore, in certain embodiments, the polymer formed from citric acid and the polyol glycerol is specifically excluded.

In certain embodiments, the polycarboxylic acid used in the formation of the inventive polymer comprises an optionally substituted aldaric acid. An aldaric acid (a "sugar acid") is an oxidized aldose sugar in which both the hydroxyl functional groups of the terminal carbon and the aldehyde function of the first carbon have been fully oxidized to carboxylic acid water-insoluble. In certain embodiments, when the product of step (iii) is water-insoluble, the polycarboxylic acid of step (ii) is also water-insoluble. In certain embodiments, when product of step (iii) is water-insoluble, both the polyol of step (i) and the polycarboxylic acid are water-insoluble. In certain embodiments, the water-insoluble product of step (iii) is also a tough elastomer or a hydrated elastomer.

Step (iv): Functionalization of the Polymer of Step (iii)

(I). Acrylation

The method of making an inventive polymer may further comprise the step of:

(iv) reacting the polymer of step (iii) with a acrylating compound.

Reaction of the polymer of step (iii) with an acrylating compound in step (iv) provides an acrylated polymer. One of ordinary skill in the art will appreciate that a wide variety of reaction conditions may be employed to promote acrylation of the polymer of step (iii) with an acrylating compound, therefore, a wide variety of reaction conditions are envisioned; see generally, *March's Advanced Organic Chemistry: Reactions*, Mechanisms, and Structure, M. B. Smith and J. March, 5$^{th}$ Edition, John Wiley & Sons, 2001, and *Comprehensive Organic Transformations*, R. C. Larock, 2$^{nd}$ Edition, John Wiley & Sons, 1999; the entirety of both of which are incorporated herein by reference.

Exemplary acrylating compounds include, but are not limited to, acrylic acid, acryloyl chloride, methacrylic acid, methacryloyl chloride, but-2-enoic acid, but-2-enoyl chloride, butyl acrylate, 2-ethylhexyl acrylate, methyl acrylate, ethyl acrylate, methyl methacrylate, methacrylic anhydride, allyl glycidyl ether, glycidyl acrylate, glycidyl methacrylate, trimethylol propane triacrylate (TMPTA), and the like.

Additional reagents and/or conditions may be employed to facilitate the acrylation reaction of step (iv) between acrylating compound and the polymer, such as, for example, the employment of a suitable base, or the application of heat.

In certain embodiments, the acrylation reaction of step (iv) further comprises the application of heat. In certain embodiments, the reaction of step (iv) comprises heating the acrylating compound and the polymer to a temperature of at least 30° C. In certain embodiments, the reaction is heated to a temperature of at least 40° C., 50° C., 60° C., 70° C., 80° C., 90° C., or 100° C.

However, in certain embodiments, the acrylation reaction of step (iv) further comprises cooling. In certain embodiments, the reaction of step (iv) comprises cooling the acrylating compound and the polymer to a temperature of at least 10° C. In certain embodiments, the reaction is cooled to a temperature of at least 5° C. or 0° C. In certain embodiments, the reaction is cooled to a temperature of at least 5° C., and then gradually warmed to room temperature.

In certain embodiments, the acrylation reaction of step (iv) further comprises a suitable base. Exemplary bases include potassium carbonate, potassium hydroxide, sodium hydroxide, tetrabutylammonium hydroxide, benzyltrimethylammonium hydroxide, triethylbenzylammonium hydroxide, 1,1,3,3-tetramethylguanidine, 1,8-diazabicyclo[5.4.0]undec-7-ene (DBU), N-methylmorpholine, diisopropylethylamine (DIPEA), tetramethylethylenediamine, pyridine, N,N-dimethylamino pyridine (DMAP), or triethylamine.

In certain embodiments, the reaction of step (iv) further comprises a suitable solvent. Suitable solvents include ethers, halogenated hydrocarbons, aromatic solvents, polar aprotic solvents, or mixtures thereof. In certain embodiments, the solvent comprises diethyl ether, dioxane, tetrahydrofuran (THF), dichloromethane (DCM), dichloroethane (DCE), chloroform, toluene, benzene, dimethylformamide (DMF), dimethylacetamide (DMA), dimethylsulfoxide (DMSO), N-methylpyrrolidinone (NMP), or mixtures thereof.

In certain embodiments, the polymer product of the acrylation reaction of step (iv) is water-soluble. In certain embodiments, the polymer product of either the acrylation reaction step is not water-soluble. In certain embodiments, the polymer product of the acrylation reaction of step (iv) is a hydrogel. In certain embodiments, the polymer product of the acrylation reaction of step (iv) is a tough elastomer. In certain embodiments, the polymer product of the acrylation reaction of step (iv) is a hydrated elastomer.

In certain embodiments, the polymer product of the acrylation reaction of step (iv) is isolated by extraction with an organic solvent. In certain embodiments, the polymer product of the acrylation reaction of step (iv) is precipitated from the reaction. In certain embodiments, the polymer product of the acrylation reaction of step (iv) is isolated via filtration. In certain embodiments, the polymer product of the acrylation reaction of step (iv) is further dialysed against water. In certain embodiments, the polymer product of the acrylation reaction of step (iv) is further dialysed against water and then lyophilized.

(II). Dihydrazide Chemistry

Alternatively, in certain embodiments, the reaction of step (iv) may comprise the step of:

(iv) reacting the polymer of step (iii) with a dihydrazide compound.

In certain embodiments, the polymer of step (iii) which has a carboxylic acid, ester, or aldehydic functional group is treated with a dihydrazide compound to provide a hydrazide modified polymer. In certain embodiments, the polymer of step (iii) is first modified by activating the carboxylic acid, ester, or aldehydic functional group present on the polymer, and then treating this polymer having an activated functional group with a dihydrazide compound to provide a hydrazide modified polymer.

For example, in certain embodiments, the polymer of step (iii) having carboxylic acid groups (—$CO_2H$) is further modified by reacting the —$CO_2H$ groups of the polymer with a dihydrazide compound to provide a hydrazide modified polymer. In certain embodiments, the carboxylic acid groups are activated. In certain embodiments, the carboxylic acid groups are activated with an activating reagent prior to treatment with the dihydrazide compound.

Exemplary activating reagents include, but are not limited to, thionyl chloride, thionyl bromide, oxalyl chloride, which generate the an acyl halide as the activated carboxylic acid. Other activating reagents are commonly referred to as "coupling reagents" (for example, benzotriazol-1-yloxy-tris(dimethylamino)-phosphonium hexafluorophosphate (BOP), benzotriazole-1-yl-oxy-tris-pyrrolidino-phosphonium hexafluorophosphate (PyBOP), bromo-tris-pyrrolidino phosphonium hexafluorophosphate (PyBroP), 1-ethyl-3-(3-dimethylaminopropyl) carbodiimide (EDC), N,N'-carbonyldiimidazole (CDI), 3-(diethoxyphosphoryloxy)-1,2,3-benzotriazin-4(3H)-one (DEPBT), 1-hydroxy-7-azabenzotriazole (HOAt), 1-hydroxy-7-benzotriazole (HOBt), 2-(7-aza-1H-benzotriazole-1-yl)-1,1,3,3-tetramethyluronium hexafluorophosphate (HATU), 2-(6-chloro-1H-benzotriazole-1-yl)-1,1,3,3-tetramethylaminium hexafluorophosphate (HCTU), 2-(1H-benzotriazole-1-yl)-1,1,3,3-tetramethyluronium hexafluorophosphate (HBTU), O-(7-azabenzotriazole-1-yl)-N,N,N',N'-tetramethyluronium tetrafluoroborate (TATU), 2-(1H-benzotriazole-1-yl)-1,1,3,3-tetramethyluronium tetrafluoroborate (TBTU), N,N,N',N'-tetramethyl-O-(3,4-dihydro-4-oxo-1,2,3-benzotriazin-3-yl) uranium tetrafluoroborate (TDBTU), and O—(N- succinimidyl)-1,1,3,3-tetramethyl uranium tetrafluoroborate (TSTU)). Other exemplary activated carboxylic acids include, but are not limited to, esters, anhydrides, and —CO$_2$— (sulfonyl) groups. Sulfonyl groups include trifluoromethylsulfonyl (-Tf), tolylsulfonyl (-Ts), methanesulfonyl (-Ms), (4-nitrophenylsulfonyl) (-Nos), and (2-nitrophenylsulfonyl) (-Ns).

In certain embodiments, the polymer of step (iii) having an aldehydic group (—CHO) is further modified by reacting the —CHO group of the polymer with a dihydrazide compound to provide a hydrazide modified polymer.

One of ordinary skill in the art will appreciate that a wide variety of reaction conditions may be employed to promote the reaction between a carboxylic acid and a dihydrazide compound, or an aldehyde and a dihydrazide compound, and therefore, a wide variety of reaction conditions are envisioned; see generally, Bulpitt and Aeschlimann, *J. Biomed. Mater. Re.* (1999) 47:152-169; *March's Advanced Organic Chemistry: Reactions*, Mechanisms, and Structure, M. B. Smith and J. March, 5$^{th}$ Edition, John Wiley & Sons, 2001, and *Comprehensive Organic Transformations*, R. C. Larock, 2$^{nd}$ Edition, John Wiley & Sons, 1999; the entirety of which are incorporated herein by reference.

Exemplary dihydrazide compounds include, but are not limited to, adipic dihydrazide, succinic dihydrazide, carbonic dihydrazide, oxalic dihydrazide, glutaric dihydrazide, pimelic dihydrazide, malonic dihydrazide, maleic dihydrazide, and isophthalic dihydrazide.

Additional reagents and/or conditions may be employed to facilitate the reaction between the dihydrazide compound and the —CHO or —CO$_2$H functionalized polymer, such as, for example, the employment of a suitable base, a suitable activating reagent, or the application of heat.

In certain embodiments, the reaction between the dihydrazide compound and the —CHO or —CO$_2$H functionalized polymer further comprises the application of heat. In certain embodiments, the reaction comprises heating the dihydrazide compound and the polymer to a temperature of at least 30° C. In certain embodiments, the reaction is heated to a temperature of at least 40° C., 50° C., 60° C., 70° C., 80° C., 90° C., or 100° C.

However, in certain embodiments, the reaction between the dihydrazide compound and the —CHO or —CO$_2$H functionalized polymer further comprises cooling. In certain embodiments, the reaction comprises cooling the dihydrazide compound and the polymer to a temperature of at least 10° C. In certain embodiments, the reaction is cooled to a temperature of at least 5° C. or 0° C. In certain embodiments, the reaction is cooled to a temperature of at least 5° C., and then gradually warmed to room temperature.

In certain embodiments, the reaction between the dihydrazide compound and the —CHO or —CO$_2$H functionalized polymer further comprises a suitable base. Exemplary bases include potassium carbonate, potassium hydroxide, sodium hydroxide, lithium hydroxide, potassium hydroxide, tetrabutylammonium hydroxide, benzyltrimethylammonium hydroxide, triethylbenzylammonium hydroxide, 1,1,3,3-tetramethylguanidine, 1,8-diazabicyclo[5.4.0]undec-7-ene (DBU), N-methylmorpholine, diisopropylethylamine (DIPEA), tetramethylethylenediamine, pyridine, N,N-dimethylamino pyridine (DMAP), or triethylamine.

In certain embodiments, the reaction between the dihydrazide compound and the —CHO or —CO$_2$H functionalized polymer further comprises a suitable solvent. Suitable solvents include water, ethers, halogenated hydrocarbons, aromatic solvents, polar aprotic solvents, polar protic solvents, or mixtures thereof. In certain embodiments, the solvent comprises water, saline, diethyl ether, dioxane, tetrahydrofuran (THF), dichloromethane (DCM), dichloroethane (DCE), chloroform, toluene, benzene, dimethylformamide (DMF), dimethylacetamide (DMA), dimethylsulfoxide (DMSO), N-methylpyrrolidinone (NMP), or mixtures thereof.

In certain embodiments, the hydrazide modified polymer of step (iv) is water-soluble. In certain embodiments, the hydrazide modified polymer of step (iv) is not water-soluble. In certain embodiments, the hydrazide modified polymer of step (iv) is a hydrogel. In certain embodiments, the hydrazide modified polymer of step (iv) is a tough elastomer. In certain embodiments, the hydrazide modified polymer of step (iv) is a hydrated elastomer.

In certain embodiments, the hydrazide modified polymer of step (iv) is isolated by extraction with an organic solvent. In certain embodiments, the hydrazide modified polymer of step (iv) is precipitated from the reaction. In certain embodiments, the hydrazide modified polymer of step (iv) is isolated via filtration. In certain embodiments, the hydrazide modified polymer of step (iv) is further dialysed against water. In certain embodiments, the hydrazide modified polymer of step (iv) is further dialysed against water and then lyophilized.

(III) Oxidation

Alternatively, in certain embodiments, the reaction of step (iv) may comprise the step of:

(iv) oxidizing the polymer of step (iii).

Furthermore, in certain embodiments, the reaction of step (iv) may comprise the step of:

(iv) oxidizing the polymer of step (iii) to provide an oxidized product, and reacting the oxidized product with a dihydrazide compound to provide a hydrazide product.

In certain embodiments, the oxidation reaction of step (iv) may comprise oxidizing the polymer of step (iii) with a suitable oxidizing reagent. Suitable oxidation reagents include chromium oxidation reagents, lead oxidation reagents, iron oxidation reagents, copper oxidation reagents, mercury oxidation reagents, vanadium oxidation reagents, nickel oxidation reagents, ruthenium oxidation reagents, magnesium oxidation reagents, manganese oxidation reagents, osmium oxidation reagents, peroxides, periodate oxidation reagents, iodine oxidation reagents, chloride oxidation reagents, oxygen, O$_3$, or mixtures thereof. Exemplary oxidation reagents include, but are not limited to, Ca(OCl)$_2$, MnO$_2$, KMnO$_4$, BaMnO$_4$, Cu(MnO$_4$)$_2$, NaMnO$_4$, HgO, Pb(OAc)$_2$, NaOCl, NiO$_2$, RuO$_4$, K$_2$FeO$_4$, VO(acac)$_2$, OsO$_4$, KIO$_4$, NaIO$_4$, K$_2$RuO$_4$, PhIO, PhI(OAc)$_2$, K$_2$Cr$_2$O$_7$, Collins reagent (CrO$_3$-2pyridine), pyridinium dichromate (PDC), and pyridinium chlorochromate (PCC).

One of ordinary skill in the art will appreciate that a wide variety of reaction conditions may be employed to promote oxidation of the polymer of step (iv) with an oxidizing reagent, therefore, a wide variety of reaction conditions are envisioned; see generally, *March's Advanced Organic Chemistry: Reactions*, Mechanisms, and Structure, M. B. Smith and J. March, 5$^{th}$ Edition, John Wiley & Sons, 2001, and *Comprehensive Organic Transformations*, R. C. Larock, 2$^{nd}$ Edition, John Wiley & Sons, 1999; the entirety of both of which are incorporated herein by reference. For example, in certain embodiments, the oxidizing reagent is a reagent which oxidizes a hydroxyl group to an aldehyde. In certain embodiments, the oxidizing reagent is a reagent which cleaves a diol to provide an aldehydic moiety (—CHO).

Additional reagents and/or conditions may be employed to facilitate the oxidation reaction between an oxidizing reagent and the polymer of step (iii), such as, for example, the employment of a suitable base, or the application of heat.

In certain embodiments, the oxidation reaction of step (iv) further comprises the application of heat. In certain embodiments, the oxidation reaction of step (iv) comprises heating the oxidizing reagent and the polymer to a temperature of at least 30° C. In certain embodiments, the oxidation reaction is heated to a temperature of at least 40° C., 50° C., 60° C., 70° C., 80° C., 90° C., or 100° C.

However, in certain embodiments, the oxidation reaction of step (iv) further comprises cooling. In certain embodiments, the oxidation reaction of step (iv) comprises cooling the oxidizing reagent and the polymer to a temperature of at least 10° C. In certain embodiments, the oxidation reaction is cooled to a temperature of at least 5° C. or 0° C. In certain embodiments, the oxidation reaction is cooled to a temperature of at least 5° C., and then gradually warmed to room temperature.

In certain embodiments, the oxidation reaction of step (iv) further comprises a suitable base. Exemplary bases include potassium carbonate, potassium hydroxide, sodium hydroxide, lithium hydroxide, potassium hydroxide, tetrabutylammonium hydroxide, benzyltrimethylammonium hydroxide, triethylbenzylammonium hydroxide, 1,1,3,3-tetramethylguanidine, 1,8-diazabicyclo[5.4.0]undec-7-ene (DBU), N-methylmorpholine, diisopropylethylamine (DIPEA), tetramethylethylenediamine, pyridine, N,N-dimethylamino pyridine (DMAP), or triethylamine.

In certain embodiments, the oxidation of step (iv) further comprises a suitable solvent. Suitable solvents include ethers, halogenated hydrocarbons, aromatic solvents, polar aprotic solvents, polar protic solvents, or mixtures thereof. In certain embodiments, the solvent comprises water, saline, diethyl ether, dioxane, tetrahydrofuran (THF), dichloromethane (DCM), dichloroethane (DCE), chloroform, toluene, benzene, dimethylformamide (DMF), dimethylacetamide (DMA), dimethylsulfoxide (DMSO), N-methylpyrrolidinone (NMP), or mixtures thereof.

In certain embodiments, the polymer product of the oxidation reaction of step (iv), is water-soluble. In certain embodiments, the polymer product oxidation reaction of step (iv) is not water-soluble. In certain embodiments, the polymer product of the oxidation reaction of step (iv) is a hydrogel. In certain embodiments, the polymer product of the oxidation reaction of step (iv) is a tough elastomer. In certain embodiments, the polymer product of the oxidation reaction of step (iv) is a hydrated elastomer.

In certain embodiments, the polymer product of the oxidation reaction of step (iv) is isolated by extraction with an organic solvent. In certain embodiments, the polymer product of the oxidation reaction of step (iv) is precipitated from the reaction. In certain embodiments, the polymer product of the oxidation reaction of step (iv) is isolated via filtration. In certain embodiments, the polymer product of the oxidation reaction of step (iv) is further dialysed against water. In certain embodiments, the polymer product of the oxidation reaction of step (iv) is further dialysed against water and then lyophilized.

Step (v): Polymerization

The method of making an inventive polymer may further comprise the step of:

(v) polymerizing the product of step (iv).

In certain embodiments, the product of step (iv) is the acrylated product. In certain embodiments, the product of step (iv) is the hydrazide product. In certain embodiments, the product is of step (iv) is the oxidized product.

In certain embodiments, the polymerization reaction is via ring opening metathesis polymerization (ROMP), reversible addition-fragmentation chain transfer (RAFT) polymerization, reversible addition-fragmentation chain transfer (RAFT) polymerization, or radical polymerization.

In certain embodiments, the radical polymerization is photo-initiated (photopolymerization), light-induced, or heat-induced radical polymerization.

In certain embodiments, the polymerization reaction further requires prior addition of an initiator to the reaction of step (v). Exemplary initiators include, but are not limited to, photoinitiators (e.g., IRGACURE® photoinitiators), peroxides, N-oxides, tert-butyl peroxide, benzoyl peroxide, 2,2-dimethoxy-2-phenyl-acetophenone, acetophenone, azobisisobutyrylnitrile (AIBN), N,N,N',N'-tetramethylethylenediamine (TEMED), tetraethylenepentamine (TEPA), a Ziegler-Natta catalyst, an acid, a base, a Lewis acid, a Lewis base, a Brønsted acid, or a Brønsted base.

Alternatively, in certain embodiments, the polymerization reaction is a cross-linking reaction of the hydrazide modified polymer, and involves reaction of the hydrazide moiety present in the polymer of step (iv) with a carboxylic acid moiety, or derivative thereof, or an aldehydic moiety (—CHO) also present in the polymer of step (iv), or in another polymer possessing at least one carboxylic acid moeity, or derivative thereof, or at least one aldehydic moiety (—CHO).

Polymerization/cross-linking of an acrylated polymer or a hydrazide modified polymer are just two exemplary ways to polymerize/crosslink the inventive polymers. The present invention contemplates many other ways of providing a polymer of step (iii), further modifying the polymer of step (iii), and polymerizing/cross-linking the modified polymer to provide a polymerized/cross-linked product; see generally Hennink and Van Nostrum, *Advanced Drug Delivery Reviews* 54 (2002) 13-36, the entirety of which is incorporated herein by reference.

In certain embodiments, the reaction of step (v) further comprises a suitable solvent. Suitable solvents include ethers, halogenated hydrocarbons, aromatic solvents, polar aprotic solvents, polar protic solvents, or mixtures thereof. In certain embodiments, the solvent comprises water, saline, phosphate-buffered saline (PBS), diethyl ether, dioxane, tetrahydrofuran (THF), dichloromethane (DCM), dichloroethane (DCE), chloroform, toluene, benzene, dimethylformamide (DMF), dimethylacetamide (DMA), dimethylsulfoxide (DMSO), N-methyl pyrrolidinone (NMP), or mixtures thereof.

In certain embodiments, the product of step (v) is water-soluble. In certain embodiments, the product of step (v) is not water-soluble. In certain embodiments, the product of step (v) is a hydrogel. In certain embodiments, the product of step (v) is a tough elastomer. In certain embodiments, the product of step (v) is a hydrated elastomer.

In certain embodiments, the reaction of step (v) is performed without solvent.

In certain embodiments, the reaction of step (v) is induced in vivo. In certain embodiments, the reaction of step (v) is induced in vivo by radical polymerization. In certain embodiments, the reaction of step (v) induced in vivo is photo-induced.

Additional Steps and Modifications

The present invention is also directed to a method of making an inventive polymer which includes a biologically active agent. The biologically active agent may be incorporated as a polymeric component, either via covalent or non-covalent association, or as an entrapped (e.g., encapsulated) moiety within the polymeric matrix.

Examples of certain modifications to the above method steps which may generate a polymer conjugated to a biologically active agent includes, but is not limited to:

(iii) reacting a polyol with a polycarboxylic acid to provide a polymer, and conjugating a polymer to a biologically active agent;

(iv) reacting a polymer of step (iii) with an acrylating compound to provide an acrylated polymer, and conjugating the acrylated polymer to a biologically active agent;

(iv) reacting a polymer of step (iii) with a dihydrazide compound to provide an hydrazide modified polymer, and conjugating the hydrazide modified polymer to a biologically active agent;

(iv) oxidizing a polymer of step (iii) to provide an oxidized polymer, and conjugating an oxidized polymer to a biologically active agent;

(v) polymerizing an acrylated polymer of step (iv) in the presence of a biologically active agent;

(v) cross-linking a hydrazide modified polymer of step (iv) in the presence of a biologically active agent;

(vi) providing a biologically active agent, and conjugating the biologically active agent to a polymerized product of step (v);

and/or (vi) providing a biologically active agent, and conjugating the biologically active agent to a cross-linked product of step (v).

Any of the above method steps (e.g., acrylation, dihydrazide chemistry, oxidation, polymerization, conjugation to a biologically active agent) may be combined to provide any number of different inventive polymers. Table 3 summarizes the above method steps and exemplary combinations thereof.

TABLE 3

|    | Step (iii) | Step (iv) | Step (v) | Additional steps |
|----|-----------|-----------|----------|------------------|
| 1  | polymer   |           |          |                  |
| 2  | polymer   |           |          | modification with a biologically active agent |
| 3  | polymer   | acrylation |         |                  |
| 4  | polymer   | acrylation |         | modification with a biologically active agent |
| 5  | polymer   | acrylation | polymerization |           |
| 6  | polymer   | acrylation | polymerization | modification with a biologically active agent |
| 7  | polymer   | oxidation |          |                  |
| 8  | polymer   | oxidation |          | reaction with a biologically active agent |
| 9  | polymer   | oxidation | reaction with a dihydrazide compound |   |
| 10 | polymer   | oxidation | reaction with a dihydrazide compound | reaction with a biologically active agent |
| 11 | polymer   | reaction with a dihydrazide compound |   |   |
| 12 | polymer   | reaction with a dihydrazide compound |   | reaction with a biologically active agent |
| 13 | polymer   | reaction with a dihydrazide compound | polymerization |   |
| 14 | polymer   | reaction with a dihydrazide compound | polymerization | reaction with a biologically active agent |
| 15 | polymer   | one batch: oxidation; and other batch: reaction with a dihydrazide compound | polymerization of the two batches |   |
| 16 | polymer   | one batch: oxidation; and other batch: reaction with a dihydrazide compound | polymerization of the two batches | reaction with a biologically active agent |
| 17 | polymer   | one batch: acrylation; and other batch: reaction with a dihydrazide compound | polymerization of the two batches |   |
| 18 | polymer   | one batch: acrylation; and other batch: reaction with a dihydrazide compound | polymerization of the two batches | reaction with a biologically active agent |

TABLE 3-continued

| Step (iii) | Step (iv) | Step (v) | Additional steps |
|---|---|---|---|
| 19 polymer | one batch: oxidation; and other batch: acrylation | polymerization of the two batches | |
| 20 polymer | one batch: oxidation; and other batch: acrylation | polymerization of the two batches | reaction with a biologically active agent |

The present invention will be more specifically illustrated by the following examples. However, it should be understood that the present invention is not limited by these examples in any manner.

EXAMPLES

Example 1

Xylitol Based Polymers

Biodegradable Waxy Polymers, Hydrogels, and Elastomers

The first step in the synthesis of all pre-polymers includes a polycondensation reaction. Xylitol and the polycarboxylic acid are melted under an inert atmosphere at a temperature of approximately 100-120° C. Then the polycondensation reaction is initiated after 6 hours, continuously stirring in vacuo. These thermoplastic pre-polymers can be divided based on their solubility in water. Water soluble prepolymers can be used as waxy polymer, or further processed into photo-crosslinkable and/or in situ crosslinkable hydrogels. The water insoluble pre-polymers can be used as a thermoplastic, waxy polymer, or further processed into elastomers, either through polycondensation, photopolymerization, and/or in situ polymerization.

Experiment 1a:
The water soluble pre-polymers are synthesized using xylitol and glutaric acid with a 1:1 molar ratio. The polycondensation was done at 100° C., for 5 hours in vacuo, resulting in a colorless, odorless syrup. This first product is also referred to as the water soluble waxy polymer, or poly-xylitol-glutaric acid (PXG 1:1).

Experiment 1b:
The water soluble pre-polymers are synthesized using xylitol and citric acid with a 1:1 molar ratio. The polycondensation was done at 100° C., for 3 hours in vacuo, resulting in a colorless, glassy thermoplastic polymer. This first product is referred to as the water soluble polymer, or poly-xylitol-citric acid (PXC 1:1).

Experiment 1c:
The available free hydroxyl and carboxyl groups on the water soluble waxy polymer were functionalized to yield photocrosslinkable and, or in situ crosslinkable hydrogels, using established chemistry. For instance, 5 grams of PXG 1:1 is dissolved in N,N-dimethyl formaldehyde (DMF) under anhydrous conditions. 50 mL anhydrous DMF was added to a flame dried round-bottom flask to make a 10% solution (w/v) of polymer. After adding 20 mg of DMAP, the reaction flask was placed in an ice bed over a stirring plate under nitrogen. Once cooled, "x" mol of acryloyl chloride (the value of "x" varies for any wanted degree of acrylation, which influences biodegradation and mechanical properties of the eventual polymer) and an equimolar triethylamine was added to start the reaction. The ice-bath was allowed to heat to room temperature overnight. This solution was filtered and the acrylated PXG 1:1 (PXGa 1:1) was precipitated in a 50:50 ethyl acetate/hexane solution. The precipitate was allowed to settle at −20° C. overnight and the solvents were decanted. The PXGa 1:1 was dissolved in PBS, ranging from 50% to 15% v/v, containing 0.5% Irgacure 2399832 photo-initiator. This was photopolymerized by exposure to ~4 mW/cm$^2$ ultraviolet light for 10 min using a longwave ultraviolet lamp (model 100AP, Blak-Ray), resulting in various hydrogels.

Experiment 1d:
A 1% w/v PXC solution in ddH$_2$O (200 mL) is filtered through a 0.22 micron filter. The molecular weight (MW) of a PXC polymer is around 4 kDa, so for a 20-fold excess of methacrylic anhydride, 10 mmol is needed. On ice and constant stirring, the methacrylic anhydride is added drop-wise. Drops in pH are corrected with 5 N NaOH and maintained at a pH of 8.0 as much as possible. The reaction is allowed to proceed for 24 hrs at 4° C. For purification, the macromers were extensively dialyzed in ddH$_2$O and the final product methacrylated PXC (PXCma 1:1) was obtained through freeze-drying. Original description of methacrylation of haluronic acid (HA) provided in Smeds K A and Grinstaff M W. J. Biomed Mater. Res. (2001) 54:115-121.

Experiment 1e.
A photopolymerized hydrogel network of PXCma is obtained by mixing a photoinitiator (0.05% w/v) and exposure to approximately 4 mW/cm$^2$ ultraviolet light for 10 min using a longwave ultraviolet lamp (model 100AP, Blak-Ray).

Experiment 1f.
The carboxyl and hydroxyl groups of the water soluble polymer, PXC 1:1 are functionalizable into an in situ crosslinkable hydrogel. The preparation of in situ crosslinkable PXC can be done as follows:

Periodate oxidation of PXC to obtain PXC-ALD: 1.0 g PXC (Mw 4 kDa) will be dissolved in H$_2$O at a concentration of 10 mg/ml. An aqueous solution of sodium periodate (0.5 M, 5 ml) will be added dropwise, and the reaction stirred for 2 h at room temperature in the dark. Ethylene glycol will be then added to inactivate any unreacted periodate. The reaction was stirred for 1 hour at ambient temperature, and the solution was purified by exhaustive dialysis (MWCO 1,000, Spectrapor membrane, Spectrum Laboratories, Rancho Dominguez, Calif.) against ddH$_2$O for 3 days, and the dry product obtained by freeze drying.

Modification of PXC with adipic dihydrazide to obtain PXC-ADH: 0.5 g of PXC (Mw 4 kDa) will be dissolved in ddH$_2$O to make a 5 mg/ml solution. To this solution will be added a 30-fold molar excess of ADH. The pH of the reaction mixture will be adjusted to 6.8 with 0.1 m NaOH and 0.1 m HCl. 0.78 g of EDC (5 mmol) and 0.77 g HOBt (5 mmol) will be dissolved in DMSO/H$_2$O (1:1 v/v, 5 ml each) and added to the reaction mixture. The pH of the solution will be adjusted to 6.8 and maintained by adding 0.1 N HCl for at least 4 h. The reaction will be allowed to proceed overnight. The pH will be subsequently adjusted to 7.0 and the reaction products exhaustively dialyzed (MWCO 1,000, SpectraJPor membrane) against $H_2O$. NaCl will be added to produce a 5% (w/v) solution and PXC-ADH will be precipitated in chloroform. The precipitate will be re-dissolved in $H_2O$ and dialyzed again to remove the salt. The purified product will be freeze dried and kept at 4° C.

As depicted in FIGS. 13A-13B, using 1-ethyl-3-[3-dimethylamino) propyl]carbodiimide (EDC) chemistry (steps 1), the carboxylic groups of the PXC polymer can be functionalised with amino(dihydrazide) and aldehyde containing groups (steps 2). Using 1-hydroxybenzotriazole (HOBt) to form an easy leaving group and adding adipic dihydrazide to the reaction mixture, adipic dihydrazide-PXC(PXC-A) can be formed. With N-hydroxysulfosuccinimide (sulfo-NHS), aminoacetaldehyde dimethyl acetal-PXC can be formed which can yield a PXC-aldehyde polymer (step 3) (PXC-B) with a mild acid treatment. The actual hydrogel network is formed when PXC-A and PXC-B are mixed together.

Experiment 2.

Preparation of an in situ crosslinkable PXC hydrogel is done by dissolving the PXC-ADH and PXC-ALD in $ddH_2O$ separately at a concentration of 20 mg/ml. Gels formed by mixing of solutions as narrated below.

Experiment 2a.

The water insoluble pre-polymers are synthesized using xylitol and sebacic acid with varying molar ratios. The polycondensation was done at 130° C., for 6 hours in vacuo, resulting in a hard, waxy water insoluble polymer. These products are also referred to as the water insoluble waxy polymers, or a 1:1 poly-xylitol-sebacic acid (PXS 1:1) or 1:2 poly-xylitol-sebacic acid (PXS 1:2), resembling the molar ratios used.

Experiment 2b.

The water insoluble waxy pre-polymers are melted at 120° C. and poured on wafers. Subsequently, the polycondensation was continued at 120° C. in vacuo for 3, 4, 7, and 10 days. This further polymerization of PXS 1:1 and PXS 1:2 resulted in tough biodegradable elastomers with Young's moduli ranging from 0.8 to 5.3 MPa.

Experiment 2c.

The available free hydroxyl and carboxyl groups on the water insoluble waxy polymers were functionalized to yield photocrosslinkable and/or in situ crosslinkable elastomers, using established acrylate chemistry. For instance, 5 grams of PXS 1:1 or 1:2 were dissolved in N,N-dimethyl formaldehyde (DMF) under anhydrous conditions. 50 mL anhydrous DMF was added to a flame dried round-bottom flask to make a 10% solution (w/v) of polymer. After adding 20 mg of DMAP, the reaction flask was placed in an ice bed over a stirring plate under nitrogen. Once cooled, "x" mol of acryloyl chloride [the value of "x" mol varies for any desired degree of acrylation which influences biodegradation and mechanical properties of the eventual polymer] and equimolar triethylamine was added to start the reaction. The ice-bath was allowed to heat to room temperature overnight. This solution was filtered, and the acrylated PXS polymers (PXSa 1:1 or PXSa 1:2) were precipitated in a 50/50 ethyl acetate/hexane solution. The precipitate was allowed to settle at −20° C. overnight and the solvents were decanted. The PXSa polymers were thoroughly mixed with 0.1 weight % UV photoinitiator 2,2-dimethoxy-2-phenyl-acetophenone and photopolymerized with the addition of ~4 mW/cm² ultraviolet light for 10 minutes using a longwave ultraviolet lamp (model 100AP, Blak-Ray).

Experiment 3.

During its residence in vivo, PXS 1:2 polymers remain completely transparent, whereas PXS 1:1, PXG 1:1, poly(diol-citrate) (PDC), and poly(glycerol-sebacate) (PGS) polymers became opaque.

Experiment 4.

During its residence in vivo, PXS 1:2 polymers exhibited little to no degradation at week 12.

Experiment 5.

Characteristics of PXS polymers. Increasing the sebacic acid to the polyol by 2-fold (xylitol:sebacic acid=1:2) has a dramatic influence on the crosslink density (or, Mc as a measure thereof, changes by 10-fold) and contact angle, which renders the elastomer PXS 1:2 with a much slower degradation profile than PXS 1:1. By increasing the crosslink density by adding more polycarboxylic acids, the crosslink density can be increased to a number which is not possible by merely changing the curing conditions of a PXS 1:1 polymer. This increase in crosslink density does not result in a brittle polymer. The strain till failure that can be put on this polymer (PXS 1:2) is still around 50% elongation, which is much more deformation it can recover from than other important polymers like collagen (which elongates to maximally 20% (Fratzl et al., *J. Struct. Biol.* 1998, 122, 119-22; Wang et al., *Theor. Appl. Fract. Mech.* 1997, 27, 1-12)), or poly(lactide), poly(glycolide), and their co-polymers, which only elongate a few percents. These above properties (degradation profile and mechanical properties) may be due to the fact that, since the hydroxyl: carboxyl groups are not 1:1 when the amount of the polycarboxylic acid is increased, it allows any free hydroxyls to participate in (extra) hydrogen bonding within the polymer backbone which might be responsible for the elastic properties.

Experiment 6.

Scanning Electrode Microscopy (SEM). SEM images were taken from the in vivo implants that were explanted at predetermined timepoints. As the polymer PXS 1:1 showed a clear erosion front from the outside towards the middle of the polymer network, one can argue that PXS 1:1 acts like a surface degrading polymer rather than a bulk-eroding polymer. Thus, mechanical properties will be more likely to be maintained in vivo during degradation.

PXS 1:2, however, did not show any disruption of its surface integrity (PXS shows no degradation after 12 weeks in vivo). Degradability can be precisely controlled by introducing more polycarboxylic acids which increase crosslink density and hydrophobicity.

Observed cell attachment and subsequent growth into monolayer for PXS 1:1.

Example 2

Biodegradable Xylitol-Based Polymers

In this Example, we describe xylitol-based polymers. Polycondensation of xylitol with water soluble citric acid yielded biodegradable, water soluble polymers. Acrylation of this polymer resulted in an elastomeric photocrosslinkable hydrogel. Polycondensation of xylitol with the water insoluble sebacic acid monomer produced tough biodegradable elastomers, with tunable mechanical and degradation properties. These xylitol-based polymers exhibited excellent in vitro and in vivo biocompatibility compared to the well-characterized poly(L-lactic-co-glycolic acid) (PLGA), and are promising biomaterials.

Figure 1:
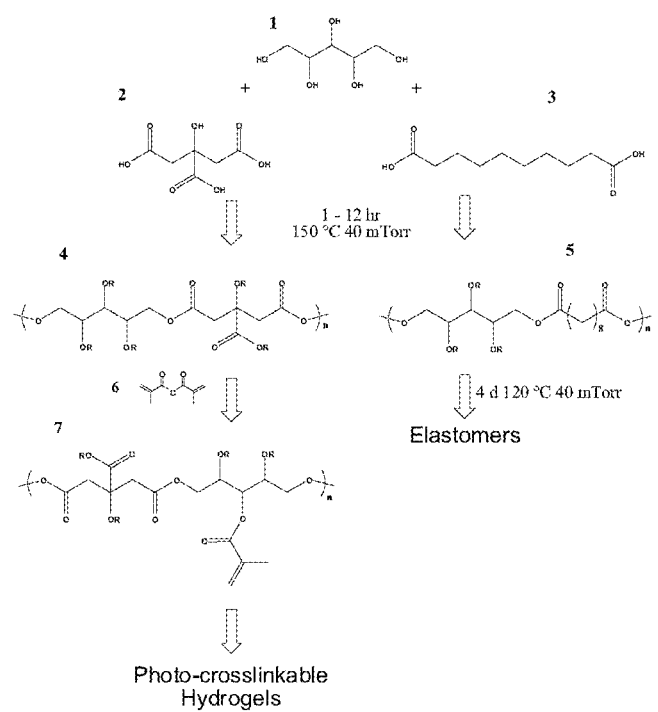
FIG. 1. Schematic representation of the general synthetic scheme of xylitol-based polymers. Xylitol (1), was polymerized with citric acid (2) or sebacic acid (3) into poly(xylitol-co-citrate) (PXC) (4), and poly(xylitol-co-sebacate) (PXS) (5). Further polycondensation of PXS yielded elastomers. Photo-crosslinkable hydrogels were obtained by acrylation of PXC in ddH$_2$O using methacrylic anhydride (6) to yield PXC-methacrylate (PXCma) (7). PXCma was polymerized into a hydrogel by free radical polymerization using a photo-initiator. A simplified representation of the polymers is shown. R can be H, OCH$_2$(CH(OR))$_3$CH$_2$OR (xylitol), —CO(CH$_2$)$_6$COOR (sebacic acid), CO(CH$_2$)ROC(COOR)(CH$_2$)COOR (citric acid), or —C(CH$_3$)=CH$_2$ (methacrylate group).

Sebacic acid (a metabolite in the oxidation of fatty acids) and citric acid (a metabolite in the Krebs cycle) were chosen as the reacting monomers for their proven biocompatibility (Y. Wang, G. A. Ameer, B. J. Sheppard, R. Langer, A tough biodegradable elastomer. *Nat Biotechnol* 2002, 20, (6), 602-606; J. Yang, A. R. Webb, G. A. Ameer, Novel Citric Acid-Based Biodegradable Elastomers for Tissue Engineering. *Adv Mater* 2004, 16, (6), 511-516; each of which is incorporated herein by reference) and they are FDA approved compounds as well. Polycondensation of xylitol with sebacic acid produced water insoluble waxy pre-polymers (designated PXS pre-polymer). PXS pre-polymers with a monomer ratio of xylitol:sebacic acid of 1:1 and 1:2 were synthesized and had a weight average molecular weights ($M_w$) of 2,443 g/mol ($M_n$=1,268 g/mol, PDI 1.9) and 6,202 g/mol ($M_n$=2,255 g/mol, PDI 2.7), respectively. The PXS pre-polymers were melted into the desired form and cured by polycondensation (120° C., 40 mTorr for 4 days) to yield low modulus (PXS 1:1)—and high modulus (PXS 1:2) elastomers. PXS pre-polymers are soluble in ethanol, dimethyl sulfoxide, tetrahydrofuran and acetone, which allows for processing into more complex geometries. Polycondensation of xylitol with citric acid resulted in a water soluble pre-polymer (designated PXC pre-polymer), of which the $M_w$ was 298,066 g/mol and the $M_n$ was 22,305 g/mol (PDI 13.4), compared to linear poly(ethylene glycol) (PEG) standards. To cross-link the water soluble PXC pre-polymer in an aqueous environment, we functionalized the hydroxyl groups of PXC with vinyl groups (designated PXCma) using methacrylic anhydride, as previously described for photo-crosslinkable hyaluronic acid (J. A. Burdick, C. Chung, X. Jia, M. A. Randolph, R. Langer, Controlled Degradation and Mechanical Behavior of Photopolymerized Hyaluronic Acid Networks. *Biomacromolecules* 2005, 6, 386-391; K. A. Smeds, A. Pfister-Serres, D. Miki, K. Dastgheib, M. Inoue, D. L. Hatchell, M. W. Grinstaff, Photocrosslinkable polysaccharides for in situ hydrogel formation. *J Biomed Mater Res* 2001, 54, (1), 115-121; each of which is incorporated herein by reference). During this reaction, the $M_w$ and $M_n$ of the polymer did not change appreciably. The PXCma pre-polymer was photopolymerized in a 10% w/v aqueous solution using a photoinitiator. This is referred to as the PXCma hydrogel. The synthetic route of these polymers is summarized in FIG. 1.

Fourier-Transformed Infrared Spectroscopy (FT-IR) confirmed ester bond formation in all polymers (FIG. 2A), with a stretch at 1,740 $cm^{-1}$ which corresponds to ester linkages. A broad stretch was also observed at approximately 3,448 $cm^{-1}$ which corresponds to hydrogen bonded hydroxyl groups. The FT-IR of PXCma illustrated an additional stretch at 1,630 $cm^{-1}$ compared to the spectrum of PXC, which is associated with the vibration of the vinyl groups. $^1$H-NMR revealed a polymer composition of 1.10:1 xylitol to sebacic acid for PXS 1:1, 1.08:2 xylitol to sebacic acid for PXS 1:2, and 1.02:1 xylitol to citric acid for PXC. The degree of substitution of xylitol monomers with a methacrylate group was found to be 44% for the PXCma pre-polymer (average percentage of xylitol monomers modified with a methacrylate group).

Figure 2:
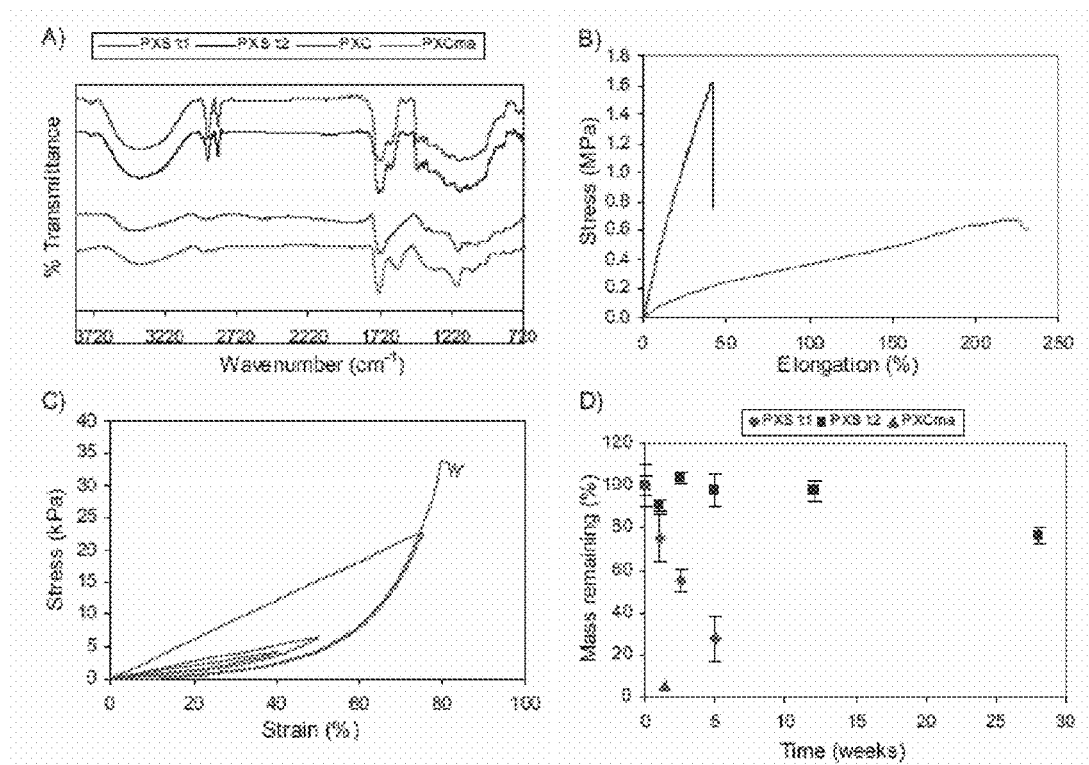
FIG. 2. (A) FTIR analysis of xylitol-based polymers. (B) Typical tensile stress versus strain curve of the PXS elastomers. (C) Typical compression stress versus strain plot of the 10% w/v PXCma hydrogel, with cyclic compression at 40, 50, 75%, to failure (at ~80%). (D) In vivo mass loss over time.

Ideally, the mechanical properties of an implantable biodegradable device should match its implantation site to minimize mechanical irritation to surrounding tissues and should permit large deformations (Y. Wang, G. A. Ameer, B. J. Sheppard, R. Langer, A tough biodegradable elastomer. *Nat Biotechnol* 2002, 20, (6), 602-606; incorporated herein by reference), inherent to the dynamic in vivo environment. All xylitol-based polymers revealed elastic properties (FIG. 2B,C). The PXS 1:1 elastomer had an average Young's modulus of 0.82±0.15 MPa with an average elongation at failure of 205.2±55.8% and an ultimate tensile stress of 0.61±0.19 MPa. Increasing the crosslink density by doubling the sebacic acid monomer feed ratio resulted in a stiffer elastomer. The PXS 1:2 elastomer revealed a Young's modulus of 5.33±0.40 MPa, had an average elongation at failure of 33.1±4.9% and an ultimate tensile stress of 1.43±0.15 MPa. The stress versus strain curves of PXS 1:1 and PXS 1:2 are typical for low and high modulus elastomers (FIG. 2B) (Y. Wang, G. A. Ameer, B. J. Sheppard, R. Langer, A tough biodegradable elastomer. *Nat Biotechnol* 2002, 20, (6), 602-606; incorporated herein by reference). DSC showed a glass transition temperature of 7.3 and 22.9° C. for PXS 1:1 and 1:2 respectively, indicating that these elastomers are in a rubbery state at room- and physiological temperature. The mechanical properties of PXS 1:1 elastomer is similar to a previously developed elastomer, composed of glycerol and sebacic acid (Y. Wang, G. A. Ameer, B. J. Sheppard, R. Langer, A tough biodegradable elastomer. *Nat Biotechnol* 2002, 20, (6), 602-606), but showed a higher Young's modulus for a comparable elongation. Altering monomer feed ratios of sebacic acid in PXS elastomers resulted in a wide range of crosslink densities, whilst maintaining elastomeric properties. The molecular weight between crosslinks (M) ranged in the order of a magnitude (from 10517.4±102 g/mol for PXS 1:1 to 1585.1±43 g/mol for PXS 1:2, Table 1) and decreased as more crosslink entities were introduced. Such an appreciable range can otherwise not be obtained by changing condensation parameters of PXS 1:1. The increased crosslink density in PXS 1:2 also resulted in significantly less equilibrium hydration as determined by mass differential of PXS 1:2 in dd$H_2O$ (24 hrs at 37° C.), compared to PXS 1:1 (4.1±0.3% and 12.6±0.4% respectively), as well as a lower sol content (i.e., fraction of free, unreacted macromers within the elastomeric construct, Table 1). In concert with this finding, adding more sebacic acid molecules within the polymer affects the water-in-air contact angles (PXS 1:1 26.5±3.6°, PXS 1:2 52.7±5.7°, after 5 minutes), as more aliphatic monomers are being introduced.

TABLE 1

Physical properties of xylitol-based polymers (PXS 1:1 and 1:2 are elastomers, PXCma is a photocured hydrogel). $M_c$: the molecular weight between crosslinks, calculated with Eqn. 1 for the PXS elastomers, and Eqn. 2 and 3 for the PXCma hydrogel (See Experimental).

| Polymer | Young's/ Compression Modulus (kPa) | Elongation/ Compression at break (%) | Equilibrium hydration by mass (%) | Sol Content (%) | Contact Angle (°) | Polymer Density (g/cm$^3$) | Crosslink Density (mol/m$^3$) | $M_c$ (g/mol) |
|---|---|---|---|---|---|---|---|---|
| PXS 1:1 | 820 ± 150 | 205.2 ± 55.8 | 12.6 ± 0.4 | 11.0 ± 2.7 | 26.5 ± 3.6 | 1.18 ± 0.02 | 112.2 ± 30.5 | 10,517.4 ± 102.1 |
| PXS 1:2 | 5,330 ± 400 | 33.1 ± 4.9 | 4.1 ± 0.3 | 1.2 ± 0.8 | 52.7 ± 5.7 | 1.16 ± 0.02 | 729.32 ± 57.3 | 1,585.1 ± 43.7 |
| PXCma | 5.8 ± 1.2 | 79.9 ± 5.6 | 23.9 ± 6.2 | 31.7 ± 10.6 | n/a | 1.51 ± 0.05 | 136.4 ± 27.9 | 11,072.1 ± 115.8 |

The equilibrium hydration of PXCma hydrogels determined by mass was 23.9±6.2% after 24 hrs at 37° C. Volumetric swelling analysis revealed that the polymer volume fraction in the relaxed state ($v_r$), which is immediately after crosslinking, but before equilibrium swelling, was 6.9±0.1% and decreased to 5.8±0.2% at equilibrium swelling, designated the polymer volume fraction in the swollen state ($v_s$). Cyclic compression up to 75% strain of the PXCma hydrogel was possible without permanent deformation, and only limited hysteresis was observed during cyclic conditioning, revealing the elastic properties over a wide range of strain conditions. The PXCma hydrogel failed at a compressive strain of 79.9±5.6% and showed a compressive modulus of 5.84±1.15 kPa (FIG. 2C). The mechanical properties of PXCma hydrogel discs were similar to photocured hyaluronic acid hydrogels (50 kDa 2-5% w/v), as previously reported (J. A. Burdick, C. Chung, X. Jia, M. A. Randolph, R. Langer, Controlled Degradation and Mechanical Behavior of Photopolymerized Hyaluronic Acid Networks. *Biomacromolecules* 2005, 6, 386-391; incorporated herein by reference), although the PXCma hydrogel showed a lower compression modulus for a similar ultimate compression stress. The physical properties of the elastomers and the hydrogel are summarized in Table 1.

Xylitol-based biopolymers degrade in vivo. After subcutaneous implantation, approximately 5% of the mass of the hydrogel was found after 10 days. The degradation rate of PXS elastomers varied according to the stoichiometric ratios. PXS 1:1 had fully degraded after 7 weeks. However, after 28 weeks, 76.7±3.7% still remained of the PXS 1:2 elastomer (FIG. 2D). This demonstrates that the in vivo degradation kinetics of xylitol-based elastomers can be tuned in addition to crosslink density, surface energy, and equilibrium hydration. Thus, this polymer platform describes a range in physical properties, which allow for a tuneable in vivo degradation rate. The PXS 1:2 elastomers were optically transparent during the first 15 weeks in vivo and turned opaque upon degradation (seen at week 28).

Figure 3:
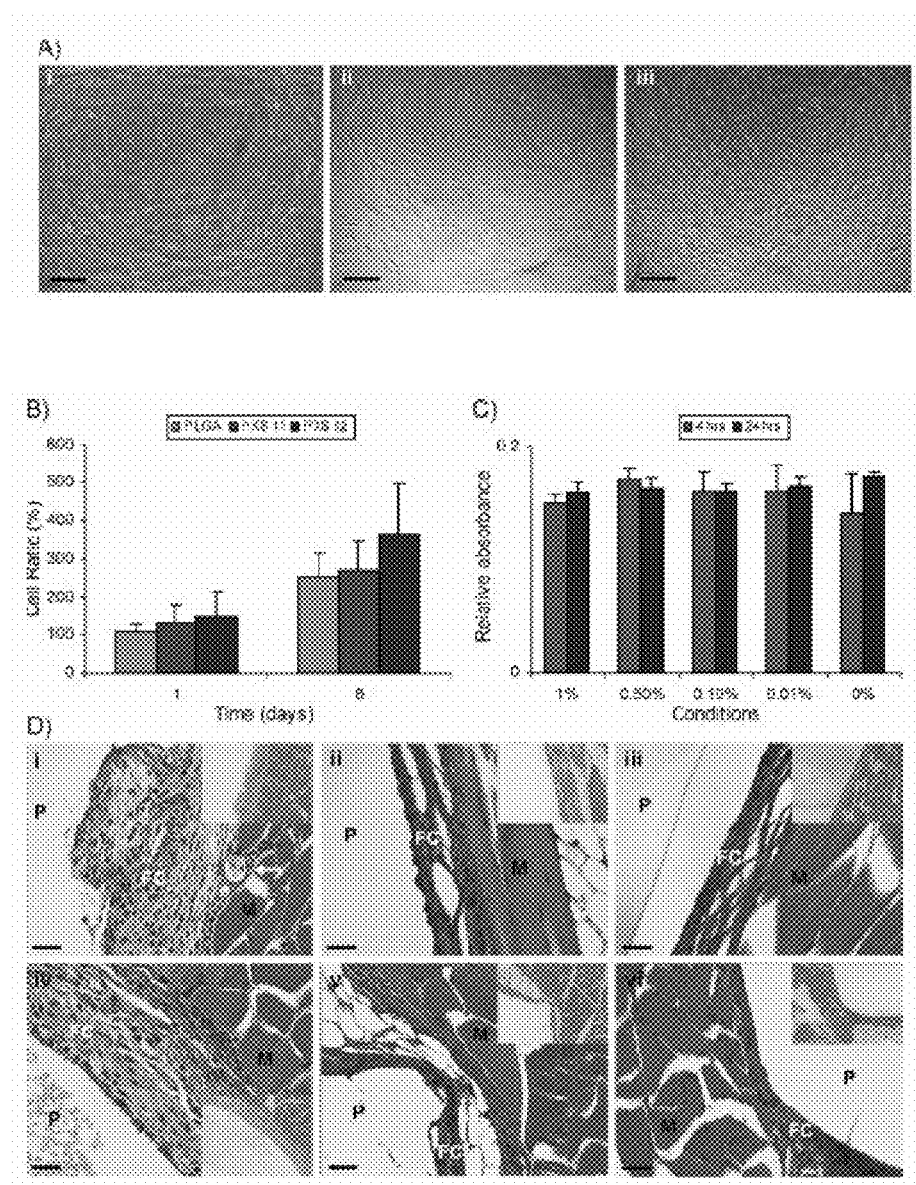
FIG. 3. (A) Phase contrast images (10×) of human primary fibroblasts after 5 days of in vitro culture, seeded on PLGA (i), PXS 1:1 (ii) and PXS 1:2 (iii). Bars represent 250 μm. (B) Growth rates of fibroblasts on PLGA, PXS 1:1 and PXS 1:2, expressed as cell differential. (C) MTT assay of fibroblasts exposed to different PXCma pre-polymer fractions in their growth medium. (D) Representative images of H&E stained sections of subcutaneous implantation sites of (i) PLGA discs, (ii) PXS 1:1 discs, (iii) PXS 1:2 discs, (iv) 10% w/v PXCma hydrogel discs, 1 week after implantation. (v) Shows PXS 1:1 implantation site at week 5 (~73% had degraded), and (vi) shows PXS 1:2 at week 12 (no degradation). The arrow (i) points to a vessel of the fibrous capsule surrounding the PLGA implant where some perivascular infiltration is observed. P=polymer, FC=fibrous capsule, M=muscle. Inserts are 5× overviews, full images are magnified 25×. Bars represent 100 μm.

Xylitol-based polymers are biocompatible in vitro and in vivo, compared to the prevalent synthetic polymer PLGA (65/35 LA/GA, high $M_w$). Regardless of the eventual in vivo application of these xylitol based polymers, a normal wound healing process upon implantation is mandatory, and is orchestrated by residential fibroblasts. We therefore chose primary human foreskin fibroblasts (HFF) to test in vitro biocompatibility. All xylitol-based elastomers and hydrogels were transparent polymers, which facilitated characterization of cell-biomaterial interactions. HFFs attached readily to PXS elastomers and proliferated into a confluent monolayer in 6 days. HFFs cultured on PXS elastomers showed a similar cell morphology and proliferation rate compared to HFFs grown on PLGA (FIG. 3A,B). There was no cell attachment on PXCma hydrogels. It is known that cells in general do not attach to hydrogels, unless attachment promoting entities are incorporated (D. L. Hem, J. A. Hubbell, Incorporation of adhesion peptides into nonadhesive hydrogels useful for tissue resurfacing. *J Biomed Mater Res* 1998, 39, 266-276; incorporated herein by reference). We therefore examined the cytotoxicity of soluble PXCma pre-polymer in the culture media. HFFs exposed for 4 or 24 hrs to PXCma pre-polymer fractions in the growth media (0.01%-1% w/v) were not compromised in their mitochondrial metabolism, as tested by the MTT assay, compared to HFFs with no PXCma in the growth media (FIG. 3C). Upon subcutaneous implantation, none of the animals showed an abnormal post-operative healing process, as assessed clinically and by histology. The PXS 1:1 and 1:2 discs were encased in a translucent tissue capsule after 1 week, which did not become more substantial throughout the rest of the study. Histological sections confirmed that the polymer-tissue interface was characterized by a mild fibrous capsule formation (FIG. 3D ii and iii). No abundant inflammation in the surrounding tissues was seen, and the sections showed a quiet polymer-tissue interface, which is characteristic for the PXS elastomers after the first week in vivo. Also, no perivascular infiltration was noted in the surrounding tissues of the PXS discs. This quiescent tissue response was evident when compared to the tissues in contact with the PLGA implants (FIG. 3Di). Surrounding the PLGA implants, a more substantial vascularized fibrous capsule was seen, with minor perivascular infiltration (arrow). A comparable thickness of fibrous capsule formation was noted for the 10% PXCma hydrogel at day 10 (FIG. 3Div). No PXCma hydrogel was found at 14 days after repetitive sectioning of the explanted tissue. Long term histological sections of PXS 1:1 and 1:2 at week 5 and 12 respectively (FIG. 3Dv and vi), demonstrated that even upon degradation the fibrous capsule remained quiescent: At week 5 the PXS 1:1 elastomer had degraded approximately 73%, whereas the PXS 1:2 polymer showed no degradation at all at week 12. Thus, xylitol-based polymers exhibited excellent biocompatibility as compared to PLGA.

Our goal was to develop a polymer synthesis scheme that requires very simple adjustments in chemical composition to achieve a wide range in material properties. We have described a process for the synthesis of xylitol-based polymers. Xylitol is well studied in terms of biocompatibility and pharmacokinetics in humans (L. Sestoft, An evaluation of biochemical aspects of intravenous fructose, sorbitol and xylitol administration in man. *Acta Anaesthesiol Scand Suppl* 1985, 82, 19-29; H. Talke, K. P. Maier, [Glucose, fructose, sorbitol and xylitol metabolism in man]. *Infusionstherapie* 1973, 1, (1), 49-56; each of which is incorporated herein by reference). It is a metabolic intermediate in mammalian carbohydrate metabolism with a daily endogenous production of 5-15 g in the adult human (E. Winkelhausen, S. Kuzmanova, Microbial Conversion of D-Xylose to Xylitol. *J Ferment Bioeng* 1998, 86, (1), 1-14; incorporated herein by reference). The entry into metabolic pathways is slow and independent of insulin, and does not cause rapid fluctuations of blood glucose levels (S. S, Natah, K. R. Hussien, J. A. Tuominen, V. A. Koivisto, Metabolic response to lactitol and xylitol in healthy men. *Am. J. Clin. Nutr.* 1997, 65, (4), 947-950; incorporated herein by reference). As a monomer, xylitol is an important compound in the food industry where it has an established history as a sweetener with proven anti-cariogenic activity (E. Honkala, S. Honkala, M. Shyama, S. A. Al-Mutawa, Field trial on caries prevention with xylitol candies among disabled school students. *Caries Res* 2006, 40, (6), 508-513; incorporated herein by reference). Moreover, it has an anti-microbial effect on upper airway infections caused by Gram positive streptococci (M. Uhari, T. Kontiokari, M. Koskela, M. Niemelä, Xylitol chewing gum in prevention of acute otitis media: double blind randomised trial. BMJ 1996, 313, (7066), 1180-1184; M. Uhari, T. Tapiainen, T. Kontiokari, Xylitol in preventing acute otitis media. *Vaccine* 2000, 19, (Suppl 1), S144-147; L. Durairaj, J. Launspach, J. L. Watt, Z. Mohamad, J. Kline, J. Zabner, Safety assessment of inhaled xylitol in subjects with cystic fibrosis. *J Cyst Fibros* 2007, 6, (1), 31-34; J. Zabner, M. P. Seiler, J. L. Launspach, P. H. Karp, W. R. Kearney, D. C. Look, J. J. Smith, M. J. Welsh, The osmolyte xylitol reduces the salt concentration of airway surface liquid and may enhance bacterial killing. *Proc Natl Acad Sci USA.* 2000, 97, (21), 1161-11619; each of which is incorporated herein by reference). Although xylitol has been studied in polymer synthesis, others have utilized it typically as an initiator (Q. Hao, L. F., Q. Li, Y. Li, L. Jia, J. Yang, Q. Fang, A. Cao, Preparation and crystallization kinetics of new structurally well-defined star-shaped biodegradable poly(L-lactide)s initiated with diverse natural sugar alcohols. *Biomacromolecules* 2005, 6, (4), 2236-2247; incorporated herein by reference), or altered xylitol to yield linear polymers by protecting three of the five functional groups (M. Gracia Garcia-Martin, E. Benito Hernandez, R. Ruiz Perez, A. Alla, S. Munoz-Guerra, J. A. Galbis, Synthesis and Characterization of Linear Polyamides Derived from L-Arabinitol and Xylitol. *Macromolecules* 2004, 37, 5550-5556; incorporated herein by reference). Xylitol-based polymers expose functional groups available for functionalization as shown here. They were produced in sub-kilogram quantities without the use of organic solvents or cytotoxic additives. Xylitol-based polymers are endotoxin-free and do not impose a potential immunological threat like biological polymers extracted from tissues or produced by bacterial fermentation, such as collagen and hyaluronic acid (L. R. Ellingsworth, F. DeLustro, J. E. Brennan, S. Sawamura, J. McPherson, The human immune response to reconstituted bovine collagen. *J Immunol* 1986, 136, (3), 877-882; J. R. Lupton, T. S. Alster, Cutaneous hypersensitivity reaction to injectable hyaluronic acid gel. *Dermatol Surg* 2000, 26, (2), 135-137; each of which is incorporated herein by reference). In addition, the mechanical properties of xylitol-based elastomers fall close to, or are within biological values of several tissues, such as acellular peripheral nerve (G. H. Borschel, K. F. Kia, W. M. Kuzon Jr., R. G. Dennis, Mechanical Properties of Acellular Peripheral Nerve. *J Surg Res* 2003, 114, 133-139; incorporated herein by reference), small diameter arteries (V. Clerin, J. W. Nichol, M. Petko, R. J. Myung, W. Gaynor, K. J. Gooch, Tissue Engineering of Arteries by Directed Remodeling of Intact Arterial Segments. *Tissue Eng* 2003, 9, (3), 461-472; incorporated herein by reference), cornea (J. O. Hjortdal, Regional Elastic Performance of the Human Cornea. *J Biomech* 1996, 29, (7), 931-942; incorporated herein by reference), and intervertebral discs (D. M. Skrzypiec, P. Pollintine, A. Przybyla, P. Dolan, M. A. Adams, The Internal Mechanical Properties of Cervical Intervertebral Discs as Revealed by Stress Profilometry. *Eur Spine J* 2007, 16, (10), 1701-1709; incorporated herein by reference). In this Example, we show three examples of possible polymers based on this monomer. Potential combinations in chemical composition of xylitol-based polymers are numerous and therefore it provides a platform to tune mechanical properties, degradation profile, and cell attachment.

Experimental

Synthesis and Characterization of the Polymers.

All chemicals were purchased from Sigma-Aldrich unless stated otherwise. Appropriate molar amounts of the polyol and reacting acid monomer were melted in a round bottom flask at 150° C. under a blanket of inert gas, and stirred for 2 hrs. Vacuum (~50 mTorr) was applied yielding the pre-polymers PXS 1:1 (12 hrs), PXS 1:2 (6 hrs) and PXC (1 hr). The PXC polymer was dissolved in ddH$_2$O and lyophilized. Methacrylated PXC pre-polymer (PXCma) was synthesized by the addition of methacrylic anhydride in a ~20-fold molar excess as previously described for the methacrylation of hyaluronic acid (K. A. Smeds, A. Pfister-Serres, D. Miki, K. Dastgheib, M. Inoue, D. L. Hatchell, M. W. Grinstaff, Photocrosslinkable polysaccharides for in situ hydrogel formation. *J Biomed Mater Res* 2001, 54, (1), 115-121; incorporated herein by reference), dialyzed in ddH$_2$O (M$_w$ cutoff 1 kDa) and lyophilized. PXCma hydrogels were fabricated by dissolving 10% w/v PXCma in PBS containing 0.05% w/v 2-methyl-1-(4-(hydroxyethoxy)phenyl)-2-methyl-1-propanone (Irgacure 2959, 12959) as the photo-initiator and exposure of ~4 mW/cm$^2$ ultraviolet light (model 100AP, Blak-Ray). All PXS 1:1 and 1:2 elastomers were produced by further polycondensation (120° C., 140 mTorr for 4 days). The pre-polymers were sized using gel permeation chromatography using THF or filtered ddH$_2$O on Styragel columns (series of HR-4, HR-3, HR-2, and HR-1, Waters, Milford, Mass., USA). FT-IR analysis was carried out on a Nicolet Magna-IR 550 spectrometer. $^1$H-NMR spectra were obtained of the PXS pre-polymers in C$_2$D$_6$O, and of the PXCma pre-polymers in D$_2$O on a Varian Unity-300 NMR spectrometer. The chemical composition of the pre-polymers was determined by calculating the signal integrals of xylitol, and compared to the signal integrals of sebacic acid or citric acid. The signal intensities showed peaks of —OC$\underline{H}_2$(C$\underline{H}$(OR))$_3$C$\underline{H}_2$O— at 3.5-5.5 ppm from xylitol, —C$\underline{H}_2$— at 2.3-3.3 ppm from citric acid, and peaks of —COC$\underline{H}_2$C$\underline{H}_2$C$\underline{H}_2$— at 1.3, 1.6 and 2.3 ppm from sebacic acid. The final degree of substitution after acrylation of the PXC pre-polymer was calculated by the signal integral of the protons associated with —C(C$\underline{H}_3$)=C$\underline{H}_2$ at 1.9, 5.7 and 6.1 ppm from the methacrylate groups. Tensile tests were performed on hydrated (ddH$_2$O at 37° C.>24 h) dog-bone shaped polymer strips and conducted on an Instron 5542 (according to ASTM standard D412-98a). Compression analysis of the photo-crosslinked PXCma hydrogels was performed as previously described (K. A. Smeds, A. Pfister-Serres, D. Miki, K. Dastgheib, M. Inoue, D. L. Hatchell, M. W. Grinstaff, Photocrosslinkable polysaccharides for in situ hydrogel formation. *J Biomed Mater Res* 2001, 54, (1), 115-121; incorporated herein by reference). Differential scanning calorimetry (DSC) was done as previously reported (C. L. E. Nijst, J. P. Bruggeman, J. M. Karp, L. Ferreira, A. Zumbuehl, C. J. Bettinger, R. Langer, Synthesis and Characterization of Photocurable Elastomers from Poly(glycerol-co-sebacate). *Biomacromolecules* 2007, 8, (10), 3067-3073; incorporated herein by reference). The mass density was measured using a pycnometer (Humboldt, MFG. CO). Crosslink density (n) and M$_c$ were calculated from the following equations for an ideal elastomer (P. J. Flory, *Principals of Polymer Chemistry*. Cornell University Press: New York, 1953; incorporated herein by reference):

$$n = \frac{E_0}{3RT} = \frac{\rho}{M_c} \qquad \text{Eqn. 1}$$

where E$_0$ is the Young's modulus, R the universal gas constant, T temperature and ρ is the mass density. This rubber-elasticity theory can also be utilized to calculate the effective M$_c$ for hydrogels that reveal elastic behavior and which were prepared in the presence of a solvent, according to Peppas et al. (N. A. Peppas, J. Z. Hilt, A. Khademhosseini, R. Langer, Hydrogels in Biology and Medicine: From Molecular Principles to Bionanotechnology. *Adv Mater* 2006, 18, 1345-1360; incorporated herein by reference).

$$\tau = \frac{\rho RT}{M_c}\left(1 - \frac{2M_c}{M_n}\right)\left(a - \frac{1}{a^2}\right)\left(\frac{v_s}{v_r}\right)^{\frac{1}{3}} \qquad \text{Eqn. 2}$$

where τ is the compression modulus of the hydrogel, $v_s$ (0.058±0.002) is the polymer volume fraction in the swollen state, and $v_r$ (0.069±0.001) is the polymer volume fraction in the relaxed state. For an isotropically swollen hydrogel, the elongation ratio (α) is related to the swollen polymer volume fraction:

$$\alpha = v_s^{1/3} \qquad \text{Eqn. 3}$$

The water-in-air contact angle measurements were carried out as previously mentioned (Y. Wang, G. A. Ameer, B. J. Sheppard, R. Langer, A tough biodegradable elastomer. *Nat Biotechnol* 2002, 20, (6), 602-606). Degradation of the explanted polymers was determined by mass differential, calculated from the polymer's dry weight at t, and compared to the dry weight at the start of the study. All data were obtained from at least four samples, and are expressed as means±standard deviation.

In Vitro and In Vivo Biocompatibility.

Primary human foreskin fibroblasts (HFF, ATCC, Manassas, Va., USA) were cultured in growth media, as previously described (C. L. E. Nijst, J. P. Bruggeman, J. M. Karp, L. Ferreira, A. Zumbuehl, C. J. Bettinger, R. Langer, Synthesis and Characterization of Photocurable Elastomers from Poly (glycerol-co-sebacate). *Biomacromolecules* 2007, 8, (10), 3067-3073). Glass Petri dishes (60 mm diameter) contained 3 grams of cured elastomers (120° C., 140 mTorr for 4 days). Petri dishes prepared with a 2% w/v PLGA (65/35, high $M_w$, Lakeshore Biomedical, Birmingham, Ala., USA) solution in dichloromethane at 100 uL/cm² and subsequent solvent evaporation served as control. Washes with sterile PBS were done before the polymer loaded dishes were sterilized by UV radiation. Cells were seeded (at 2.000 cells/cm²) in the biomaterial-laden dishes, without prior incubation of the polymers with growth media. Cells were allowed to grow to confluency and imaged at 4 hrs, and 1, 3, 5 and 6 days after initial seeding. Phase micrographs of cells were taken at 10× magnification using Axiovision software (Zeiss, Germany). For cell proliferation measurements, randomly picked areas were imaged and cells were counted. That cell number was expressed as the percentage increase of cells compared after initial seeding, designated cell differential. To assess cytotoxicity of the PXCma macromers, cells were seeded in tissue culture treated polystyrene dishes at 10.000 cells/cm² and allowed to settle for 4 hrs. After a gentle wash with sterile PBS, 1%, 0.5%, 0.1% and 0.01% w/v of PXCma in growth media was added for 4 or 24 hrs. Cell viability via mitochondrial metabolism was measured using the methylthiazoletetrazolium (MTT) assay as previously reported (Y. Wang, G. A. Ameer, B. J. Sheppard, R. Langer, A tough biodegradable elastomer. *Nat Biotechnol* 2002, 20, (6), 602-606). The statistical significance between two sets of data was calculated using a two-tailed Student's t-test. For the in vivo biocompatibility and degradation study, elastomeric discs d=10 mm, h=1 mm were implanted. PLGA pellets were melt-pressed (0.3 g, 172° C., 5000 MPa) into a mold (d=10 mm, h=1 mm) using a Carver Hydraulic Unit Model #3912-ASTM (Carver, Inc. Wabash, Ind.). Female Lewis rats (Charles River Laboratories, Wilmington, Mass.) weighing 200-250 grams were housed in groups of 2 and had access to water and food ad libitum. Animals were cared for according to the protocols of the Committee on Animal Care of MIT in conformity with the NIH guidelines (NIH publication #85-23, revised 1985). The animals were anaesthetized using continuous 2% isoflurane/ $O_2$ inhalation. The implants were introduced by two small midline dorsal incisions, and two polymer formulations (each on one side) were placed in subcutaneous pockets created by lateral blunt dissection. The skin was closed with staples. Per time point, three rats were sacrificed, from which four implants were analyzed for the degradation study, and two implants were resected en bloc with surrounding tissue and fixed in formalin-free fixative (Accustain). These specimens were embedded in paraffin after a series of dehydration steps in ethanol and xylene. Sequential sections (8-15 µm) were stained with hematoxilyn and eosine (H&E) and histology was evaluated by two medical doctors (JPB, DSK). Throughout the study, all rats remained in good general health as assessed by their weight gain.

Example 3

Biodegradable Poly(polyol sebacate) Polymers

In this Example, polyols were reacted with sebacic acid, yielding a family of thermoset poly(polyol sebacate) (PPS) polymers. Monomers of PPS polymers have the potential to be metabolized in vivo since sebacic acid is a metabolite in fatty acid oxidation and polyols are intermediates in mammalian carbohydrate metabolism. Polyols such as xylitol, sorbitol, mannitol, and maltitol are biocompatible, FDA approved, and are metabolized in an insulin-independent manner (K. C. Elwood, Methods available to estimate the energy values of sugar alcohols. *Am J Clin Nutr* 1995, 62 (Suppl), 1169-1174; S. S, Natah, K. R. Hussien, J. A. Tuominen, V. A. Koivisto, Metabolic response to lactitol and xylitol in healthy men. *Am J Clin Nutr* 1997, 65, (4), 947-950; L. Sestoft, An evaluation of biochemical aspects of intravenous fructose, sorbitol and xylitol administration in man. *Acta Anaesthesiol Scand Suppl* 1985, 82, 19-29; each of which is incorporated herein by reference). The functionality and physical properties of the different polyols influenced polymer properties. Stoichiometry further allowed for tuning chemical, physical and mechanical properties, as well as in vitro and in vivo degradation rates. PPS polymers show biocompatibility similar to PLGA, and may be promising biomaterials in biomedical applications such as reconstructive surgery and tissue engineering.

Materials and Methods

Synthesis and Characterization of PPS Polymers

Figure 4:
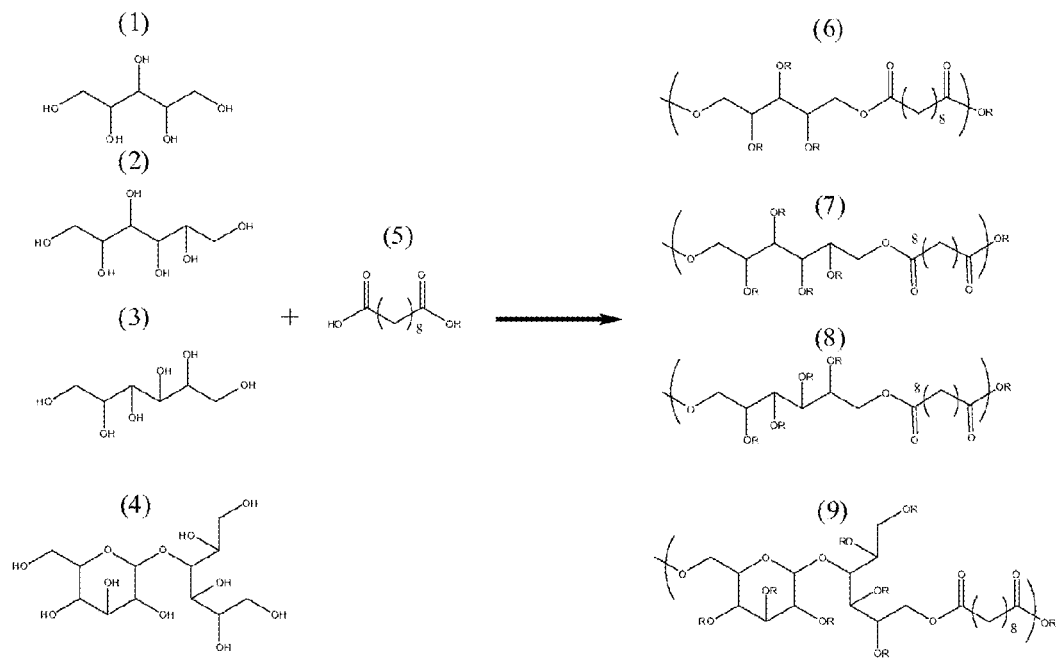
FIG. 4. General synthetic scheme of polyol-based polymers. Xylitol (1), sorbitol (2), mannitol (3), and maltitol (4) were polymerized with sebacic acid (5) in different stoichiometries. A simplified representation of the polymers is shown. R can be a hydrogen, a polyol, or a sebacic acid molecule.

All chemicals were purchased from Sigma-Aldrich (St. Louis, Mo., USA) unless stated otherwise. Appropriate molar amounts of the polyol and sebacic acid monomer were melted in a 250 mL round bottom flask at 150° C. under a blanket of inert gas, and stirred for 2 h. Vacuum (~50 mTorr) was applied for 2-12 h, yielding the pre-polymers poly(xylitol sebacate) (PXS) 1:1 and PXS 1:2, poly(sorbitol sebacate) (PSS) 1:1 and PSS 1:2, poly(mannitol sebacate) (PMS) 1:1 and PMS 1:2, and poly(maltitol sebacate) (PMtS) 1:4 (FIG. 4, Table 3-1). The pre-polymers were sized using linear polymer standards on gel permeation chromatography (GPC) using tetrahydrofuran (THF) on Styragel columns (series of HR-4, HR-3, HR-2, and HR-1, Waters, Milford, Mass., USA). ¹H-NMR spectra were obtained of all pre-polymers in $(CD_3)_2NCOD$, on a Varian Unity-300 NMR spectrometer. The chemical composition of the pre-polymers was determined by comparing the signal integrals of the polyol, and compared to the signal integrals of sebacic acid. The signal intensities showed peaks of —OC$\underline{H}_2$(C$\underline{H}$(OR))$_n$C$\underline{H}_2$O— at 3.5-5.5 ppm from the polyol, and peaks of —COC$\underline{H}_2$C$\underline{H}_2$C$\underline{H}_2$— at 1.3, 1.6 and 2.3 ppm from sebacic acid. The PPS polymers were produced by another polycondensation step using 120-150° C. under vacuum (~2 Pa) for 4 days (see Table 3-2 for specific curing conditions). Attenuated total reflectance-Fourier transform infrared spectroscopy (ATR-FTIR) analysis was performed on these polymer networks using a Nicolet Magna-IR 500 spectrophotometer. The wettability of PPS polymers was determined by contact-angle measurements, and the hydration of these polymers, determined by mass differential after 24 h in ddH$_2$O at 37° C. The water-in-air contact angle of polymer films was measured using the sessile-drop method and VCA2000 image analysis software (n=10). Tensile tests were performed on hydrated (ddH$_2$O at 37° C.>24 h) dog-bone shaped polymer strips (n=4) and conducted on an Instron 5542 (according to ASTM standard D412-98a) using a 50 or a 500 N load cell equipped with Merlin software. Glass transition temperature (T$_g$) and other potential phase transitions were measured within the temperature range of −90° C. and 250° C. with a heating/cooling rate of 10° C. per minute using a Q1000 DSC equipped with Advantage Software v2.5 (TA Instruments, Newcastle, Del. USA) and analyzed with Universal Analysis Software v4.3A (TA Instruments). The mass densities were measured using a pycnometer (Humboldt, MFG. CO), and crosslink density (n) as well as the relative molecular mass between crosslinks (M$_c$) were calculated from the following equations for an ideal elastomer, where E$_0$ is the Young's modulus, R is the universal gas constant, T is the temperature and ρ is the mass density:

$$n = \frac{E_o}{3RT} = \frac{\rho}{M_c} \qquad \text{Eqn. 1}$$

In Vitro Degradation of PPS Polymers

Degradation rates via hydrolysis were observed of sol-free PPS samples (n=4) continuously agitated at 37° C. in 20 mL PBS containing sodium azide (0.05% w/v), or in 20 mL of 0.1 M NaOH at 37° C. as previously reported (J. Yang, A. R. Webb, S. J. Pickerill, G. Hageman, G. A. Ameer, Synthesis and evaluation of poly(diol citrate) biodegradable elastomers. *Biomaterials* 2006, 27, (9), 1889-1898; incorporated herein by reference). At designated time points, samples were removed, washed in ddH$_2$O, incubated in ethanol overnight, dried at 90° C. for 1 d and weighed again to determine mass loss. Mass loss was calculated from dry weight at t (M$_t$) and compared to the dry weight at the start of the study (M$_0$) using the following equation:

$$M_{Loss} = \frac{M_o - M_t}{M_o} \times 100\% \qquad \text{Eqn. 2}$$

In Vitro Biocompatibility of PPS Polymers

Glass Petri dishes (60 mm diameter, Fisher Scientific) contained 3 g of cured elastomers (120° C., 140 mTorr for 4 days). Petri dishes prepared with a 1.5% w/v PLGA (65/35, high M$_w$, Lakeshore Biomedical, Birmingham, Ala., USA) solution in dichloromethane at 60 uL/cm$^2$ and subsequent solvent evaporation served as control. Washes with sterile PBS were done and before the polymer loaded dishes were autoclaved. Primary human foreskin fibroblasts (HFF, ATCC, Manassas, Va., USA) were cultured in high glucose Dulbecco's Minimal Essential Medium (DMEM) supplemented with 10% (v/v) fetal bovine serum (Invitrogen), 100 µg/mL streptomycin (Invitrogen), and 100 U/mL penicillin (Invitrogen). Cells between passage three and six were harvested using trypsin 0.025%/EDTA 0.01% and quenched with an equal volume of medium to resuspend the cells. Additional cell systems were chosen from tissues with mechanical properties that match, or fall close to the mechanical properties of specific PPS polymers tested. A human bone cell line derived from an osteosarcoma (OS) (CRL-1545, ATCC, Manassas, Va., USA) was cultured in PMtS 1:4 coated dishes. A human

TABLE 2

| Pre-polymer | Composition by $^1$H-NMR | T$_m$$^a$ (° C.) | M$_w$ (g/mol) | M$_n$ (g/mol) | PDI |
|---|---|---|---|---|---|
| PXS 1:1 | 1.10:1.00 | ~80 | 2443 | 1268 | 1.9 |
| PXS 1:2 | 1.08:2.00 | ~100 | 6202 | 2255 | 2.7 |
| PSS 1:1 | 0.91:1.00 | ~80 | 6093 | 3987 | 1.5 |
| PSS 1:2 | 0.89:2.00 | ~100 | 23013 | 8990 | 2.6 |
| PMS 1:1 | 0.99:1.00 | ~100 | 3182 | 2038 | 1.6 |
| PMS 1:2 | 1.06:2.00 | ~120 | 10097 | 4379 | 2.3 |
| PMtS 1:4 | 1.18:4.00 | ~130 | 13265 | 2992 | 4.4 |

$^a$T$_m$s are temperatures where the polymer revealed a transition from a white, opaque wax to a clear flowing liquid.

TABLE 3

| Polymer (curing condition) | Young's Modulus (MPa) | Ultimate Tensile Stress (MPa) | Ultimate Elongation (%) | Contact Angle (°) | T$_g$ (° C.) | Hydration by Mass (%) | ρ (g/cm$^3$) | n (mol/m$^3$) | M$_c$ (g/mol) |
|---|---|---|---|---|---|---|---|---|---|
| PXS 1:1 (120° C., 2 Pa, 4 d) | 0.82 ± 0.15 | 0.61 ± 0.19 | 205.16 ± 55.76 | 26.5 ± 3.6 | 7.3 | 5.10 ± 0.12 | 1.18 ± 0.02 | 112.2 ± 30.5 | 10517.4 ± 102.1 |
| PXS 1:2 (120° C., 2 Pa, 4 d) | 5.33 ± 0.40 | 1.43 ± 0.15 | 33.12 ± 4.85 | 52.7 ± 5.7 | 22.9 | 1.74 ± 0.1 | 1.16 ± 0.02 | 729.32 ± 57.3 | 1585.1 ± 43.7 |
| PSS 1:1 (120° C., 2 Pa, 5 d) | 0.37 ± 0.08 | 0.57 ± 0.15 | 192.24 ± 60.12 | 9.6 ± 3.0 | 18.1 | 6.28 ± 0.27 | 1.13 ± 0.04 | 50.6 ± 10.3 | 22320.1 |
| PSS 1:2 (120° C., 2 Pa, 4 d) | 2.67 ± 0.12 | 1.16 ± 0.33 | 65.94 ± 24.87 | 36.6 ± 3.1 | 26.9 | 1.80 ± 0.09 | 1.16 ± 0.02 | 365.3 ± 21.5 | 3175.2 |
| PMS 1:1 (140° C., 2 Pa, 5 d) | 2.21 ± 0.21 | 0.79 ± 0.10 | 50.54 ± 9.01 | 32.2 ± 9.0 | 16.5 | 4.45 ± 0.14 | 1.18 ± 0.02 | 302.4 ± 60.2 | 3902.2 |
| PMS 1:2 (140° C., 2 Pa, 5 d) | 12.82 ± 2.90 | 3.32 ± 0.76 | 44.99 ± 11.81 | 40.4 ± 9.3 | 32.2 | 1.82 ± 0.15 | 1.16 ± 0.03 | 1754.2 ± 242.4 | 661.3 |
| PMtS 1:4 (150° C., 2 Pa, 5 d) | 378.0 ± 33.0 | 17.64 ± 1.30 | 10.90 ± 1.37 | 26.3 ± 8.4 | 45.6 | 1.40 ± 0.03 | 1.18 ± 0.01 | n/a | n/a | muscle cell line derived from a rhabdomyosarcoma (RMS) (CCL-136, ATCC, Manassas, Va., USA) was cultured in PSS 1:1 coated dishes. Bovine articular chondrocytes (BAC) were harvested from femoropatellar grooves of 2-4 week-old bovine calves, as previously described (Tognana et al., Adjacent tissues (cartilage, bone) affect the functional integration of engineered calf cartilage in vitro. *Osteoarthritis Cartilage* 2005, 13, (2), 129-38; incorporated herein by reference) and cultured in PMS 1:2 coated dishes. Human umbilical vein endothelial cells (HUVECs) (Cambrex, Walkersville, Md.) were cultured on PXS 1:1 laden dishes, in EGM-2 media supplemented with SingleQuot Kits (Cambrex). HUVECs were used by passage five and in accordance with the manufacturer's instructions. The fibroblasts and tissue specific cells were seeded (at 7500 cells/cm$^2$) in PLGA- or PPS-laden dishes and were allowed to grow to a confluent cell monolayer at 37° C. and 5% $CO_2$, whilst imaged after 4 h and every subsequent day after initial seeding. Phase micrographs of cells were taken at 10× magnification using Axiovision software (Zeiss). For cell proliferation measurements, randomly picked areas were imaged and cells were counted and averaged. The area and circularity (G. Thurston, B. Jaggi, B. Palcic, Measurement of cell motility and morphology with an automated microscope system. *Cytometry* 1988, 9, (5), 411-417; incorporated herein by reference) of cell populations were calculated manually using perimeter and area measurements by using Axiovision software (Zeiss). The circularity C was calculated using the following formula:

$$C = \frac{4\pi A}{P^2} \qquad \text{Eqn. 3}$$

where A is the projected area of the cell and P is the perimeter of the cell. Circularity was used as an index of cell spreading. Three distinct cell populations (n=~80 total) were measured to find cell population means.

In Vivo Biocompatibility of PPS Polymers

PPS discs (d=10 mm, h=1 mm) were implanted. Comparable PLGA pellets were melt-pressed (0.3 g, 172° C., 5000 MPa) into a mold (d=10 mm, h=1 mm) using a Carver Hydraulic Unit Model #3912-ASTM (Carver, Inc. Wabash, Ind.). Two female Lewis rats (Charles River Laboratories, Wilmington, Mass.) weighing 200-250 grams had access to water and food ad libitum. Animals were cared for according to the protocols of the Committee on Animal Care of MIT in conformity with the NIH guidelines (NIH publication #85-23, revised 1985). The animals were anaesthetized using continuous 2% isoflurane/$O_2$ inhalation. The implants were introduced by three small midline dorsal incisions, and five polymer formulations were placed in subcutaneous pockets created by blunt lateral dissection. The skin was closed with staples. Rats were sacrificed, the implants were resected en bloc with surrounding tissue and fixed in formalin-free fixative (Accustain). These specimens were embedded in paraffin after a series of dehydration steps in ethanol and xylene. Sequential sections (8-15 μm) were stained with hematoxliyn and eosine (H&E) and histology was evaluated by a medical doctor (JPB). Throughout the study, all rats remained in good general health as assessed by their weight gain.

Statistical Analysis

Two-tailed student's t-tests with unequal variances were performed to determine statistical significance, where appropriate (Microsoft Excel, Redmond, Wash. USA). Non-parametric one-way ANOVA tests were also performed where appropriate (GraphPad Prism 4.02, GraphPad Software, San Diego, Calif. USA). Dunn's multiple comparison post-tests were used to determine significance between specific treatments. All tabulated and graphical data is reported as mean±S.D. Significance levels were set at * $p<0.05$.

Results

Pre-Polymer Synthesis and Characterization

Figure 5:
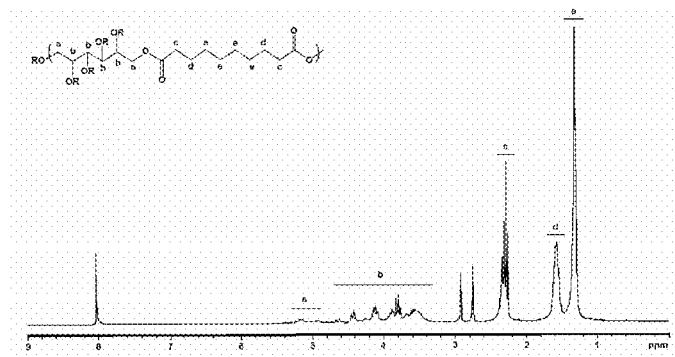
FIG. 5. (A) Representative $^1$H-NMR spectrum of PPS polymers, PMS 1:1 in this case. Signal intensities of the polyols at 3.5-5.5 ppm, and of sebacic acid in the polymer were identified at 1.2, 1.5, 2.2 ppm by hydrogens on the carbons labeled 'a'-'b', and 'c'-'e' respectively. (B) FTIR analysis of PPS polymers.
Figure 5:
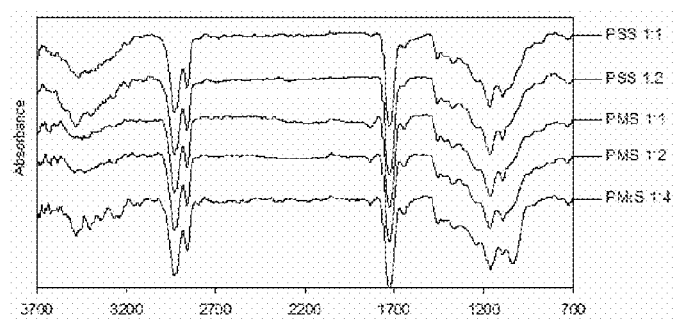

All pre-polymers were prepared through bulk polycondensation reactions of polyol and sebacic acid monomers (FIG. 4). The following stoichiometric ratios were prepared: PXS 1:1 and 1:2, PSS 1:1 and 1:2, PMS 1:1 and 1:2, and PMtS 1:4. FIG. 5A shows a typical $^1$H-NMR spectrum of a PPS prepolymer. The signal intensities showed peaks of —OC$\underline{H}_2$(C$\underline{H}$(OR))$_3$C$\underline{H}_2$O— at 3.5-5.5 ppm from the polyol (mannitol in this case), and peaks of —COC$\underline{H}_2$C$\underline{H}_2$C$\underline{H}_2$— at 1.3, 1.6, and 2.3 ppm from sebacic acid. The chemical composition of the pre-polymers was determined by calculating the ratios of the signal integrals of the polyol to sebacic acid. $^1$H-NMR revealed polymer compositions that are summarized in Table 2. In addition, weight average molecular weight ($M_w$), number average molecular weight ($M_n$) and polydispersity index (PDI) for all PPS pre-polymers were determined by GPC, and are shown in Table 2. No distinct, broad peaks associated with a melting temperature ($T_m$) could be detected with DSC for the pre-polymers, most likely due to the polydispersity of the pre-polymers. Empirically, different temperatures were used to process these pre-polymers, and are listed in Table 2 as well. All polymers are clear, viscous liquids at 130° C., and waxy, opaque materials at room temperature. The pre-polymers are soluble in common solvents like ethanol, acetone, dimethyl sulfoxide, tetrahydrofuran, and dimethylformamide.

Characterization and Physical Properties of PPS Polymers

The pre-polymers were thermally cured into thermoset networks under different curing conditions, as summarized in Table 3. FT-IR of the cured polymers confirmed ester bond formation in all polymers, with a stretch at 1,740 cm$^{-1}$ which corresponds to the ester linkages. A broad stretch was also observed at approximately 3,448 cm$^{-1}$ which corresponds to hydrogen bonded hydroxyl groups. The FT-IR spectrum of PMtS 1:4 illustrated an additional stretch at 1,050 cm$^{-1}$, compared to the spectra of the other PPS polymers, which is associated with the vibration of the ether bond within the maltitol monomer (FIG. 5B).

The thermal properties of the PPS polymers were revealed by DSC: PXS 1:1, PSS 1:1 and PMS 1:1 had glass-transition temperatures below room temperature. PXS 1:2, PSS 1:2, and PMS 1:2 had glass-transition temperatures higher than the 1:1 stoichiometries, but still remained below 37° C., indicating that these PPSs are rubbery at physiological temperatures. PMtS 1:4 showed the highest glass transition temperature, at 45° C., demonstrating that this polymer is glassy at 37° C. (Table 3).

Increasing the sebacic acid monomer feed ratio resulted in a higher crosslink density and in lesser wettability of the polymers, as demonstrated by the hydration as well as higher contact angle measurements, as summarized in Table 3.

Mechanical Properties of PPS Polymers

All hydrated PPS polymers, with the exception of PMtS 1:4, showed stress versus strain plots that are typical of hydrated high and low modulus PPS elastomers above their $T_g$. FIG. 6A, B show representative stress versus strain plots for the PPS polymers studied herein. The average tensile Young's modulus, ultimate tensile strength (UTS) and elongation at break for all PPS polymers are summarized in Table 3. PMtS 1:4 was observed to be the stiffest material and revealed a tensile Young's modulus of 378±33.0 MPa, UTS of 17.6±1.30 MPa, and average elongation at break of 10.90±1.37% (Table 3, FIG. 6A). PSS 1:1 was observed to be the softest material with a tensile Young's modulus of 0.37±0.08 MPa, UTS of 0.57±0.15 MPa and elongation at break of 192.24±60.12%. Limited hysteresis was seen after 1000 cyclic compression cycles up to 50 N for the PXS 1:1 elastomer as shown in FIG. 6C. Also, PPS pre-polymers are miscible and allowed for formation of co-polymers. As an example, three PXS 1:1 and PMtS 1:4 co-polymers were produced. Representative stress versus strain plots for different PXS 1:1/PMtS 1:4 w/w ratios are shown in FIG. 6D: the tensile Young's moduli of these PXS 1:1/PMtS 1:4 co-polymers were 7.25±0.47 MPa, 3.94±0.32 MPa and 1.61±0.22 MPa for the 25/75, 50/50 and 75/25 PXS 1:1/PMtS 1:4 w/w ratios respectively.

In Vitro Degradation of PPS Polymers

Figure 7:
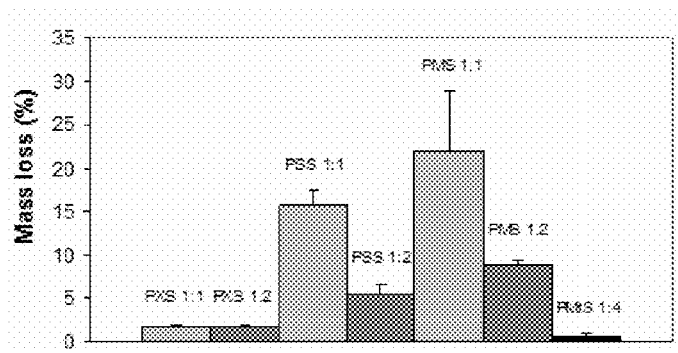
FIG. 7. (A) Degradation of PPS polymers in PBS at 37° C. for 105 d. (B) Degradation of PPS polymer in 0.1 N NaOH.
Figure 7:
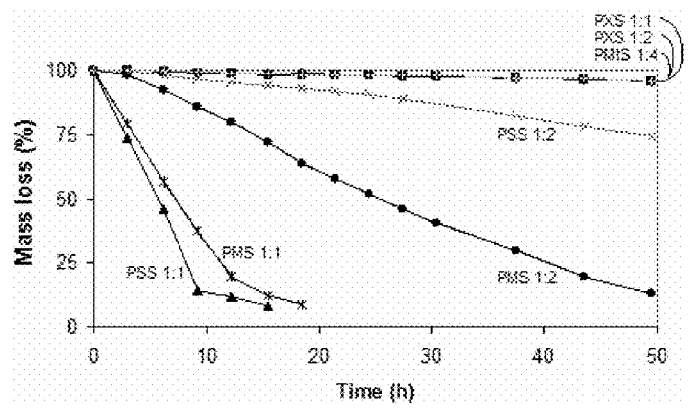

Biodegradable polyesters can degrade through hydrolysis. Therefore, the in vitro degradation under physiological conditions was investigated. Mass loss was detected for all PPS polymers (FIG. 7A). After 105 days, PXS 1:1 and 1:2 revealed a mass loss of a mere 1.78±0.30% and 1.88±0.22% respectively. PXS 1:1 did not reveal a similar mass loss profile as PSS 1:1 (15.66±1.75%) and PMS 1:1 (21.90±6.99%): the latter two polymers had degraded more than their corresponding 1:2 stoichiometries (PSS 1:2 (5.57±1.00%) and PMS 1:2 (9.00±0.54%)). At this point, PMtS 1:4 showed the least mass loss of 0.76±0.30% (FIG. 7A). Although degradation under physiological conditions was observed for all PPS polymers, an additional in vitro degradation study in high pH (0.1 N NaOH) was performed as previously described (J. Yang, A. R. Webb, S. J. Pickerill, G. Hageman, G. A. Ameer, Synthesis and evaluation of poly(diol citrate) biodegradable elastomers. Biomaterials 2006, 27, (9), 1889-1898). Again, all polymers revealed a mass loss over a course of 50 h, and showed resemblance to what was found in the previous degradation study: at 50 h, PMtS 1:4 revealed a mass loss of 4.07±2.80%, and PXS 1:1 and 1:2 a mass loss of 4.40±0.33% and 4.24±0.52% respectively. PSS 1:1 and PMS 1:1 had fully degraded under 20 h. Also in concert with the previous degradation study, PSS 1:2 and PMS 1:2 degraded slower than the 1:1 stoichiometric ratios. After 50 h, 74.10±0.41% of the original mass of PSS 1:2, and 13-7.45% of PMS 1:2 remained (FIG. 7B).

In Vitro Biocompatibility

Figure 8:
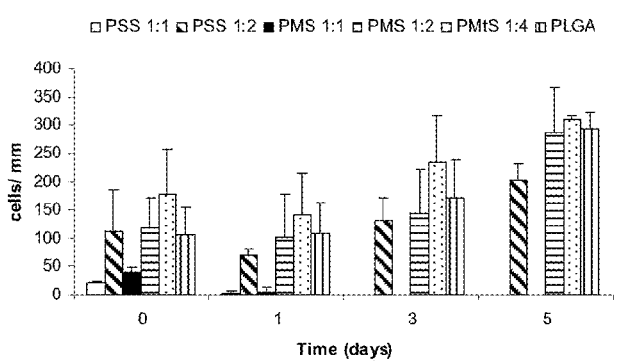
FIG. 8. (A) Attachment and proliferation of HFFs on PPS polymers. The (*) indicates significant difference (p<0.05) to the other PPS polymers for that time point. Representative phase contrast micrographic images of HFFs on PSS 1:1 (B), PSS 1:2 (C), PMS 1:1 (D), PMS 1:2 (E), PMtS 1:4 (F), and PLGA (G). Images are 10× magnification. Bars represent 150 micron.
Figure 8:
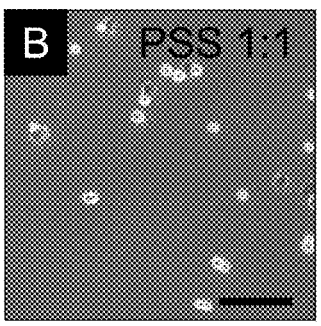
Figure 8:
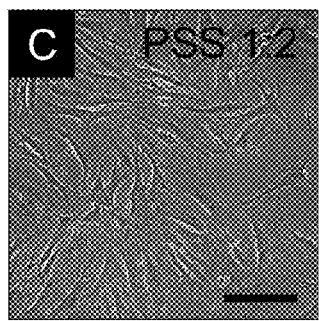
Figure 8:
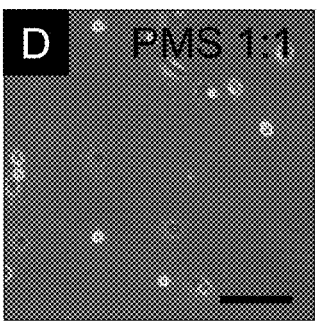
Figure 8:
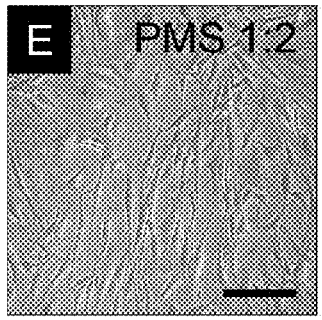
Figure 8:
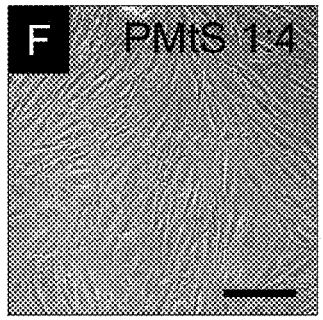
Figure 8:
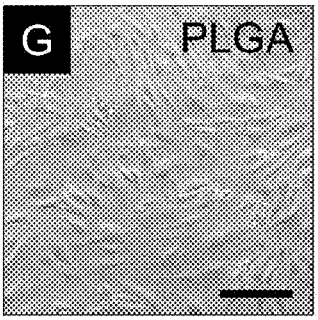
Figure 9:
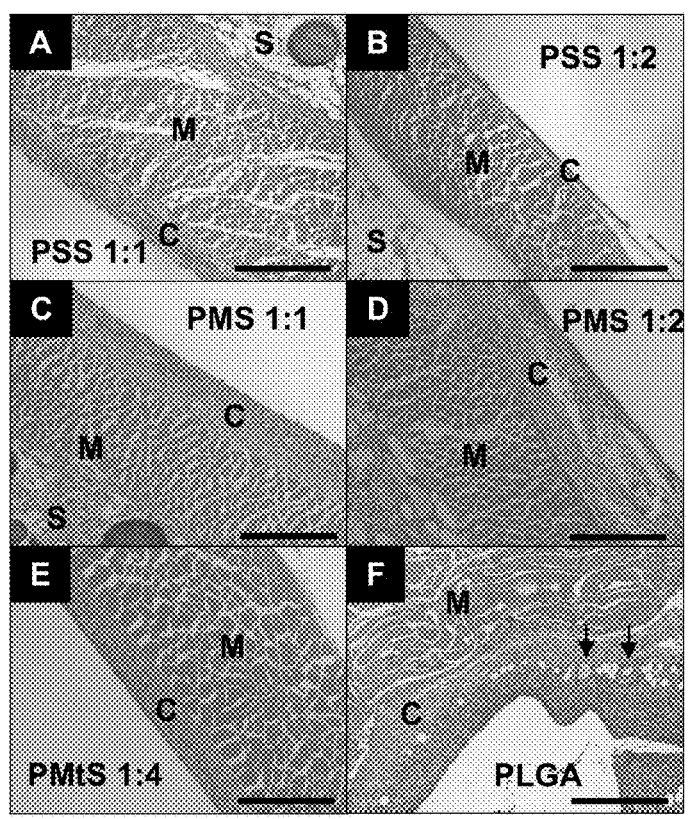
FIG. 9. Representative images of H&E stained sections demonstrating the acute inflammatory response to subcutaneous implanted PPS polymers. After 10 days, (A) PSS 1:1, (B) PSS 1:2, (C) PMS 1:1, (D) PMS 1:2, (E) PMtS 1:4 revealed mild inflammatory responses as compared to (F)

The biocompatibility of PXS 1:1 and PXS 1:2 elastomers has been reported elsewhere (J. P. Bruggeman, C. J. Bettinger, C. L. E. Nijst, D. S. Kohane, R. Langer, Biodegradable Xylitol-Based Polymers. Adv Mater. 2008, accepted; J. P. Bruggeman, C. J. Bettinger, R. Langer, Thermoset Biodegradable Xylitol-Based Elastomers: Degradation Profile and Biocompatibility. Submitted 2008; each of which is incorporated herein by reference). We therefore conducted an initial in vitro biocompatibility of the other PPS polymers with primary HFFs, as fibroblasts are important regulators of the wound-healing process in vivo. The initial attachment and subsequent proliferation into a confluent cell monolayer was compared to PLGA (FIG. 8). HFFs readily attached on all but PSS 1:1 and PMS 1:1 polymers. A confluent cell layer was achieved after 5 d for all substrates, except PSS 1:2 (achieved at 7 d, data not shown). Sporadic attachment was seen on PSS 1:1 and PMS 1:1 substrates (FIG. 8A, B, D). The cells that attached to PSS 1:1 and PMS 1:1 did not spread and did not subsequently proliferate into a confluent monolayer.

In Vivo Biocompatibility and Degradation

The in vivo biocompatibility of PPS polymers was evaluated via subcutaneous implantation in rats. After 10 days in vivo, the acute inflammatory response was mild for all implanted polymers. The surrounding tissues did not show necrosis, nor an abundant perivascular infiltration of mononuclear cells. In addition, the fibrous capsules surrounding the PPS polymers were thin (FIG. 9A-E). The assessment of the chronic inflammatory response after 12 weeks to the implants (FIG. 10), revealed thicker fibrous capsules in comparison to the acute inflammatory response at 10 days. The fibrous capsule formation surrounding PPS polymers however, seemed similar, or less to the prevalently used PLGA at 12 weeks (FIG. 10E). At this point, the chronic inflammation was still mild, as suggested by the thicknesses of these capsules and the presence of few visible vessels within the capsules (FIG. 10A-D). The PSS 1:1 elastomer appeared to have fully degraded at this time, without detectable traces, despite repetitive sectioning of the implantation area.

Initial In Vitro Biocompatibility Analysis of PPS for Tissue Specific Applications In vitro attachment and subsequent proliferation into a confluent cell monolayer of tissue specific cell lines and primary cells were assessed by light microscopy (FIG. 11). PMtS 1:4 revealed similar attachment and growth rate of a human osteosarcoma (OS) cell line (derived from bone) compared to PLGA. In addition, cell morphology, as assessed by circularity and cell area, was not significantly different for OS cells that were cultured on PLGA (FIG. 11A i-v). A difference in cell morphology was found however, for a rhabdomyosarcoma (RMS) cell line (human muscle origin) that was cultured on PSS 1:2 substrates, and compared to PLGA (FIG. 11B i). RMS cells revealed more spindle like morphology before a confluent cell layer was achieved, as shown in FIG. 11B ii-v: cell circularity was significantly less for cells cultured on PSS 1:2 ($p<0.05$). In addition, RMS cells spread more, resulting in a larger cell area ($p<0.05$) (FIG. 11B iii). Initial attachment and subsequent cell numbers during proliferation were not different from PLGA. Cell numbers however, did reveal a significant difference for primary bovine articular chondrocytes (BAC) after 4 and 6 d culture on PMS 1:2, compared to PLGA (FIG. 11C i). A difference in chondrocyte morphology was also noted. Although cell area was greater for BACs cultured on PMS 1:2 ($p<0.05$), cell circularity was not significantly different ($p>0.05$) (FIG. 11C ii-v). HUVECs were cultured on PXS 1:1 and exhibited attachment, growth rates and cell morphology that were comparable to PLGA (FIG. 11D i-v).

Discussion

The synthesis of PPS polymers is straightforward and does not require the use of organic solvents or cytotoxic additives. The PPS polymers were produced in sub-kilogram quantities and are inexpensive. The first polycondensation step yields PPS pre-polymers that allowed processing into various scaffold geometries, after which the second polycondensation step cures the pre-polymers into a set crosslinked polymer network of desired shape. The curing conditions can be adjusted to modify crosslink densities of these networks within a modest range (C. J. Bettinger, J. P. Bruggeman, J. T. Borenstein, R. S. Langer, Amino alcohol-based degradable poly(ester amide) elastomers. Biomaterials 2008, 29, (15), 2315-2325; incorporated herein by reference). However, adjusting stoichiometry allowed for a much wider range of crosslink densities and subsequent polymer properties (Table 3). The reacting stoichiometry of sebacic acid to polyol was chosen such that the number of hydroxyl functionalities of the polyol was always greater than the number of carboxylic functionalities by 1 or 2, to ensure step-growth polymerization and still expose free hydroxyl groups in the polymer backbone. These free hydroxyl groups may contribute to intra-network hydrogen bond formation and be available for functionalization chemistries, such as previously shown (C.

L. E. Nijst, J. P. Bruggeman, J. M. Karp, L. Ferreira, A. Zumbuehl, C. J. Bettinger, R. Langer, Synthesis and Characterization of Photocurable Elastomers from Poly(glycerol-co-sebacate). *Biomacromolecules* 2007; incorporated herein by reference).

Figure 6:
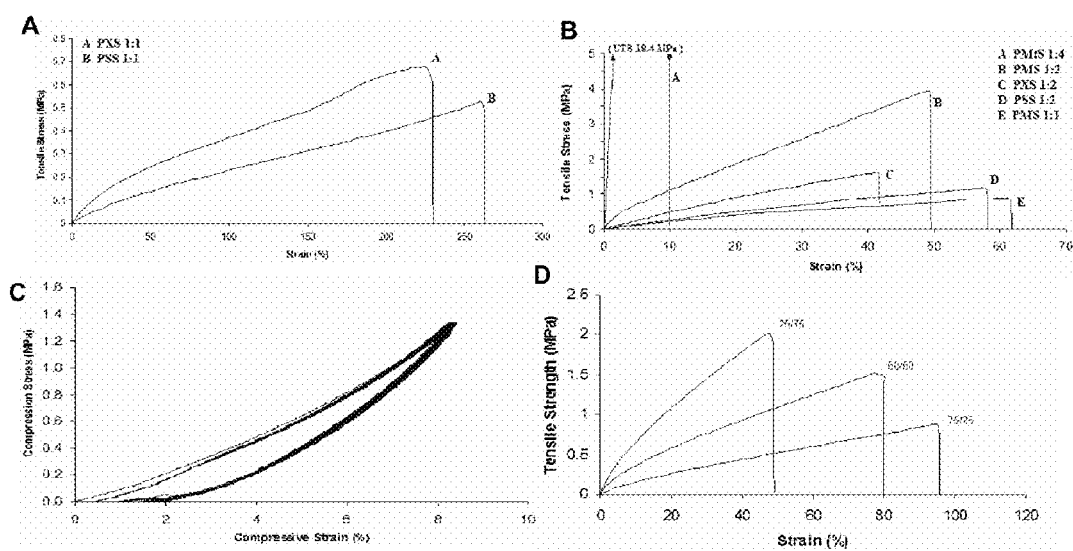
FIG. 6. (A) Typical tensile stress versus strain curves of low Young's modulus PPS elastomers (PXS 1:1 and PSS 1:1). (B) Typical tensile stress versus strain curves of PPS elastomers with higher Young's moduli. (C) First and last 10 cyclic compression cycles of a 1000 times up to 50 N on PXS 1:1. (D) Block co-polymers composed of low- and high modulus PPS polymers: PXS 1:1 and PMtS 1:4 respectively, with 25/75, 50/50 and 75/25 w/w PXS/PMtS ratios.

Of the PPS polymers, PXS and PSS revealed comparable physical and mechanical properties, most likely because their polyol monomers have $T_m$s close to each other (95 and 97° C. respectively) and have similar water solubility. PSS elastomers showed slightly lower contact angles and a higher degree of hydration, compared to PXS (Table 3). Using mannitol as a monomer produced PPS polymer films with higher Young's moduli and $T_g$s than PSS elastomers (FIG. 6), as well as higher contact angles (Table 3). Mannitol is a stereoisomer of sorbitol with a higher T, (165° C.) and lower water solubility, which may explain the differences observed between PSS and PMS elastomers. Maltitol-based polymers on the other hand, showed similar contact angles as PXS and PSS 1:2 stoichiometries, which can be explained if PMtS 1:4 is essentially viewed as a glucose:sorbitol:sebacate 1:1:4 polymer. However, maltitol allowed for higher sebacic acid monomer feed ratios, resulting in a high degree of crosslinking, and therefore in a glassy polymer with a $T_g$ above ambient and physiological temperatures, and of which water-uptake is limited (FIG. 6, Table 3). The tensile Young's moduli of PMtS 1:4 polymers are comparable to trabecular bone (50-100 MPa) and may potentially be developed for bone tissue engineering or osteosynthesis materials (K. S. Anseth, V. R. Shastri, R. Langer, Photopolymerizable degradable polyanhydrides with osteocompatibility. *Nat Biotechnol* 1999, 17, 156-159; incorporated herein by reference). Thus, this polymer design presents elastomers with Young's moduli that ranged from soft elastomeric materials (~0.4 MPa) in a rubbery state, to elastomers with high moduli (~380 MPa) that are glassy at physiological temperatures. In addition, co-polymers of PPS polymers can be produced as well.

The in vivo degradation mechanism PXS elastomers is dominated by surface erosion, as reported elsewhere. It is postulated that a higher crosslink density as well as the introduction of more hydrophobic entities (sebacic acid) were responsible for tuning the in vivo degradation rate. In vitro hydrolysis under physiological conditions occurred for all PPS polymers and revealed similar differences between the 1:1 and 1:2 stoichiometries, as was observed in vivo for PXS. However, in vitro degradation of PXS elastomers was significantly less than PSS and PMS elastomers, and comparable to the PMtS 1:4 polymer under similar conditions (FIG. 7A). This hydrolysis profile was confirmed for hydrolysis in a high pH environment (FIG. 7B). In vitro degradation rates of PXS however, did clearly not correspond to in vivo degradation rates. Similarly, during the in vivo biocompatibility study presented here, we observed that the PSS 1:1 polymer appeared to completely degrade within 12 weeks, but had only lost 15.66±1.75% of its original mass after 105 days in vitro. This in vivo mass loss of PSS 1:1 is similar to the previously observed degradation of PXS 1:1, which had an in vivo half life of 3-4 weeks.

PPS polymers support cell attachment with the exception of PSS 1:1 and PMS 1:1 elastomers (FIG. 8). The in vitro cell attachment and proliferation studies were performed without pre-treating or coating the polymers with adhesion proteins such as fibronectin and collagen. If cellular attachment is not warranted, which can be important in some applications (D. Motlagh, J. Yang, K. Y. Lui, A. R. Webb, G. A. Ameer, Hemocompatibility evaluation of poly(glycerol-sebacate) in vitro for vascular tissue engineering. *Biomaterials* 2006, 27, (24), 4315-4324; K. E. Schmalenberg, K. E. Uhrich, Micropatterned polymer substrates control alignment of proliferating Schwann cells to direct neuronal regeneration. *Biomaterials* 2005, 26, (12), 1423-1430; each of which is incorporated herein by reference), PSS 1:1 and PMS 1:1 can potentially be used as a (patterned) coatings, including contact guidance cues onto the biomaterial (D. M. Thompson, H. M. Buettner, Neurite outgrowth is directed by schwann cell alignment in the absence of other guidance cues. *Ann Biomed Eng.* 2006, 34, (1), 161-168; incorporated herein by reference). Alternatively, PSS 1:1 and PMS 1:1 elastomers could be modified with adhesion-promoting proteins and peptides by grafting them onto the exposed hydroxyl groups.

The fibrous capsules during the acute inflammatory response to PPS foreign materials seemed consistent with fibrous capsule thicknesses of previously reported values for soft thermoset elastomers (FIG. 9) (Y. Wang, G. A. Ameer, B. J. Sheppard, R. Langer, A tough biodegradable elastomer. *Nat Biotechnol* 2002, 20, (6), 602-606; J. P. Bruggeman, C. L. E. Nijst, C. J. Bettinger, J. M. Karp, M. Moore, R. Langer, D. S. Kohane, In vivo behavior of Poly(glycerol-co-sebacate)-acrylate: implications for a nerve guide material. Submitted 2008; J. P. Bruggeman, C. J. Bettinger, C. L. E. Nijst, D. S. Kohane, R. Langer, Biodegradable Xylitol-Based Polymers. *Adv Mater.* 2008, Accepted; J. Yang, A. R. Webb, S. J. Pickerill, G. Hageman, G. A. Ameer, Synthesis and evaluation of poly(diol citrate) biodegradable elastomers. *Biomaterials* 2006, 27, (9), 1889-1898; J. P. Bruggeman, C. J. Bettinger, R. Langer, Thermoset Biodegradable Xylitol-Based Elastomers: Degradation Profile and Biocompatibility. Submitted 2008; C. J. Bettinger, J. P. Bruggeman, J. T. Borenstein, R. S. Langer, Amino alcohol-based degradable poly(ester amide) elastomers. *Biomaterials* 2008, 29, (15), 2315-2325; each of which is incorporated herein by reference). However, the fibrous capsules of the chronic inflammatory response surrounding the higher modulus materials (PMS 1:2 and PMtS 1:4), seemed more pronounced than observed for PSS 1:2 and PMS 1:1, but was still less than reported values for PLA and PLGA polymers, which are frequently reported around 400-600 microns thick (FIG. 10) (Y. Wang, G. A. Ameer, B. J. Sheppard, R. Langer, A tough biodegradable elastomer. Nat *Biotechnol* 2002, 20, (6), 602-606; Y. Wang, Y. M. Kim, R. Langer, In vivo degradation characteristics of poly(glycerol sebacate). *J Biomed Mater Res A* 2003, 66, (1), 192-7; P. Mainil-Varlet, S. Gogolewski, P. Nieuwenhuis, Long-term soft tissue reaction to various polylactides and their in vivo degradation. *J Biomed Mater Res A* 1996, 7, (12), 6713-6721; each of which is incorporated herein by reference).

Thus, PPS polymers are composed of structural units that are endogenous to the mammalian metabolism, but have advantages associated with synthetic polymers. PPS polymers revealed mechanical properties that can potentially be useful in a variety of surgical procedures and tissue engineering applications. As an example, human ulnar metacarpophalangeal thumb joint ligament has a tensile stress and a Young's modulus of 11.4±1.2 MPa and 37.3±5.1 MPa respectively (K. Firoozbakhsh, I. S. Yi, M. S. Moneim, Y. Umada, A study of ulnar collateral ligament of the thumb metacarpophalangeal joint. *Clin Orthop Relat Res.* 2002, 403, 240-247; incorporated herein by reference), and several human cervical spinal components such as intervertebral discs, as well as their associated ligaments, have mechanical properties (S. K. Ha, Finite element modeling of multi-level cervical spinal segments ($C_3$-$C_6$) and biomechanical analysis of an elastomer-type prosthetic disc. *Med Eng Phys.* 2006 July, 28(6), 534-41 2006, 28, (6), 534-541; incorporated herein by reference) that fall within the limits of the PPS polymer platform shown here. This is also true for softer tissues such as nerves (B. L. Rydevik, M. K. Kwan, R. R. Myers, R. A. Brown, K. J. Triggs, S. L. Woo, S. R. Garfin, An in vitro mechanical and histological study of acute stretching on rabbit tibial nerve. *J Orthop Res* 1990, 8, (5), 694-701; incorporated herein by reference) and blood vessels (V. Clerin, J. W. Nichol, M. Petko, R. J. Myung, W. Gaynor, K. J. Gooch, Tissue Engineering of Arteries by Directed Remodeling of Intact Arterial Segments. *Tissue Eng* 2003, 9, (3), 461-472; incorporated herein by reference) for instance. For musculoskeletal tissue engineering and reconstructive surgery purposes, PPS polymers seem promising materials (FIG. 11).

Conclusions

PPS polymers are synthetic in nature but have the advantage of being composed of structural units endogenous to human metabolism. Chemical, physical, and mechanical properties as well as degradation rates of the polymers described in this Example can be tuned by altering the polyol and stoichiometry of the reacting sebacic acid. Potentially, many co-polymers and composite materials are possible, resulting in a considerable number of polymers accessible through the synthetic scheme presented here. PPS polymers exhibited comparable biocompatibility to materials approved for human use, such as PLGA.

Example 4

Biodegradable Xylitol-Based Elastomers

Degradation Profile and Biocompatibility

We have recently developed a versatile platform of biodegradable elastomers, based on polycondensation reactions of xylitol with sebacic acid, referred to as poly(xylitol sebacate) (PXS) elastomers (J. P. Bruggeman, C. J. Bettinger, C. L. E. Nijst, D. S. Kohane, R. Langer, Biodegradable Xylitol-Based Polymers. *Adv Mater* 2008; which is incorporated herein by reference). In this Example, we describe the synthesis and in vivo behavior of an array of thermoset PXS elastomers in detail. Three PXS elastomer formulations were synthesized by altering the stoichiometric ratios of xylitol and sebacic acid. An additional formulation was produced through a copolymerization strategy. PXS elastomers were characterized in vivo and exhibited enhanced biocompatibility compared to PLGA. More importantly, PXS elastomers displayed structural integrity and form stability throughout degradation. The half-life of these elastomers ranged from ~3 weeks to ~52 weeks. Based on morphological evaluation of PXS implants, we propose a surface eroding mechanism for PXS elastomers.

Materials and Methods

Synthesis and Characterization of PXS Pre-Polymers

All chemicals were purchased from Sigma-Aldrich (St. Louis, Mo., USA) unless otherwise stated. Appropriate molar amounts of the polyol and reacting acid monomer were melted in a round bottom flask at 150° C. under a blanket of inert gas, and stirred for 2 h. Vacuum (~50 mTorr) was applied yielding the pre-polymers PXS 1:1 (12 h), PXS 2:3 (6 h) and PXS 1:2 (6 h). The pre-polymers were sized using gel permeation chromatography (GPC) using tetrahydrofuran on Styragel columns (series of HR-4, HR-3, HR-2, and HR-1, Waters, Milford, Mass., USA) and linear standards. FT-IR analysis was carried out on a Nicolet Magna-IR 550 spectrometer. $^1$H-NMR spectra were obtained of the PXS pre-polymers in $C_2D_6O$, on a Varian Unity-300 NMR spectrometer. The chemical composition of the pre-polymers was determined by calculating the signal integrals of xylitol, and compared to the signal integrals of sebacic acid. The signal intensities showed peaks of —O$\underline{CH}_2$(C$\underline{H}$(OR))$_3$C$\underline{H}_2$O— at 3.5-5.5 ppm from xylitol, and peaks of —COC$\underline{H}_2$CH$_2$C$\underline{H}_2$— at 1.3, 1.6 and 2.3 ppm from sebacic acid.

Synthesis and Characterization of PXS Elastomers

All PXS polymers were produced by further polycondensation (120° C., 140 mTorr for 4 days. Tensile tests were performed on dog-bone shaped polymer strips that were hydrated for at least 24 h in ddH$_2$O on an Instron 5542 (according to ASTM standard D412-98a). Differential scanning calorimetry (DSC) was performed as previously reported (J. P. Bruggeman, C. J. Bettinger, C. L. E. Nijst, D. S. Kohane, R. Langer, Biodegradable Xylitol-Based Polymers. *Adv Mater* 2008). Briefly, glass transition temperature ($T_g$) and other potential phase transitions were measured within the temperature range of −90° C. and 250° C. with a heating/cooling rate of 10° C. per minute using a Q1000 DSC equipped with Advantage Software v2.5 (TA Instruments, Newcastle, Del. USA) and analyzed with Universal Analysis Software v4.3A (TA Instruments). The change of $T_g$ over time ($\Delta T_g$) was calculated by subtracting the $T_g$ at the start of the experiment ($T_{g, t=0}$) with the $T_g$ at time point t ($T_{g, t=0}$):

$$\Delta T_g = T_{g,t=0} - T_{g,t} \qquad \text{Equation 1}$$

The mass density was measured using a pycnometer (Humboldt, MFG. CO), and crosslink density (n) as well as the relative molecular mass between crosslinks ($M_c$) were calculated from the following equations for an ideal elastomer, where $E_0$ is the Young's modulus, R is the universal gas constant, T is the temperature, and ρ is the mass density:

$$n = \frac{E_o}{3RT} = \frac{\rho}{M_c} \qquad \text{Equation 2}$$

The water-in-air contact angle measurements were carried out as previously mentioned (Y. Wang, G. A. Ameer, B. J. Sheppard, R. Langer, A tough biodegradable elastomer. *Nat Biotechnol* 2002, 20, (6), 602-606; incorporated herein by reference). Degradation of the explanted polymers was determined by mass differential, calculated from the polymer's dry weight at t compared to the dry weight at the start of the study. All data are expressed as mean±standard deviation.

In Vivo Implantation of PXS Elastomers

Female Lewis rats (Charles River Laboratories, Wilmington, Mass.) weighing 200-250 g were housed in groups of 2 and had access to water and food ad libitum. Animals were cared for according to the approved protocols of the Committee on Animal Care of the Massachusetts Institute of Technology in conformity with the NIH guidelines for the care and use of laboratory animals (NIH publication #85-23, revised 1985). The animals were anaesthetized using continuous 2% isoflurane/O$_2$ inhalation. Two small midline incisions on the dorsum of the rat and the implants were introduced in lateral subcutaneous pockets created by blunt dissection. The skin was closed using staples. Each rat carried either PXS 1:1 and PXS 1:2, or PXS 2:3 and 50/50 PXS 1:1/1:2, or PLGA implants. The animals were inspected daily until post-operative day 10 for any wound healing problems. Throughout the study, all rats stayed in good general health as assessed by their weight gain.

In Vivo Degradation and Biocompatibility of PXS Elastomers

For the degradation study, discs of photocured PXS elastomers (diameter 10×1.6 mm) (n=4) were implanted subcutaneously in rats. Before implantation, polymer discs were weighed ($M_0$) and their thickness ($H_0$) was measured between two glass cover slides using calipers. To investigate in vivo degradation, implants were harvested at pre-determined time points and were collected in sterile saline. Directly upon surgical removal, the explants were dabbed dry, weighed ($M_{wet}$), and their thickness ($H_t$) was measured again. The explants were then dried at 90° C. for 3 days and weighed ($W_{dry}$) again. Water content (hydration) by mass and implant dimensions over time were calculated as follows:

$$\frac{M_{wet} - M_{dry}}{M_{dry}} \times 100\% \qquad \text{Equation 3}$$

for water content, and $$\frac{|H_t - H_0|}{H_0} \times 100\% \qquad \text{Equation 4}$$

for implant size.

The mass loss over time was calculated using Equation 3.

$$\frac{M_0 - M_{dry}}{M_0} \times 100\% \qquad \text{Equation 5}$$

Compression tests were performed on the wet explants with a 50N load cell at a compression rate of 5 mm/min using an Instron 5542, according to ASTM standard D575-91. All samples were compressed to 20% and the compression modulus was calculated from the initial slope (0-10%) of the stress-strain curve. The compression modulus was determined before implantation, and the ratio of the initial modulus was calculated to the modulus at the pre-determined time point ($E_t$) as follows:

$$\frac{E_t}{E_0} \times 100\% \qquad \text{Equation 6}$$

Explants dedicated for scanning electron microscopy (SEM) were sputter-coated with platinum/palladium (≈250 A), mounted on aluminum stubs with carbon tape, and examined on a JEOL JSM-5910. Explants dedicated to determine sol content were weighed ($M_{dry}$), placed in 100% ethanol for 3 days on a orbital shaker, dried at 90° C. for 3 days and weighed ($M_{solfree}$) again. The sol content of the explants was calculated, using the following equation:

$$\frac{M_{dry} - M_{solfree}}{M_{solfree}} \times 100\% \qquad \text{Equation 7}$$

For biocompatibility analysis, explants and surrounding tissues were harvested, and fixed in Accustain for 24 h, dehydrated in graded ethanol (70-100%), embedded in paraffin, sectioned using a microtome (4 μm). Sequential sections (8-15 μm) were stained with hematoxilyn and eosin (H&E). The H&E stains were used to analyze for the presence of fibroblasts and neutrophils in the tissues surrounding the material, and for the presence of multinucleated giant cells, ingrowth of cells into the material as well as phagocytosis of the material. Tissue macrophages were identified by staining sections with primary rabbit anti-rat CD68 (1:200, Abcam, England UK) (D. R. Greaves, S. Gordon, Macrophage-specific gene expression: current paradigms and future challenges. Int J Hematol. 2002, 76, (1), 6-15; incorporated herein by reference), followed by goat anti-mouse secondary antibody (Vector Burlingame, Calif. USA). Samples were incubated with streptavidin horseradish peroxidase (1:100, Dako, Denmark) and developed with DAB substrate chromogen (Dako). Histology images were recorded with a Zeiss CCD Camera equipped with Axiovision software (Zeiss, Germany). At least four measurements were taken in ten random sections to calculate fibrous capsule thickness and macrophage frequency.

Statistical Analysis

At least four fibrous capsule thickness measurements were made across at least ten randomly selected images per sample. Histological macrophage scoring was also based on at least ten randomly selected images. Two-tailed student's t-tests with unequal variances were performed to determine statistical significance, where appropriate (Microsoft Excel, Redmond, Wash. USA).

Results

Pre-Polymer Synthesis and Characterization

PXS pre-polymers were prepared by a polycondensation reaction between xylitol and sebacic acid in three stoichiometric ratios (FIG. 12A). Polymers with xylitol: sebacic acid ratios of 1:1, 2:3 and 1:2 were prepared, designated PXS 1:1, PXS 2:3 and PXS 1:2 respectively. Chemical compositions were confirmed by $^1$H-NMR spectra, as shown in Table 4 below. Molecular weight distributions were determined by GPC for PXS pre-polymers, and are summarized in Table 4. As empirically determined, PXS pre-polymers have accessible melting temperatures ($T_m$s) and allowed for processing and mixing these pre-polymers. A blend of PXS 1:1 and PXS 1:2 at 50/50 w/w was prepared and, similar to the PXS 1:1, PXS 2:3 and PXS 1:2 pre-polymers, was further cured into elastomeric networks (FIG. 12B).

TABLE 4

| Pre-polymer | Composition by $^1$H-NMR | $T_m{}^a$ (° C.) | $M_w$ (g/mol) | $M_n$ (g/mol) | PDI |
| --- | --- | --- | --- | --- | --- |
| PXS 1:1 | 1.0:0.91 | 80 | 2443 | 1268 | 1.9 |
| PXS 1:1/1:2 | 1.0:1.56 | 90 | 4690 | 1689 | 2.8 |
| PXS 2:3 | 1.0:1.63 | 100 | 3156 | 1117 | 2.7 |
| PXS 1:2 | 1.0:1.85 | 100 | 6202 | 2255 | 2.7 |

$^a T_m$s are temperatures where the polymer revealed a transition from a white, opaque wax to a clear flowing liquid.

Characterization of PXS Elastomers

PXS 1:1, PXS 2:3 and PXS 1:2 elastomers as well as a co-polymer of PXS 1:1 and PXS 1:2 at 50/50 w/w (PXS 1:1/1:2) revealed stress strain curves as shown in FIG. 13. Tensile Young's moduli ranged from 0.82±0.15 to 5.33±0.40 MPa as previously reported for PXS 1:1 and PXS 1:2 elastomers (J. P. Bruggeman, C. J. Bettinger, C. L. E. Nijst, D. S. Kohane, R. Langer, Biodegradable Xylitol-Based Polymers. Adv Mater 2008). The PXS 1:1/1:2 co-polymer and PXS 2:3 revealed Young's moduli of 2.32±0.27 and 3.42±0.13 MPa respectively, and fall within the limits defined by PXS 1:1 and 1:2. Mechanical properties of PXS elastomers are summarized in Table 5. Physical properties such as glass-transition temperatures ($T_g$s) and crosslink densities ranged from a lower limit defined by PXS 1:1 (7.3° C. and 10517.4±102.1 mol/m$^3$), to upper limit values of PXS 1:2 (22.9° C. and 1585.1±43.7 mol/m$^3$) and in between these limits the values of PXS 1:1/1:2 (18.7° C. and 3685.7±90.5 mol/m$^3$) and PXS 2:3 (20.2° C. and 2521.6±100.5 mol/m$^3$). The wettability of these elastomers, determined by contact angle measurements and hydration, showed a similar trend: PXS 1:1 exhibited the lowest contact angle and highest hydration by mass (26.5±3.6° and 12.6±0.4%), PXS 1:2 the highest contact angle with the lowest hydration (52.7±5.7° and 4.1±0.3%) and PXS 1:1/1:2 and PXS 2:3 (31.6±4.3°, 8.3±1.6% and 43.8±2.2°, 3.7±0.9% respectively) in between the values of PXS 1:1 and PXS 1:2. The physical properties of PXS elastomers are summarized in Table 5.

TABLE 5

| Polymer | Curing process | Young's Modulus (MPa) | Compression Modulus (MPa) | $T_g$ (°C.) | Contact angle (°) | Hydration by mass (%) | ρ (g/cm³) | n (mol/m³) | $M_c$ (g/mol) |
|---|---|---|---|---|---|---|---|---|---|
| PXS 1:1 | 120° C., 2 Pa, 4 d | 0.82 ± 0.15 | 1.67 ± 0.20 | 7.3 | 26.5 ± 3.6 | 12.6 ± 0.4 | 1.18 ± 0.02 | 112.2 ± 30.5 | 10517.4 ± 102.1 |
| PXS 1:1/1:2 | 120° C., 2 Pa, 4 d | 2.32 ± 0.27 | 2.67 ± 0.59 | 18.7 | 31.6 ± 4.3 | 8.3 ± 1.6 | 1.17 ± 0.03 | 317.4 ± 21.0 | 3685.7 ± 90.5 |
| PXS 2:3 | 120° C., 2 Pa, 4 d | 3.42 ± 0.13 | 3.71 ± 0.20 | 20.2 | 43.8 ± 2.2 | 3.7 ± 0.9 | 1.18 ± 0.01 | 468.0 ± 29.2 | 2521.6 ± 100.5 |
| PXS 1:2 | 120° C., 2 Pa, 4 d | 5.33 ± 0.40 | 5.68 ± 0.56 | 22.9 | 52.7 ± 5.7 | 4.1 ± 0.3 | 1.16 ± 0.02 | 729.3 ± 57.3 | 1585.1 ± 43.7 |

In Vivo Degradation of PXS Elastomers

Similar to the mechanical properties and physical characterization of PXS elastomers, the in vivo mass loss, hydration by mass, construct sol content, mechanical deterioration, and implant thickness, were also confined to the outer limits that were defined by PXS 1:1 and PXS 1:2 elastomers, and the values of the PXS 1:1/1:2 co-polymer and PXS 2:3 elastomer within these limits. The in vivo half life of PXS 1:1 was approximately 3 to 4 weeks, and revealed a linear decrease in mass over time (FIG. 14A). PXS 1:2 degraded much slower, with 76.7±3.7% of its original dry weight remaining at 28 weeks in vivo. In the first 12 weeks in vivo, PXS 1:2 did not show a decrease in mass at all (FIG. 14A). The PXS 1:1/1:2 co-polymer appeared to have a mass loss profile that was a combination of the separate PXS 1:1 and PXS 1:2 elastomers: it had an in vivo half life of ~15 weeks and had almost completely degraded at 27 weeks (FIG. 14A). The PXS 2:3 elastomer had a projected half life of ~30 weeks, and similar to the PXS 1:2 elastomer, showed an initial lag time where no mass loss was observed and after which a linear loss in mass had commenced (FIG. 14A).

Thermoset polymer networks can contain a fraction of loose, entangled macromers that are not covalently attached to the polymer network, referred to as the sol fraction. Upon degradation of thermoset polyesters, scission of esters bonds occurs, potentially changing a network's sol fraction. This behavior was observed for all PXS elastomers in vivo: sol fractions were observed to increase over time, being at their highest values near complete degradation, but never exceeding 30% of its dry mass (FIG. 14A). However, sol fractions of polymers that showed the least mass loss never exceeded 10% of their dry mass at that time (FIG. 14A, B).

$\Delta T_g$s of PXS elastomers over time were initially negative, and then increased with time, as displayed for PXS 1:1/1:2, PXS 2:3 and PXS 1:2 elastomers, as degradation occurred (FIG. 14C). The $T_g$ measurements were performed on sol-free, dry elastomers, and therefore only resemble the thermal properties of the 'naked' degrading polymer network, without plasticizers such as water and other small molecules.

Implant thickness during degradation, as observed for all PXS elastomers, was shown to gradually decrease over time. This decrease was the most for PXS 1:1 and the least for PXS 1:2 (FIG. 14D). Hydration of the PXS elastomers was relatively mild and never exceeded 40% of their dry mass (FIG. 14E). PXS 1:1 elastomers showed the highest hydration during their degradation. PXS 1:1/1:2, as well as the PXS 2:3 and PXS 1:2 elastomers demonstrated similar trends in hydration as displayed in FIG. 14E.

Mechanical testing of the elastomers showed a decrease in Young's modulus over time, except for PXS 1:2 elastomers (FIG. 14F). At 23.3±3.7% mass loss of the PXS 1:2 elastomers, no deterioration in Young's modulus was observed. When PXS 1:1 elastomers had degraded 24.7±11.0% however, a decrease of 35.2±4.7% of their original mechanical properties was observed. The relationship between mass loss and mechanical properties is shown in FIG. 15, and demonstrates the different trend for the PXS 1:2 elastomers in comparison to the other PXS elastomers. Unlike PXS 1:2, the other polymers (PXS 1:1, PXS 2:3 and PXS 1:1/1:2) reveal a linear decrease of mechanical properties when the material degrades.

PXS elastomers maintain a high level of structural integrity and form stability, which seemed obvious when compared to a thermoplastic, such as PLGA, which is known to swell up to 100-300% of its original dimensions during degradation (FIG. 16A-J) (E. W. Henry, T. H. Chiu, E. Nyilas, T. M. Brushart, P. Dikkes, R. L. Sidman, Nerve regeneration through biodegradable polyester tubes. *Exp Neurol.* 1985, 90, 652-676; W. F. A. Den Dunnen, M. F. Meek, D. W. Grijpma, P. H. Robinson, J. M. Schakernraad, In vivo and in vitro degradation of poly[50/50(85/15 L/D)LA/ε-CL], and the implications for the use in nerve reconstruction. *J. Biomed. Mater. Res. A* 2000, 51, 575-585); each of which is incorporated herein by reference).

Morphological Assessment of PXS and PLGA Implants

PXS elastomers appeared smooth-surfaced and optically clear at early time points upon visual inspection. Surfaces appeared progressively rough, and implants became more opaque as degradation occurred. SEM analysis of the surface as well as the interior of the implants revealed a degradation front that progressed inward from the surface for PXS elastomers (only PXS 1:1 and PXS 1:2 are shown) (FIG. 17A-F). After 1 week, surfaces of PXS 1:1 elastomers showed excavates and the interior of the implant seemed intact (FIG. 36A). When PXS 1:1 implants had lost more than 76.7±3.7% of their initial mass, a more porous surface was observed (FIG. 17B). At 5 weeks in vivo, when PXS 1:2 elastomers had not shown mass loss, no changes were observed, either on their surface, nor on the interior of the implant (FIG. 17C). Degrading PXS 1:2 elastomers also demonstrated a rough, porous surface upon degradation, but the pores were smaller, compared to the PXS 1:1 surfaces (FIG. 36D). PLGA implants were examined by SEM as well. PLGA implants degrade through bulk degradation and this behavior was confirmed by SEM images: the interior of PLGA implants showed signs of degradation, whereas the surface did not (FIG. 17E, F).

In Vivo Biocompatibility of PXS 1:1 and 1:2 Elastomers

An initial biocompatibility study of PXS 1:1 and PXS 1:2 elastomers was reported previously, and demonstrated competitive in vivo biocompatibility compared to PLGA implants (J. P. Bruggeman, C. J. Bettinger, C. L. E. Nijst, D. S. Kohane, R. Langer, Biodegradable Xylitol-Based Polymers. *Adv Mater* 2008). Following implantation, none of the animals showed post-operative abnormalities in their wound healing process. At all time points during the in vivo experiment, all PXS implants were encased by very thin, translucent fibrous capsules, and appeared thicker macroscopically for PLGA implants. On autopsy, occasional vascularization of the capsule was observed for PXS implants, but this seemed more obvious for PLGA implants. Clinically, the surrounding tissues of the implants all appeared to be normal. At a low magnification (2.5×), the thin fibrous capsule surrounding PXS 1:1 elastomers after 1 week in vivo is observed (FIG. 18A). When this was examined in more detail (black rectangular in FIG. 18A magnified 20×), this capsule seemed to consist mainly of lymphocytes, macrophages and fibroblasts (FIG. 18B). At a significant mass loss of PXS 1:1 elastomers (after 5 weeks in vivo), the degradation products did not seem to influence fibrous capsule thickness, as demonstrated in the low magnification overview in FIG. 18C. However, at 5 weeks, the fibrous capsule showed signs of chronic inflammation with fewer lymphocytes, macrophages and giant cells at the polymer surface, as shown at 20× (FIG. 18D). The thin fibrous capsule was predominantly composed fibroblasts and vascularization of this capsule was not obvious. Fibrous capsules surrounding the PXS 1:2 elastomers were comparable, despite the slower degradation rate. The acute inflammatory response was limited to where the foreign material touched surrounding tissues, and the capsule in contact with the elastomer was thin, as shown at low magnification (FIG. 19A). At a higher magnification (FIG. 19B) lymphocytes, macrophages and fibroblasts were visible in this capsule, corresponding to a similar wound healing response as to the PXS 1:1 implants. As for PXS 1:1 elastomers, PXS 1:2 elastomers did not trigger noticeable infiltration in the surrounding tissues, (FIG. 19B). After 28 weeks of implantation time, PXS 1:2 elastomers were still encased by a thin surrounding fibrous capsule as shown in FIG. 19C. At the corners of the implants, where most friction with surrounding tissues is expected, a fibrous capsule of less than 20 cell layers thick was observed (FIG. 19D). This fibrous capsule was mostly composed of fibroblasts with a few scattered macrophages and giant cells at the polymer/tissue interface. After the first week in vivo, the capsules surrounding PLGA implants were evidently vascularized (FIG. 20). In addition, tissues that were not in direct contact with the implants seemed infiltrated with mononuclear cells (FIG. 20A, B). This response was almost absent for PXS elastomers. The initial wound healing response seemed to involve more macrophages for PLGA implants (FIG. 20B) than observed for the PXS elastomers. Upon degradation of PLGA implants at 12 weeks in vivo, a different tissue response was observed, compared to PXS elastomers: a much thicker fibrous capsule (FIG. 20C) that seemed to contain a high number of macrophages and giant cells as well as evident phagocytosis of polymer was observed (FIG. 20D).

When the sections were stained with antibodies against CD68, a qualitative difference was observed for PXS elastomers and PLGA polymers (FIG. 21A-I), as expected based on the H&E observations. When these qualitative observations were quantified, a difference in biocompatibility was noted between PXS elastomers and the PLGA polymer. FIG. 22A demonstrates the difference in fibrous capsule thickness surrounding the implants. Differences in percentage of activated macrophages (CD68+ cells) of the total surrounding cell population were also significantly different between PXS and PGLA implants (FIG. 22B), showing that PXS elastomers did not recruit macrophages as was the case for PLGA polymers.

Discussion

Tuning the in vivo behavior of thermoset PXS elastomers was possible by adjusting monomer feed ratio as well as by co-polymerization of pre-polymers using different stoichiometries. Taking step-growth polymer kinetics into account, and using the hydroxyl groups as the dominant functionality by 1, the PXS 1:2 stoichiometry represented the maximum limit of accessible crosslinking densities for PXS elastomers. As the number of aliphatic monomers in the polymerization reaction were increased to alter crosslink density, similar changes in glass transition and tensile Young's modulus, as well as contact angles and degradation rates were observed. Similar to reported degradation rates for FDA-approved thermoplastic polymers such as PLGA (J. C. Middleton, A. J. Tipton, Synthetic biodegradable polymers as orthopedic devices. *Biomaterials* 2000, 21, 2335-2346; incorporated herein by reference) and poly($^{50}/_{50}$($^{85}/_{15}$ D/L)-lactic-co-$\epsilon$-caprolactone) (W. F. A. Den Dunnen, M. F. Meek, D. W. Grijpma, P. H. Robinson, J. M. Schakernraad, In Vivo and in vitro degradation of poly[50/50(85/15 L/D)LA/s-CL], and the implications for the use in nerve reconstruction. *J Biomed Mater Res A* 2000, 51, 575-585; incorporated herein by reference), subcutaneous degradation rates of PXS elastomers could be tuned from 7 weeks (PXS 1:1), up to a projected life time of a little over 2 years (PXS 1:2) (FIG. 14A). These degradation rates were accessible for PXS elastomers without consequences in construct swelling (FIG. 14C) or form stability during degradation (FIGS. 16 and 17). This is an important advantage for small-feature medical devices such as flexible drug eluting chips, sensors, peripheral nerve conduits, and small vascular grafts.

The mechanism by which thermoset PXS elastomers degraded in vivo appeared to be dominated by surface erosion, as demonstrated by morphological studies (FIG. 17). As previously reported (J. P. Bruggeman, B. J. De Bruin, C. J. Bettinger, R. Langer, Synthesis and Characterization of Biodegradable Poly(polyol sebacate) Polymers. Submitted 2008; incorporated herein by reference), PXS 1:1 and 1:2 elastomers revealed in vitro mass losses of 1.78±0.30% and 1.88±0.22% respectively, after 105 days in PBS at 37° C. The obvious discrepancy of the in vitro mass loss versus the in vivo mass loss for PXS 1:1 elastomers, may suggest that the surface erosion of PXS elastomers is enzyme-driven.

We observed an initial negative and subsequent positive in $\Delta T_g$ of PXS elastomers during degradation. A negative $\Delta T_g$ seems in accordance with a bulk degrading profile, as a random cleavage of esters will potentially decrease crosslink density, and thereby lowering the $T_g$ of the material. However, when enzyme-driven surface erosion is assumed, an increase in $T_g$ is expected to be observed: enzymes are most likely sterically shielded from cleaving esters within the bulk of the material and may preferably cleave esters on the exposed, more mobile polymer chains. The observed in vivo kinetics of $T_g$ suggest that both degradation mechanisms occur in vivo, but that surface degradation is the most dominating profile with the highest rate.

The in vivo biocompatibility profile was comparable for PXS 1:1 and 1:2 elastomers, which suggests that biocompatibility is constant across PXS materials with varied degradation rates and mechanical properties. PXS revealed excellent biocompatibility when compared to PLGA, as PXS recruited less macrophages and was encased by thinner fibrous capsules.

Conclusions

Biodegradable PXS elastomers enable precise control of material properties by adjusting the stoichiometric ratios as well as the possibility of synthesizing co-polymers. A wide range of in vivo degradation rates and mechanical properties were achieved. In vivo degradation of PXS elastomers occurred primarily through surface erosion. PXS elastomers retained structural integrity and form stability during degradation. PXS elastomers are biocompatible regardless of degradation rate and mechanical properties.

Other Embodiments

The foregoing has been a description of certain non-limiting preferred embodiments of the invention. Those of ordinary skill in the art will appreciate that various changes and modifications to this description may be made without departing from the spirit or scope of the present invention, as defined in the following claims.

What is claimed is:

1. A polymer, wherein the backbone consists of alternating polyol and polycarboxylic acid units, wherein:
    monomers used to form the polymers are selected from the group consisting of alkanedioic acids having two carboxylic acid groups and sugar alcohols comprising at least four hydroxyl groups; and
    the ratio of the sugar alcohol units to the alkanedioic acid units in the polymer is 1 unit of sugar alcohol to at least 2 units of alkanedioic acid.

2. The polymer according to claim 1, wherein one or more of the hydroxyl groups have been modified with one or more acrylate moieties.

3. The polymer according to claim 2, wherein the polymer is cross-linked via conjugation of one or more of the acrylate moieties with one or more free hydroxyl groups of the polymer.

4. The polymer according to claim 1, wherein the sugar alcohol is xylitol.

5. The polymer according to claim 1, wherein the alkanedioic acid is or comprises dimercaptosuccinic acid, oxalic acid, malonic acid, succinic acid, glutaric acid, adipic acid, pimelic acid, suberic acid, azelaic acid, or sebacic acid.

6. The polymer according to claim 1, wherein the sugar alcohol comprises at least five (5) hydroxyl groups.

7. The polymer according to claim 1, wherein the ratio of the sugar alcohol units to the alkanedioic acid units in the polymer is 1 unit of sugar alcohol to 2 units of alkanedioic acid.

8. The polymer according to claim 1, wherein the sugar alcohol is erythritol, threitol, ribitol, arabinitol, xylitol, allitol, altritol, galactitol, sorbitol, mannitol, or iditol.

9. The polymer according to claim 5, wherein the alkanedioic acid is sebacic acid or glutaric acid.

10. The polymer according to claim 1, wherein the polymer is biodegradable.

11. The polymer according to claim 1, wherein the alkanedioic acid is a $C_8$-$C_{12}$ alkanedioic acid.

12. The polymer according to claim 1, wherein the polymer has an in-vivo half life of at least 8 months.

13. The polymer according to claim 1, wherein the polymer absorbs between 0% to 9.5% water.

14. The polymer according to claim 1, wherein the polymer has a Young's moduli of at least 0.5 to 12 MPa.

15. A polymer, wherein the backbone consists of alternating polyol and polycarboxylic acid units, wherein:
    monomers used to form the polymers are selected from the group consisting of alkanedioic acids having two carboxylic acid groups and sugar alcohols comprising at least four hydroxyl groups;
    one or more of the hydroxyl groups in the polymer has been modified with one or more acrylate moieties; and
    the ratio of the sugar alcohol units to the alkanedioic acid units in the polymer is 1 unit of sugar alcohol to at least 2 units of alkanedioic acid.

16. The polymer according to claim 15, wherein the alkanedioic acid is dimercaptosuccinic acid, oxalic acid, malonic acid, succinic acid, glutaric acid, adipic acid, pimelic acid, suberic acid, azelaic acid, or sebacic acid.

17. The polymer according to claim 15, wherein the alkanedioic acid is a $C_8$-$C_{12}$ alkanedioic acid.

18. A polymer, wherein the backbone consists of alternating sugar alcohol and alkanedioic acid units, wherein:
    each sugar alcohol unit independently comprises at least four —O— moieties;
    each alkanedioic acid unit independently has the structure of —C(O)(CH$_2$)$_x$C(O)—, wherein x is an integer of between 1 to 20, inclusive, and each of the —(CH$_2$)— unit is optionally and independently substituted;
    the ratio of the sugar alcohol units to the alkanedioic acid units in the polymer is 1 unit of sugar alcohol to at least 2 units of alkanedioic acid.

19. The polymer according to claim 18, wherein the sugar alcohol unit comprises one or more free hydroxyl groups.

20. The polymer according to claim 19, wherein one or more of the hydroxyl groups have been modified with one or more acrylate moieties.

21. The polymer according to claim 20, wherein the polymer is cross-linked via conjugation of one or more of the acrylate moieties with one or more free hydroxyl groups of the polymer.

22. The polymer according to claim 18, wherein the sugar alcohol is xylitol.

23. The polymer according to claim 18, wherein x is 8-12.

24. The polymer of claim 18, wherein the polymer is poly(xylitol-co-sebacate), wherein the ratio of the xylitol units and the sebacate units is 1:2.

* * * * *